(12) United States Patent
Bentwich

(10) Patent No.: US 7,618,814 B2
(45) Date of Patent: Nov. 17, 2009

(54) MICRORNA-RELATED NUCLEIC ACIDS AND USES THEREOF

(75) Inventor: Itzhak Bentwich, Kfar Daniel (IL)

(73) Assignee: Rosetta Genomics Ltd., Rehovot (IL)

( * ) Notice: Subject to any disclaimer, the term of this patent is extended or adjusted under 35 U.S.C. 154(b) by 96 days.

(21) Appl. No.: 10/535,164

(22) PCT Filed: Nov. 16, 2003

(86) PCT No.: PCT/IL03/00970

§ 371 (c)(1),
(2), (4) Date: Jul. 24, 2006

(87) PCT Pub. No.: WO2004/044123

PCT Pub. Date: May 27, 2004

(65) Prior Publication Data

US 2007/0134655 A1     Jun. 14, 2007

Related U.S. Application Data

(63) Continuation of application No. 10/604,985, filed on Aug. 29, 2003, which is a continuation-in-part of application No. 10/651,227, filed on Aug. 29, 2003, which is a continuation of application No. 10/605,924, filed on Aug. 29, 2003, which is a continuation-in-part of application No. 10/649,653, filed on Aug. 28, 2003, which is a continuation of application No. 10/605,923, filed on Aug. 28, 2003, which is a continuation-in-part of application No. 10/604,926, filed on Aug. 27, 2003, which is a continuation of application No. 10/345,201, filed on Jan. 16, 2003, which is a continuation-in-part of application No. 10/321,503, filed on Dec. 18, 2002, which is a continuation-in-part of application No. 10/310,914, filed on Dec. 6, 2002, which is a continuation-in-part of application No. 10/293,338, filed on Nov. 14, 2002, which is a continuation of application No. 10/604,727, filed on Aug. 13, 2003, said application No. 10/293,338 is a continuation of application No. 10/604,726, filed on Aug. 13, 2003.

(60) Provisional application No. 60/468,251, filed on May 7, 2003.

(51) Int. Cl.
C12N 15/00 (2006.01)
C12N 15/11 (2006.01)

(52) U.S. Cl. ................. 435/320.1; 536/23.1; 536/24.31

(58) Field of Classification Search ........................ None
See application file for complete search history.

(56) References Cited

U.S. PATENT DOCUMENTS 6,573,099 B2    6/2003    Graham
2002/0086356 A1    7/2002    Tuschl et al.
2003/0108923 A1    6/2003    Tuschl et al.

FOREIGN PATENT DOCUMENTS

| WO | WO 01/68836 | 9/2001 |
|----|----|----|
| WO | WO 01/75164 | 10/2001 |
| WO | WO 02/44321 | 6/2002 |
| WO | WO 02/094185 | 11/2002 |
| WO | WO 03/029459 | 4/2003 |
| WO | WO 03/070884 | 8/2003 |
| WO | WO 03/070903 | 8/2003 |
| WO | WO 03/070918 | 8/2003 |
| WO | WO 03/074654 | 9/2003 |

OTHER PUBLICATIONS

Somia et al, Nature Review Genetics 1: 91 (2000).*
Lee, R. C., R. L. Feinbaum and V. Ambros. The C. elegans heterochronic gene lin-4 encodes small RNAs with antisense complementarity to lin-14 Cell Dec. 3, 1993 843-854 75.
Wightman, B., I. Ha and G. Ruvkun. Posttranscriptional regulation of the heterochronic gene lin-14 by lin-4 mediates temporal pattern formation in C. elegans Cell Dec. 3, 1993 855-862 75.
Gallinaro, H., L. Domenjoud and M. Jacob. Structural study of the 5' end of a synthetic premessenger RNA from adenovirus. Evidence for a long-range exon-intron interaction J Mol Biol Jul. 14, 1994 205-225 240.
Crawford, E. D., E. P. Deantoni, R. Etzioni, V. C. Schaefer, R. M. Olson and C. A. Ross. Serum prostate-specific antigen and digital rectal examination for early detection of prostate cancer in a national community-based program. The Prostate Cancer Education Council Urology Jun. 1996 863-869 47.
Engdahl HM, Hjalt TA, Wagner EG. A two unit antisense RNA cassette test system for silencing of target genes. Nucleic Acids Res. Aug. 15, 1997 3218-27 25.
Dsouza, M., N. Larsen and R. Overbeek. Searching for patterns in genomic data Trends Genet Dec. 1997 497-498 13.
Moss, E. G., R. C. Lee and V. Ambros. The cold shock domain protein LIN-28 controls developmental timing in C. elegans and is regulated by the lin-4 RNA Cell 1997 637 88.

(Continued)

Primary Examiner—James Martinell
(74) Attorney, Agent, or Firm—Polsinelli Shughart PC; Teddy C. Scott, Jr.

(57) ABSTRACT

The present invention relates to a first group of novel genes, here identified as genomic address messenger or GAM genes, and a second group of novel operon-like genes, here identified as genomic record or GR genes. GAM genes selectively inhibit translation of known 'target' genes, many of which are known to be involved in various diseases. Nucleic acid molecules are provided respectively encoding 8607 GAM genes, and 1096 GR genes, as are vectors and probes both comprising the nucleic acid molecules, and methods and systems for detecting GAM and GR genes and specific functions and utilities thereof, for detecting expression of GAM and GR genes, and for selectively enhancing and selectively inhibiting translation of the respective target genes thereof.

6 Claims, 29 Drawing Sheets

OTHER PUBLICATIONS

Fire, A., S. Xu, M. K. Montgomery, S. A. Kostas, S. E. Driver and C. C. Mello. Potent and specific genetic interference by double-stranded RNA in Caenorhabditis elegans Nature Feb. 19, 1998 806-811 391.

Waterhouse, P. M., M. W. Graham and M. B. Wang. Virus resistance and gene silencing in plants can be induced by simultaneous expression of sense and antisense RNA Proc Natl Acad Sci U S A Nov 10, 1998 13959-13964 95.

NGO, H., C. Tschudi, K. Gull and E. Ullu. Double-stranded RNA induces mRNA degradation in Trypanosoma brucei Proc Natl Acad Sci U S A Dec 8, 1998 14687-14692 95.

Verma, S. and F. Eckstein. Modified oligonucleotides: synthesis and strategy for users Annu Rev Biochem 1998 99-134 67.

Wuchty, S., W. Fontana, I. L. Hofacker and P. Schuster. Complete suboptimal folding of RNA and the stability of secondary structures Biopolymers Feb. 1999 145-165 49.

Mathews, D. H., J. Sabina, M. Zuker and D. H. Turner. Expanded sequence dependence of thermodynamic parameters improves prediction of RNA secondary structure J Mol Biol May 21, 1999 911-940 288.

Chang, P. L. Encapsulation for somatic gene therapy Ann N Y Acad Sci Jun 18, 1999 146-158 875.

Zhang, M. Q. Large-scale gene expression data analysis: a new challenge to computational biologists Genome Res Aug. 1999 681-688 9.

Grisaru, D., M. Sternfeld, A. Eldor, D. Glick and H. Soreq. Structural roles of acetylcholinesterase variants in biology and pathology Eur J Biochem Sep. 1999 672-686 264.

Fire, A. RNA-triggered gene silencing Trends Genet Sep. 1999 358-363 15.

Tabara, H., M. Sarkissian, W. G. Kelly, J. Fleenor, A. Grishok, L. Timmons, A. Fire and C. C. Mello. The rde-1 gene, RNA interference, and transposon silencing in C. elegans Cell Oct. 15, 1999 123-132 99.

Ryo, A., Y. Suzuki, K. Ichiyama, T. Wakatsuki, N. Kondoh, A. Hada, M. Yamamoto and N. Yamamoto. Serial analysis of gene expression in HIV-1-infected T cell lines FEBS Lett Nov. 26, 1999 182-186 462.

Olsen, P. H. and v. Ambros. The lin-4 regulatory RNA controls developmental timing in Caenorhabditis elegans by blocking LIN-14 protein synthesis after the intitiation of translation Dev Biol Dec. 15, 1999. 671-680 216.

Tuschl, T., P. D. Zamore, R. Lehmann, D. P. Bartel and P. A. Sharp. Targeted mRNA degradation by double-stranded RNA in vitro Genes Dev Dec. 15, 1999 3191-3197 13.

Reinhart, B. J., F. J. Slack, M. Basson, A. E. Pasquinelli, J. C. Bettinger, A. E. Rougvie, H. R. Horvitz and G. Ruvkun. The 21-nucleotide let-7 RNA regulates developmental timing in Caenorhabditis elegans Nature Feb. 24, 2000 901-906 403.

Pitt, J. N., J. A. Schisa and J. R. Priess. P granules in the germ cells of Caenorhabditis elegans adults are associated with clusters of nuclear pores and contain RNA Dev Biol Mar. 15, 2000 315-333 219.

Hammond, S. M., E. Bernstein, D. Beach and G. J. Hannon, An RNA-directed nuclease mediates post-transcriptional gene silencing in Drosophila cells Nature Mar. 16, 2000 293-296 404.

Slack, F. J., M. Basson, Z. Liu, V. Ambros, H. R. Horvitz and G. Ruvkun. The lin-41 RBCC gene acts in the C. elegans heterochronic pathway between the let-7 regulatory RNA and the LIN-29 transcription factor Mol Cell Apr. 2000 659-669 5.

Fortier, E. and J. M. Belote. Temperature-dependent gene silencing by an expressed inverted repeat in Drosophila Genesis Apr. 2000 240-244 26.

Mourrain, P., C. Beclin, T. Elmayan, F. Feuerbach, C. Godon, J. B. Morel, D. Jouette, A. M. Lacombe, S. Nikic, N. Picault, K. Remoue, M. Sanial, T. A. VO and H. Vaucheret. *Arabidopis* SGS2 and SGS3 genes are required for posttranscriptional gene silencing and natural virus resistance Cell May 26, 2000 533-542 101.

Sijen, T. and J. M. Kooter. Post-transcriptional gene-silencing: RNAs on the attack or on the defense?Bioessays Jun. 2000 520-531 22.

Brenner, S., M. Johnson, J. Bridgham, G. Golda, D. H. Lloyd, D. Johnson, S. Luo, S. McCurdy, M. Foy, M. Ewan, R. Roth, D. George, S. Eletr, G. Albrecht, E. Vermaas, S. R. Williams, K. Moon, T. Burcham, M. Pallas, R. B. Dubridge, J. Kirchner, K. Fearon, J. MAO and K. Corcoran. Gene expression analysis by massively parallel signature sequencing (MPSS) on microbead arrays Nat Biotechnol Jun. 2000 630-634 18.

Ryo, A., Y. Suzuki, M. Arai, N. Kondoh, T. Wakatsuki, A. Hada, M. Shuda, K. Tanaka, C. Sato, M. Yamamoto and N. Yamamoto. Identification and characterization of differentially expressed mRNAs in HIV type 1-infected human T cells AIDS Res Hum Retroviruses Jul. 1, 2000 995 1005 16.

Nilsson, M., G. Barbany, D. O. Antson, K. Gertow and U. Landegren. Enhanced detection and distiction of RNA by enzymatic probe ligation Nat Biotechnol Jul. 2000 791-793 18.

Kent, W. J. and A. M. Zahler. Conservation, regulation, synteny, and introns in a large-scale C. briggsae-C. elegans genomic alignment Genome Res Aug. 2000 1115-1125 10.

Kennerdell, J. R. and R. W. Carthew. Heritable gene silencing in Drosophila using double-stranded RNA Nat Biotechnol Aug. 2000 896-898 18.

Smith, N. A., S. P. Singh, M. B. Wang, P. A. Stoutjesdijk, A. G. Green and P. M. Waterhouse. Total silencing by intron-spliced hairpin RNAs Nature Sep. 21, 2000 319-320 407.

Voinnet, O., C. Lederer and D. C. Baulcombe. A viral movement protein prevents spread of the gene silencing signal in Nicotiana benthamiana Cell Sep. 29, 2000 157-167 103.

Mette MF, Aufsatz W, van der Winden J, Matzke MA, Matzke AJ. Transcriptional silencing and promoter methylation triggered by double-stranded RNA. EMBO J. Oct. 2, 2000 5194-201 19.

Yang, D., H. Lu and J. W. Erickson. Evidence that processed small dsRNAs may mediate sequence-specific mRNA degradation during RNAi in Drosophila embryos Curr Biol Oct. 5, 2000 1191-1200 10.

Anandalakshmi, R., R. Marathe, X. Ge, J. M. Herr, Jr., C. Mau, A. Mallory, G. Pruss, L. Bowman and V. B. Vance. A calmodulin-related protein that suppresses prosttranscriptional gene silencing in plants Science Oct. 6, 2000 142-144 290.

Fagard, M., S. Boutet, J. B. Morel, C. Bellini and H. Vaucheret. AGO1, QDE-2, and RDE-1 are related proteins required for post-transcriptional gene silencing in plants, quelling in fungi, and RNA interference in animals Proc Natl Acad Sci U S A Oct. 10, 2000 11650-11654 97.

Paquinelli, A. E., B. J. Reinhart, F. Slack, M. Q. Martindale, M. I. Kuroda, B. Maller, D. C. Hayward, E. E. Ball, B. Degnan, P. Muller, J. Spring, A Srinivasan, M. Fishman, J. Finnerty, J. Corbo, M. Levine, P. Leahy, E. Davidson and G. Ruvkun. Conservation of the sequence and temporal expression of let-7 heterochronic regulatory RNA Nature Nov. 2, 2000 86-89 408.

Llave, C., K. D. Kasschau and J. C. Carrington. Virus-encoded suppressor of posttranscriptional gene silencing targets a maintenance step in the silencing pathway Proc Natl Acad Sci U S A Nov. 21, 2000 13401-13406 9.

Cogoni, C. and G. Macino. Post-transcriptional gene silencing across kingdoms Curr Opin Genet Dev Dec. 2000 638 10 p. 638 only.

Thomas, C. L., L. Jones, D. C. Baulcombe and A. J. Maule. Size constraints for targeting post-transcriptional gene silencing and for RNA-directed methylation in Nicotiana benthamiana using a potato virus X vector Plant J Feb. 2001 417-425 25.

Elbashier, S. M., J. Harborth, W. Lendeckel, A. Yalcin, K. Weber and T. Tuschl. Duplexes of 21-nucleotide RNAs mediate RNA interference in cultured mammalian cells Nature May 24, 2001 494-498 411.

Piccin, A., A. Salameh, C. Benna, F. Sandrelli, G. Mazzotta, M. Zordan, E. Rosato, C. P. Kyriacou and R. Costa. Efficient and heritable functional knock-out of an adult phenotype in Drosophila using a GAL4-driven hairpin RNA incorporating a heterologous spacer Nucleic Acids Res Jun. 15, 2001 E55-55 29.

Carter, R. J., I. Dubchak and S. R. Holbrook. A computational approach to identify genes for functional RNAs in genomic sequences Nucleic Acids Res Oct. 1, 2001 3928-3938 29.

Moss, E. G. RNA interference: it's a small RNA world Curr Biol Oct. 2, 2001 R772-775 11.

Lagos-Quintana, M., R. Rauhut, W. Lendeckel and T. Tuschl. Identification of novel genes coding for small expressed RNAs Science Oct. 26, 2001 853-858 294.

Itaya, A., A. Folimonov, Y. Matsuda, R. S. Nelson and B. Ding. Potato spindle tuber viroid as inducer of RNA silencing in infected tomato Mol Plant Microbe Interact Nov. 2001 1332-1334 14.

Mattick, J. S. Non-coding RNAs: the architects of eukaryotic complexity EMBO Rep Nov. 2001 986-991 2.
Elbashir, S. M., J. Martinez, A. Patkaniowska, W. Lendeckel and T. Tuschl. Functional anatomy of siRNAs for mediating efficient RNAi in Drosophila melanogaster embryo lysate Embo J Dec. 3, 2001 6877-6888 20.
Ambros, V. microRNAs: tiny regulators with great potential Cell Dec. 28, 2001 823-826 107.
Blaszczyk, J., J. E. Tropea, M. Bubunenko, K. M. Routzahn, D. S. Waught, D. L. Court and X. JI. Crystallographic and modeling studies of RNase III suggest a mechanism for double-stranded RNA cleavage Structure Dec. 2001 1225-1236 9.
Crete, P., S. Leuenberger, V. A. Iglesias, V. Suarez, H. Schob, H. Holtorf, S. Van Eeden and F. Meins. Graft transmission of induced and spontaneous post-transcriptional silencing of chitinase genes Plant J Dec. 2001 493-501 28.
Smallridge, R. A small fortune Nat Rev Mol Cell Biol Dec 2001 867 2.
Eddy, S. R. Non-coding RNA genes and the modern RNA world Nat Rev Genet Dec. 2001 919-929 2.
LU, C. M. miRNA bead detection Genaco Biomedical Products PHS 398 2001 1
Matzke, M., A. J. Matzke and J. M. Kooter. RNA: guiding gene silencing 2001 1080 293.
Grosshans, H. and F. J. Slack. Micro-RNAs: small is plentiful J Cell Biol Jan. 7, 2002 17-21 156.
Meshorer, E., C. Erb, R. Gazit, L. Pavlovsky, D. Kaufer, A. Friedman, D. Glick, N. Ben-Arie and H. Soreq. Alternative splicing and neuritic mRNA translocation under long-term neuronal hypersensitivity Science Jan. 18, 2002 508-512 295.
Paddison, P. J., A. A. Caudy and G. J. Hannon. Stable suppression of gene expression by RNAi in mammalian cells Proc Natl Acad Sci U S A Feb. 5, 2002 1443-1448 99.
Moss, E. G. MicroRNAs: hidden in the genome Curr Biol Feb 19, 2002 R138-140 12.
Banerjee, D. and F. Slack. Control of developmental timing by small temporal RNAs: a paradigm for RNA-mediated regulation of gene expression Bioessays Feb. 2002 119-129 24.
Elbashir, S. M., J. Harborth, K. Weber and T. Tuschl. Analysis of gene function in somatic mammalian cells using small interfering RNAs Methods Feb. 2002 199-213 26.
Han, Y. and D. Grierson. Relationship between small antisense RNAs and aberrant RNAs associated with sense transgene mediated gene silencing in tomato Plant J Feb. 2002 509-519 29.
Nicholson, R. H. and A. W. Nicholson. Molecular characterization of a mouse cDNA encoding Dicer, a ribonuclease III ortholog involved in RNA interference Mamm Genome Feb. 2002 67-73 13.
Puerta-Fernandez, E., A. Barroso-DelJesus and A. Berzal-Herranz. Anchoring hairpin ribozymes to long target RNAs by loop-loop RNA interactions Antisense Nucleic Acid Drug Dev Feb. 2002 1-9 12.
Giordano, E., R. Rendina, I. Peluso and M. Furia. RNAi triggered by symmetrically transcribed transgenes in Drosophila melanogaster Genetics Feb. 2002 637-648 160.
Martens, H., J. Novotny, J. Oberstrass, T. L. Steck, P. Postlethwait and W. Nellen. RNAi in Dictyostelium: the role of RNA-directed RNA polymerases and double-stranded RNase Mol Biol Cell Feb. 2002 445-453 13.
Mourelators, Z., J. Dostie, S. Paushkin, A. Sharma, B. Charroux, L. Abel, J. Rappsilber, M. Mann and G. Dreyfuss. miRNPs: a novel class of ribonucleoproteins containing numerous microRNAs Genes Dev Mar. 15, 2002 720-728 16.
Seggerson, K., L. Tang and E. G. Moss. Two genetic circuits repress the Caenorhabditis elegans heterochronic gene lin-28 after translation initiation Dev Biol Mar. 15, 2002 215-225 243.
Morel, J. B., C. Godon, P. Mourrain, C. Beclin, S. Boutet, F. Feuerbach, F. Proux and H. Vaucheret. Fertile hypomorphic Argonaute (ago1) mutants impaired in post-transcriptional gene silencing and virus resistance Plant Cell Mar. 2002 629-639 14.
Catalanotto, C., G. Azzalin, G. Macino and C. Cogoni. Involvement of small RNAs and role of the qde genes in the gene silencing pathway in Neurospora Genes Dev Apr. 1, 2002 790-795 16.
Boutla, A., K. Kalantidis, N. Tavernarakis, M. Tsagris and M. Tabler. Induction of RNA interference in Caenorhabditis elegans by RNAs derived from plants exhibiting post-transcriptional gene silencing Nucleic Acids Res Apr. 1, 2002 1688-1694 30.
Pasquinelli, A. E. and G. Ruvkun. Control of developmental timing by micrornas and their targets Annu Rev Cell Dev Biol Epub 2002 Apr. 2, 2002 495-513 18.
Paddison, P. J., A. A. Caudy, E. Bernstein, G. J. Hannon and D. S. Conklin. Short hairpin RNAs (shRNAs) induce sequence-specific silencing in mammalian cells Genes Dev Apr. 15, 2002 948-958 16.
Beclin, C., S. Boutet, P. Waterhouse and H. Vaucheret. A branched pathway for transgene-induced RNA silencing in plants Curr Biol Apr. 16, 2002 684-688 12.
Eddy, S. R. Computational genomics of noncoding RNA genes Cell Apr. 19, 2002 137-140 109.
Lagos-Quintana, M., R. Rauhut, A. Yalcin, J. Meyer, W. Lendeckel and T. Tuschl. Identification of tissue-specific microRNAs from mouse Curr Biol Apr. 30, 2002 735-739 12.
Kent, W. J. Blat—the Blast-like alignment tool Genome Res Apr. 2002 656-664 12.
Hutvagner, G. and P. D. Zamore. RNAi: nature abhors a double-strand Curr Opin Genet Dev Apr. 2002 225-232 12.
Nilsson, M., J. Baner, M. Mendel-Hartvig, F. Dahl, D. O. Antson, M. Gullberg and U. Landegren. Making ends meet in genetic analysis using padlock probes Hum Mutat Apr. 2002 410-415 19.
Pasquinelli, A. E. MicroRNAs: deviants no longer Trends Genet Apr. 2002 171-173 18.
Lai, E. C. Micro RNAs are complementary to 3' UTR sequence motifs that mediate negative post-transcriptional regulation Nat Genet Apr. 2002 363-364 30.
Schwarz, D. S. and P. D. Zamore. Why do miRNAs live in the miRNP? Genes Dev May 1, 2002 1025-1031 16.
Brantl, S. Antisense-RNA regulation and RNA interference Biochim Biophys Acta May 3, 2002 15-25 1575.
Li, H., W. X. Li and S. W. Ding. Induction and suppression of RNA silencing by an animal virus Science May 17, 2002 1319-1321 296.
Zamore, P. D. Ancient pathways programmed by small RNAs Science May 17, 2002 1265-1269 296.
Chen, S., E. A. Lesnik, T. A. Hall, R. Sampath, R. H. Griffey, D. J. Ecker and L. B. Blyn. A bioinformatics based approach to discover small RNA genes in the *Escherichia coli* genome Biosystems Mar.-May 2002 157-177 65.
Lee, N.S., T. Dohjima, G. Bauer, H. Li, M. J. Li, A. Ehsani, P. Salvaterra and J. Rossi. Expression of small interfering RNAs targeted against HIV-1 rev transcripts in human cells Nat Biotechnol May 2002 500-505 20.
Draghici, S. Statistical intelligence: effective analysis of high-density microarray data Drug Discov Today Jun. 1, 2002 S55-63 7.
Silhavy, D., A. Molnar, A. Lucioli, G. Szittya, C. Hornyik, M. Tavazza and J. Burgyan. A viral protein suppresses RNA silencing and binds silencing-generated, 21- to 25-nucleotide double-stranded RNAs Embo J Jun. 17, 2002 3070-3080 21.
Ayash-Rashkovsky, M., Z. Weisman, J. Diveley, R. B. Moss, Z. Bentwich and G. Borkow. Generation of Th1 immune responses to inactivated, gp120-depleted HIV-1 in mice with a dominant Th2 biased immune profile via immunostimulatory [correction of imunostimulatory] oligonucleotides—relevance to AIDS vaccines in developing countries Vaccine Jun. 21, 2002 2684-2692 20.
Bettencourt, R., O. Terenius and I. Faye. Hemolin gene silencing by ds-RNA injected into Cecropia pupae is lethal to next generation embryos Insect Mol Biol Jun. 2002 267-271 11.
Hooper, N. M. and A. J. Turner. The search for alpha-secretase and its potential as a therapeutic approach to Alzheimer s disease Curr Med Chem Jun. 2002 1107-1119 9.
Liu, Q., S. Singh and A. Green. High-oleic and high-stearic cottonseed oils: nutritionally improved cooking oils developed using gene silencing J Am Coll Nutr Jun. 2002 205S-211S 21.
Zeng, Y., E. J. Wagner and B. R. Cullen. Both natural and designed micro RNAs can inhibit the expression of cognate mRNAs when expressed in human cells Mol Cell Jun. 2002 1327-1333 9.
McManus, M. T., C. P. Petersen, B. B. Haines, J. Chen and P. A. Sharp. Gene silencing using micro-RNA designed hairpins Rna Jun. 2002 842-850 8.
Reinhart, B. J., E. G. Weinstein, M. W. Rhoades, B. Bartel and D. P. Bartel. MicroRNAs in plants Genes Dev Jul. 1, 2002 1616-1626 16.

McCaffrey, A. P., L. Meuse, T. T. Pham, D. S. Conklin, G. J. Hannon and M. A. Kay. RNA interference in adult mice Nature Jul. 4, 2002 38-39 418.

Hannon, G. J. RNA interference Nature Jul. 11, 2002 244-251 418.

Dennis, C. The brave new world of RNA Nature Jul. 11, 2002 122-124 418.

Jacque, J. M., K. Triques and M. Stevenson. Modulation of HIV-1 replication by RNA interference Nature Jul. 25, 2002 435-438 418.

Cullen, B. R. RNA interference: antiviral defense and genetic tool Nat Immunol Jul. 2002 597-599 3.

MA, C. and A. Mitra. Intrinsic direct repeats generate consistent post-transcriptional gene silencing in tobacco Plant J Jul. 2002 37-49 31.

Novina, C. D., M. F. Murray, D. M. Dykxhoorn, P. J. Beresford, J. Riess, S. K. Lee, R. G. Collman, J. Lieberman, P. Shankar and P. A. Sharp. siRNA-directed inhibition of HIV-1 infection Nat Med Jul. 2002 681-686 8.

Pomerantz, R. J. RNA interference meets HIV-1: will silence be golden? Nat Med Jul. 2002 659-660 8.

Zeng, Y. and B. R. Cullen. RNA interference in human cells is restricted to the cytoplasm Rna Jul. 2002 855-860 8.

Xiang, C. C., O. A. Kozhich, M. Chen, J. M. Inman, Q. N. Phan, Y. Chen and M. J. Brownstein. Amine-modified random primers to label probes for DNA microarrays Nat Biotechnol Jul. 2002 738-742 20.

Llave, C., K. D. Kasschau, M. A. Rector and J. C. Carrington. Endogenous and silencing-associated small RNAs in plants Plant Cell Jul. 2002 1605-1619 14.

Rhoades, M. W., B. J. Reinhart, L. P. LIM, C. B. Burge, B. Bartel and D. P. Bartel. Prediction of plant microRNA targets Cell Aug. 23, 2002 513-520 110.

Hipfner, D. R., K. Weigmann and S. M. Cohen. The bantam gene regulates Drosophila growth Genetics Aug. 2002 1527-1537 161.

Liu, Q., S. P. Singh and A. G. Green. High-stearic and High-oleic cottonseed oils produced by hairpin RNA-mediated post-transcriptional gene silencing Plant Physiol Aug. 2002 1732-1743 129.

Stoutjesdijk, P. A., S. P. Singh, Q. Liu, C. J. Hurlstone, P. A. Waterhouse and A. G. Green. hpRNA-mediated targeting of the Arabidopis FAD2 gene gives highly efficient and stable silencing Plant Physiol Aug. 2002 1723-1731 129.

Suzuma, S., S. Asari, K. Bunai, K. Yoshino, Y. Ando, H. Kakeshita, M. Fujita, K. Nakamura and K. Yamane. Identification and characterization of novel small RNAs in the aspS-yrvM intergenic region of the Bacillus subtilis genome Microbiology Aug. 2002 2591-2598 148.

Milligan, L., T. Forne, E. Antoine, M. Weber, B. Hemonnot, L. Dandolo, C. Brunel and G. Cathala. Turnover of primary transcripts is a major step in the regulation of mouse H19 gene expression EMBO Rep Aug. 2002 774-779 3.

Hamilton, A., O. Voinnet, L. Chappell and D. Baulcombe. Two classes of short interfering RNA in RNA silencing Embo J Sep. 2, 2002 4671-4679 21.

Lee, Y., K. Jeon, J. T. Lee, S. Kim and V. N. Kim. MicroRNA maturation: stepwise processing and subcellular localization Embo J Sep. 2, 2002 4663-4670 21.

Klahre, U., P. Crete, S. A. Leuenberger, V. A. Iglesias and F. Meins, Jr. High molecular weight RNAs and small interfering RNAs induced systemic posttranscriptional gene silencing in plants Proc Natl Acad Sci USA Sep. 3, 2002 11981-11986 99.

Park, W., J. Li, R. Song, J. Messing and X. Chen. Carpel Factory, a Dicer homolog, and HEN1, a novel protein, act in microRNA metabolism in Arabidopsis thaliana Curr Biol Sep. 3, 2002 1484-1495 12.

Jiang, M. and J. Milner. Selective silencing of viral gene expression in HPV-positive human cervical carcinoma cells treated with siRNA, a primer of RNA interference Oncogene Sep. 5, 2002 6041-6048 21.

Martinez, J., A. Patkaniowska, H. Urlaub, R. Luhrmann and T. Tuschl. Single-stranded antisense siRNAs guide target RNA cleavage in RNAi Cell Sep. 6, 2002 563-574 110.

Allshire, R. Molecular biology. RNAi and heterochromatin—a hushed-up affair Science Sep. 13, 2002 1818-1819 297.

Reinhart, B. J. and D. P. Bartel. Small RNAs correspond to centromere heterochromatic repeats Science Sep. 13, 2002 1831 297.

Baulcombe, D. DNA events. An RNA microcosm Science Sep. 20, 2002 2002-2003 297.

Llave, C., Z. Xie, K. D. Kasschau and J. C. Carrington. Cleavage of Scarecrow-like mRNA targets directed by a class of Arabidopsis miRNA Science Sep. 20, 2002 2053-2056 297.

Mochizuki, K., N. A. Fine, T. Fujisawa and M. A. Gorovsky. Analysis of a piwi-related gene implicates small RNAs in genome rearrangement in tetrahymena Cell Sep. 20, 2002 689-699 110.

Hutvagner, G. and P. D. Zamore. A microRNA in a multiple-turnover RNAi enzyme complex Science Sep. 20, 2002 2056-2060 297.

Coburn, G. A. and B. R. Cullen. Potent and specific inhibition of human immunodeficiency virus type 1 replication by RNA interference J Virol Sep. 2002 9225-9231 76.

Caudy, A. A., M. Myers, G. J. Hannon and S. M. Hammond. Fragile X-related protein and VIG associate with the RNA interference machinery Genes Dev Oct. 1, 2002 2491-2496 16.

Ishizuka, A., M. C. Siomi and H. Siomi. A Drosophila fragile X protein interacts with components of RNAi and ribosomal proteins Genes Dev Oct. 1, 2002 2497-2508 16.

Voinnet, O. RNA silencing: small RNAs as ubiquitous regulators of gene expression Curr Opin Plant Biol Oct. 2002 444-451 5.

Golden, T. A., S. E. Schauer, J. D. Lang, S. Pien, A. R. Mushegian, U. Grossniklaus, D. W. Meinke and A. Ray. Short Integuments1/Suspensor1/Carpel Factory, a Dicer homolog, is a maternal effect gene required for embryo development in Arabidopsis Plant Physiol Oct. 2002 808-822 130.

Merkle, I., M. J. Van Ooij, F. J. Van Kuppeveld, D. H. Glaudemans, J. M. Galama, A. Henke, R. Zell and W. J. Melchers. Biological significance of a human enterovirus B-specific RNA element in the 3'nontranslated region J Virol Oct. 2002 9900-9909 76.

Froeyen, M. and P. Herdewijn. RNA as a target for drug design, the example of Tat-TAR interaction Curr Top Med Chem Oct. 2002 1123-1145 2.

Carmell, M. A., Z. Xuan, M. Q. Zhang and G. J. Hannon. The Argonaute family: tentacles that reach into RNAi, developmental control, stem cell maintenance, and tumorigenesis Genes Dev Nov. 1, 2002 2733-2742 16.

Provost, P., D. Dishart, J. Doucet, D. Frendewey, B. Samuelsson and O. Radmark. Ribonuclease activity and RNA binding of recombinant human Dicer Embo J Nov. 1, 2002 5864-5874 21.

Zhang, H., F. A. Kolb, V. Brondani, E. Billy and W. Filipowicz. Human Dicer preferentially cleaves dsRNAs at their termini without a requirement for ATP Embo J Nov. 1. 2002 5875-5885 21.

Mallory, A. C., B. J. Reinhart, D. Bartel, V. B. Vance and L. H. Bowman. A viral suppressor of RNA silencing differentially regulates the accumulation of short interfering RNAs and micro-RNAs in tobacco Proc Natl Acad Sci U S A Nov. 12, 2002 15228-15233 99.

Gottesman, S. Stealth regulation: biological circuits with small RNA switches Genes Dev Nov. 15, 2002 2829-2842 16.

Calin, G. A., C. D. Dumitru, M. Shimizu, R. Bichi, S. Zupo, E. Noch, H. Aldler, S. Rattan, M. Keating, K. Rai, L. Rassenti, T. Kipps, M. Negrini, F. Bullrich and C. M. Croce. Frequent deletions and downregulation of micro- RNA genes miR15 and miR16 at 13q14 in chronic lymphocytic leukemia Proc Natl Acad Sci U S A Nov. 26, 2002 15524-15529 99.

Gaudilliere, B., Y. Shi and A. Bonni. RNA interference reveals a requirement for myocyte enhancer factor 2A in activity-dependent neuronal survival J Biol Chem Nov. 29, 2002 46442-46446 277.

Jones, L. Revealing micro-RNAs in plants Trends Plant Sci Nov. 2002 473-475 7.

Schauer, S. E., S. E. Jacobsen, D. W. Meinke and A. Ray. Dicer-Like1: blind men and elephants in Arabidopsis development Trends Plant Sci Nov. 2002 487-491 7.

Okazaki, Y., M. Furuno, T. Kasukawa, J. Adachi, H. Bono, S. Kondo, et al. Analysis of the mouse transcriptome based on functional annotation of 60,770 full-length cDNAs Nature Dec. 5, 2002 563-573 420.

Uchida, N., S. Hoshino, H. Imataka, N. Sonenberg and T. Katada. A novel role of the mammalian GSPT/eRF3 associating with poly(A)-binding protein in Cap/Poly(A)-dependent translation J Biol Chem Dec. 27, 2002 50286-50292 277.

Huttenhofer, A., J. Brosius and J. P. Bachellerie. RNomics: identification and function of small, non-messenger RNAs Curr Opin Chem Biol Dec. 2002 835-843 6.

Wood, N. T. Unravelling the molecular basis of viral suppression of PTGS Trends Plant Sci 2002 384 7.

Cohen, O., C. Erb, D. Ginzberg, Y. Pollak, S. Seidman, S. Shoham, R. Yirmiya and H. Soreq. Neuronal overexpression of "readthrough" acetylcholinesterase is associated with antisense-suppressible behavioral impairments Mol Psychiatry * No date in pubmed * 2002 874-885 7.

Mlotshwa, S., O. Voinnet, M. F. Mette, M. Matzke, H. Vaucheret, S. W. Ding, G. Pruss and V. B. Vance. RNA silencing and the mobile silencing signal Plant Cell * No date in pubmed * 2002 S289-301 14 Suppl.

Tang, G., B. J. Reinhart, D. P. Bartel and P. D. Zamore. A biochemical framework for RNA silencing in plants Genes Dev Jan. 1, 2003 49-63 17.

Kawasaki, H. and K. Taira. Short hairpin type of dsRNAs that are controlled by tRNA(Val) promoter significantly induce RNAi-mediated gene silencing in the cytoplasm of human cells Nucleic Acids Res Jan. 15, 2003 700-707 31.

Ashrafi, K., F. Y. Chang, J. L. Watts, A. G. Fraser, R. S. Kamath, J. Ahringer and G. Ruvkun. Genome-wide RNAi analysis of Caenorhabditis elegans fat regulatory genes Nature Jan. 16, 2003 268-272 421.

Kamath, R. S., A. G. Fraser, Y. Dong, G. Poulin, R. Durbin, M. Gotta, A. Kanapin, N. Le Bot, S. Moreno, M. Sohrmann, D. P. Welchman, P. Zipperlen and J. Ahringer. Systematic functional analysis of the Caenorhabditis elegans genome using RNAi Nature Jan. 16, 2003 231-237 421.

Tuschl, T. Functional genomics: RNA sets the standard Nature Jan. 16, 2003 220-221 421.

Iyer, L. M., E. V. Koonin and L. Aravind. Evolutionary connection between the catalytic subunits of DNA-dependent RNA polymerases and eukaryotic RNA-dependent RNA polymerases and the origin of RNA polymerases BMC Struct Biol Jan. 28, 2003 1 3.

Shi, Y. Mammalian RNAi for the masses Trends Genet Jan. 2003 9-12 19.

Cerutti, H. RNA interference: traveling in the cell and gaining functions? Trends Genet Jan. 2003 39-46 19.

Zeng, Y. and B. R. Cullen. Sequence requirements for micro RNA processing and function in human cells Rna Jan. 2003 112-123 9.

Kawasaki, H., E. Suyama, M. Iyo and K. Taira. siRNAs generated by recombinant human Dicer induce specific and significant but target site-independent gene silencing in human cells Nucleic Acids Res Feb. 1, 2003 981-987 31.

Reiner, A., D. Yekutieli and Y. Benjamini. Identifying differentially expressed genes using false discovery rate controlling procedures Bioinformatics Feb. 12, 2003 368-375 19.

Doench, J. G., C. P. Petersen and P. A. Sharp. siRNAs can function as miRNAs Genes Dev Feb. 15, 2003 438-442 17.

Gupta, V., A. Cherkassky, P. Chatis, R. Joseph, A. L. Johnson, J. Broadbent, T. Erickson and J. Dimeo. Directly labeled mRNA produces highly precise and unbiased differential gene expression data Nucleic Acids Res Feb. 15, 2003 e13 31.

Boffelli, D., J. McAuliffe, D. Ovcharenko, K. D. Lewis, I. Ovcharenko, L. Pachter and E. M. Rubin. Phylogenetic shadowing of primate sequences to find functional regions of the human genome Science Feb. 28, 2003 1391-1394 299.

Kasschau, K. D., Z. Xie, E. Allen, C. Llave, E. J. Chapman, K. A. Krizan and J. C. Carrington. P1/HC-Pro, a viral suppressor of RNA silencing, interferes with Arabidopsis development and miRNA unction Dev Cell Feb. 2003 205-217 4.

Carmell, M. A., L. Zhang, D. S. Conklin, G. J. Hannon and T. A. Rosenquist. Germline transmission of RNAi in mice Nat Struct Biol Feb. 2003 91-92 10.

Dostie, J., Z. Mourelatos, M. Yang, A. Sharma and G. Dreyfuss. Numerous microRNPs in neuronal cells containing novel microRNAs Rna Feb. 2003 180-186 9.

Lagos-Quintana, M., R. Rauhut, J. Meyer, A. Borkhardt and T. Tuschl. New microRNAs from mouse and human Rna Feb. 2003 175-179 9.

Wilson, J. A., S. Jayasena, A. Khvorova, S. Sabatinos, I. G. Rodrigue-Gervais, S. Arya, F. Sarangi, M. Harris-Brandts, S. Beaulieu and C. D. Richardson. RNA interference blocks gene expression and RNA synthesis from hepatitis C replicons propagated in human liver cells Proc Natl Acad Sci U S A Mar. 4, 2003 2783-2788 100.

Lim, L. P., M. E. Glasner, S. Yekta, C. B. Burge and D. P. Bartel. Vertebrate microRNA genes Science Mar. 7, 2003 1540 299.

Maniataki, E., A. E. Martinez De Alba, R. Sagesser, M. Tabler and M. Tsagris. Viroid RNA systemic spread may depend on the interaction of a 71-nucleotide bulged hairpin with the host protein VirP1 Rna Mar. 2003 346-354 9.

Ambros, V., B. Bartel, D. P. Bartel, C. B. Burge, J. C. Carrington, X. Chen, G. Dreyfuss, S. R. Eddy, S. Griffiths-Jones, M. Marshall, M. Matzke, G. Ruvkun and T. Tuschl. A uniform system for microRNA annotation Rna Mar. 2003 277-279 9.

Findley, S. D., M. Tamanaha, N. J. Clegg and H. Ruohola-Baker. Maelstrom, a Drosophila spingle-class gene, encodes a protein that colocalizes with Vasa and RDE1/AGO1 homolog, Aubergine, in nuage Development Mar. 2003 859-871 130.

Hershberg, R., S. Altuvia and H. Margalit. A survey of small RNA-encoding genes in *Escherichia coli* Nucleic Acids Res Apr. 1, 2003 1813-1820 31.

Brennecke, J., D. R. Hipfner, A. Stark, R. B. Russell and S. M. Cohen. bantam encodes a developmentally regulated microRNA that controls cell proliferation and regulates the proapoptotic gene hid in Drosophila Cell Apr. 4, 2003 25-36 113.

Lim, L. P., N. C. Lau, E. G. Weinstein, A. Abdelhakim, S. Yekta, M. W. Rhoades, C. B. Burge and D. P. Bartel. The microRNAs of Caenorhabditis elegans Genes Dev Apr. 15, 2003 991-1008 17.

XU, P., S. Y. Vernooy, M. Guo and B. A. Hay. The Drosophila microRNA Mir-14 suppresses cell death and is required for normal fat metabolism Curr Biol Apr. 29, 2003 790-795 13.

Xie, Z., K. D. Kasschau and J. C. Carrington. Negative feedback regulation of Dicer-Like1 in Arabidopsis by microRNA-guided mRNA degradation Curr Biol Apr. 29, 2003 784-789 13.

Carmichael, G. G. Antisense starts making more sense Nat Biotechnol Apr. 2003 371-372 21.

Yelin, R., D. Dahary, R. Sorek, E. Y. Levanon, O. Goldstein, A. Shoshan, A. Diber, S. Biton, Y. Tamir, R. Khosravi, S. Nemzer, E. Pinner, S. Walach, J. Bernstein, K. Savitsky and G. Rotman. Widespread occurrence of antisense transcription in the human genome Nat Biotechnol Apr. 2003 379-386 21.

Boutet, S., F. Vazquez, J. Liu, C. Beclin, M. Fagard, A. Gratias, J. B. Morel, P. Crete, X. Chen and H. Vaucheret. Arabidopsis HEN1: a genetic link between endogenous miRNA controlling development and siRNA controlling transgene silencing and virus resistance Curr Biol May 13, 2003 843-848 13.

Ambros, V., R. C. Lee, A. Lavanway, P. T. Williams and D. Jewell. MicroRNAs and other tiny endogenous RNAs in C. elegans Curr Biol May 13, 2003 807-818 13.

Liang, X. S. J. Q. Lian, Y. X. Zhou, Q. H. Nie and C. Q. Hao. A small yeast RNA inhibits HCV IRES mediated translation and inhibits replication of poliovirus in vivo World J Gastroenterol May 2003 1008-1013 9.

Grad, Y., J. Aach, G. D. Hayes, B. J. Reinhart, G. M. Church, G. Ruvkun and J. Kim. Computational and experimental identification of C. elegans microRNAs Mol Cell May 2003 1253-1263 11.

Abrahante, J. E., A. L. Daul, M. Li, M. L. Volk, J. M. Tennessen, E. A. Miller and A. E. Rougvie. The Caenorhabditis elegans hunchback-like gene lin-57/hbl-1 controls developmental time and is regulated by microRNAs Dev Cell May 2003 625-637 4.

Lin, S. Y., S. M. Johnson, M. Abraham, M. C. Vella, A. Pasquinelli, C. Gamberi, E. Gottlieb and F. J. Slack. The C elegans hunchback homolog, hbl-1, controls temporal patterning and is a probable microRNA target Dev Cell May 2003 639-650 4.

Zamvil, S. S. and L. Steinman. Diverse targets for intervention during inflammatory and neurodegenerative phases of multiple sclerosis Neuron Jun. 5, 2003 685-688 38.

Ambros, V. MicroRNA pathways in flies and worms: growth, death, fat, stress, and timing Cell Jun. 13, 2003 673-676 113.

Moss, E. G. and L. Tang. Conservation of the heterochronic regulator Lin-28, its developmental expression and microRNA complementary sites Dev Biol Jun. 15, 2003 432-442 258.

Smalheiser, N. R. EST analyses predict the existence of a population of chimeric microRNA precursor-mRNA transcripts expressed in normal human and mouse tissues Genome Biol Epub 2003 Jun. 18, 2003 403 4.

Lai, E. C., P. Tomancak, R. W. Williams and G. M. Rubin. Computational identification of Drosophila microRNA genes Genome Biol Epub 2003 Jun. 30, 2003 R42 4.

No author listed. Whither RNAi? Nat Cell Biol Jun. 2003 489-490 5.

Bartel, B. and D. P. Bartel. MicroRNAs: at the root of plant development? Plant Physiol Jun. 2003 709-717 132.

Dykxhoorn, D. M., C. D. Novina and P. A. Sharp. Killing the messenger: short RNAs that silence gene expression Nat Rev Mol Cell Biol Jun. 2003 457-467 4.

Saunders, L. R. and G. N. Barber. The dsRNA binding protein family: critical roles, diverse cellular functions Faseb J Jun. 2003 961-983 17.

Steinman, L. and S. Zamvil. Transcriptional analysis of targets in multiple sclerosis Nat Rev Immunol Jun. 2003 483-492 3.

QI, Y. and B. Ding. Inhibition of cell growth and shoot development by a specific nucleotide sequence in a noncoding viroid RNA Plant Cell Jun. 2003 1360-1374 15.

Jackson, A. L., S. R. Bartz, J. Schelter, S. V. Kobayashi, J. Burchard, M. Mao, B. Li, G. Cavet and P. S. Linsley. Expression profiling reveals off-target gene regulation by RNAi Nat Biotechnol Jun. 2003 635-637 21.

Bashirullah, A., A. E. Pasquinelli, A. A. Kiger, N. Perrimon, G. Ruvkun and C. S. Thummel. Coordinate regulation of small temporal RNAs at the onset of Drosophila metamorphosis Dev Biol Jul. 1, 2003 259.

Sempere, L. F., N. S. Sokol, E. B. Dubrovsky, E. M. Berger and V. Ambros. Temporal regulation of microRNA expression in Drosophila melanogaster mediated by hormonal signals and broad-Complex gene activity. Genome Biol. 5:R13 (2003).

Heetebrij, R. J., E. G. Talman, M. A. V Velzen, R. P. Van Gijlswijk, S. S. Snoeijers, M. Schalk, J. Wiegant, F. V D Rijke, R. M. Kerkhoven, A. K. Raap, H. J. Tanke, J. Reedijk and H. J. Houthoff. Platinum(II)-based coordination compounds as nucleic acid labeling reagents: synthesis, reactivity, and applications in hybridization assays Chembiochem Jul. 7, 2003 573-583 4.

Borodina, T. A., H. Lehrach and A. V. Soldatov. Ligation-based synthesis of oligonucleotides with block structure Anal Biochem Jul. 15, 2003 309-313 318.

Johnson, S. M., S. Y. Lin and F. J. Slack. The time of appearance of the C. elegans let-7 microRNA is transcriptionally controlled utilizing a temporal regulatory element in its promoter Dev Biol Jul. 15, 2003 364-379 259.

Carrington, J. C. and V. Ambros. Role of microRNAs in plant and animal development Science Jul. 18, 2003 336-338 301.

Smale, S. T. The establishment and maintenance of lymphocyte identity through gene silencing Nat Immunol Jul. 2003 607-615 4.

Bridge, A. J., S. Pebernard, A. Ducraux, A. L. Nicoulaz and R. Iggo. Induction of an interferon response by RNAi vectors in mammalian cells Nat Genet Jul. 2003 263-264 34.

Seitz, H., N. Youngson, S. P. Lin, S. Dalbert, M. Paulsen, J. P. Bachellerie, A. C. Ferguson-Smith and J. Cavaille. Imprinted microRNA genes transcribed antisense to a reciprocally imprinted retrotransposon-like gene Nat Genet Jul. 2003 261-262 34.

Zeng, Y., R. Yi and B. R. Cullen. MicroRNAs and small interfering RNAs can inhibit mRNA expression by similar mechanisms Proc Natl Acad Sci U S A Aug. 19, 2003 9779-9784 100.

Schramke, V. and R. Allshire. Hairpin RNAs and retrotransposon LTRs effect RNAi and chromatin-based gene silencing Science Aug. 22, 2003 1069-1074 301.

Wiznerowicz, M. and D. Trono. Conditional suppression of cellular genes: lentivirus vector-mediated drug-inducible RNA interference J Virol Aug. 2003 8957-8961 77.

Lau, N. C. and D. P. Bartel. Censors of the genome Sci Am Aug. 2003 34-41 289.

Houbaviy, H. B., M. F. Murray and P. A. Sharp. Embryonic stem cell-specific MicroRNAs Dev Cell Aug. 2003 351-358 5.

Aravin, A. A., M. Lagos-Quintana, A. Yalcin, M. Zavolan, D. Marks, B. Snyder, T. Gaasterland, J. Meyer and T. Tuschl. The small RNA profile during Drosophila melanogaster development Dev Cell Aug. 2003 337-350 5.

McManus, M. T. MicroRNAs and cancer Semin Cancer Biol Aug. 2003 253-258 13.

Baner, J., A. Isaksson, E. Waldenstrom, J. Jarvius, U. Landegren and M. Nilsson. Parallel gene analysis with allele-specific padlock probes and tag microarrays Nucleic Acids Res Sep. 1, 2003 e103 31.

Boutla, A., C. Delidakis and M. Tabler. Developmental defects by antisense-mediated inactivation of micro-RNAs 2 and 13 in Drosophila and the identification of putative target genes Nucleic Acids Res Sep. 1, 2003 4973-4980 31.

Palatnik, J. F., E. Allen, X. Wu, C. Schommer, R. Schwab, J. C. Carrington and D. Weigel. Control of leaf morphogenesis by microRNAs Nature Sep. 18, 2003 257-263 425.

Klein, R. J. and S. R. Eddy. Rsearch: finding homologs of single structured RNA sequences BMC Bioinformatics Sep. 22, 2003 44 4.

Caudy, A. A., R. F. Ketting, S. M. Hammond, A. M. Denli, A. M. Bathoorn, B. B. Tops, J. M. Silva, M. M. Myers, G. J. Hannon and R. H. Plasterk. A micrococcal nuclease homologue in RNAi effector complexes Nature Sep. 25, 2003 411-414 425.

Lee, Y., C. Ahn, J. Han, H. Choi, J. Kim, J. Yim, J. Lee, P. Provost, O. Radmark, S. Kim and V. N. Kim. The nuclear RNase III Drosha initiates microRNA processing Nature Sep. 25, 2003 415-419 425.

Sledz, C. A., M. Holko, M. J. De Veer, R. H. Silverman and B. R. Williams. Activation of the interferon system by short-interfering RNAs Nat Cell Biol Sep. 2003 834-839 5.

Bergmann, A. and M. E. Lane. HIDden targets of microRNAs for growth control Trends Biochem Sci Sep. 2003 461-463 28.

Khvorova, A., A. Reynolds and S. D. Jayasena. Functional siRNAs and miRNAs exhibit strand bias Cell Oct. 17, 2003 209-216 115.

Schwarz, D. S., G. Hutvagner, T. Du, Z. Xu, N. Aronin and P. D. Zamore. Asymmetry in the assembly of the RNAi enzyme complex Cell Oct. 17, 2003 199-208 115.

Abbott, A. L. Heterochronic genes Curr Biol Oct. 28, 2003 R824-825 13.

Hake, S. MicroRNAs: a role in plant development Curr Biol Oct. 28, 2003 R851-852 13.

Carthew, R. W. Making and breaking with nucleases and small RNAs Nat Struct Biol Oct. 2003 776-777 10.

Krichevsky, A. M., K. S. King, C. P. Donahue, K. Khrapko and K. S. Kosik. A microRNA array reveals extensive regulation of microRNAs during brain development Rna Oct. 2003 1274-1281 9.

Mattick, J. S. Challenging the dogma: the hidden layer of non-protein-coding RNAs in complex organisms Bioessays Oct. 2003 930-939 25.

Nelson, P., M. Kiriakidou, A. Sharma, E. Maniataki and Z. Mourelatos. The microRNA world: small is mighty Trends Biochem Sci Oct. 2003 534-540 28.

Michael, M. Z., O. C. SM, N. G. Van Holst Pellekaan, G. P. Young and R. J. James. Reduced accumulation of specific microRNAs in colorectal neoplasia Mol Cancer Res Oct. 2003 882-891 1.

Allinson, T. M., E. T. Parkin, A. J. Turner and N. M. Hooper. Adams family members as amyloid precursor protein alpha-secretases J Neurosci Res Nov. 1, 2003 342-352 74.

Kawasaki, H. and K. Taira. Retraction: Hes1 is a target of microRNA-23 during retinoic-acid-induced neuronal differentiation of NT2 cells Nature Nov. 6, 2003 100 426.

Saxena, S., Z. O. Jonsson and A. Dutta. Small RNAs with imperfect match to endogenous mRNA repress translation. Implications for off-target activity of small inhibitory RNA in mammalian cells J Biol Chem Nov. 7, 2003 44312-44319 278.

Basyuk, E., F. Suavet, A. Doglio, R. Bordonne and E. Bertrand. Human let-7 stem-loop precursors harbor features of RNase III cleavage products Nucleic Acids Res Nov. 15, 2003 6593-6597 31.

Stevenson, M. Dissecting HIV-1 through RNA interference Nat Rev Immunol Nov. 2003 851-858 3.

Wienholds, E., M. J. Koudijs, F. J. Van Eeden, E. Cuppen and R. H. Plasterk. The microRNA-producing enzyme Dicer1 is essential for zebrafish development Nat Genet Nov. 2003 217-218 35.

Gibbs, W. W. The unseen genome: gems among the junk Sci Am Nov. 2003. 289:48-53.

Chang, J., P. Provost and J. M. Taylor. Resistance of human hepatitis delta virus RNAs to dicer activity J Virol Nov. 2003 11910-11917 77.

Wang, D., A. Urisman, Y. T. Liu, M. Springer, T. G. Ksiazek, D. D. Erdman, E. R. Mardis, M. Hickenbotham, V. Magrini, J. Eldred, J. P.

Latreille, R. K. Wilson, D. Ganem and J. L. Derisi. Viral Discovery and sequence recovery using DNA microarrays PLoS Biol Nov. 2003 E2 1, vol. 1, Issue 2, pp. 257-260.

Aukerman, M. J. and H. Sakai. Regulation of flowering time and floral organ identity by a MicroRNA and its APETALA2-like target genes Plant Cell Nov. 2003 2730-2741 15.

Stein, T. D. and J. A. Johnson. Genetic programming by the proteolytic fragments of the amyloid precursor protein: somewhere between confusion and clarity Rev Neurosci * no date in pubmed * 2003 317-341 14.

Szymanski, M., M. Z. Barciszewska, M. Zywicki and J. Barciszewski. Noncoding RNA transcripts J Appl Genet 2003 1-19 44.

* cited by examiner

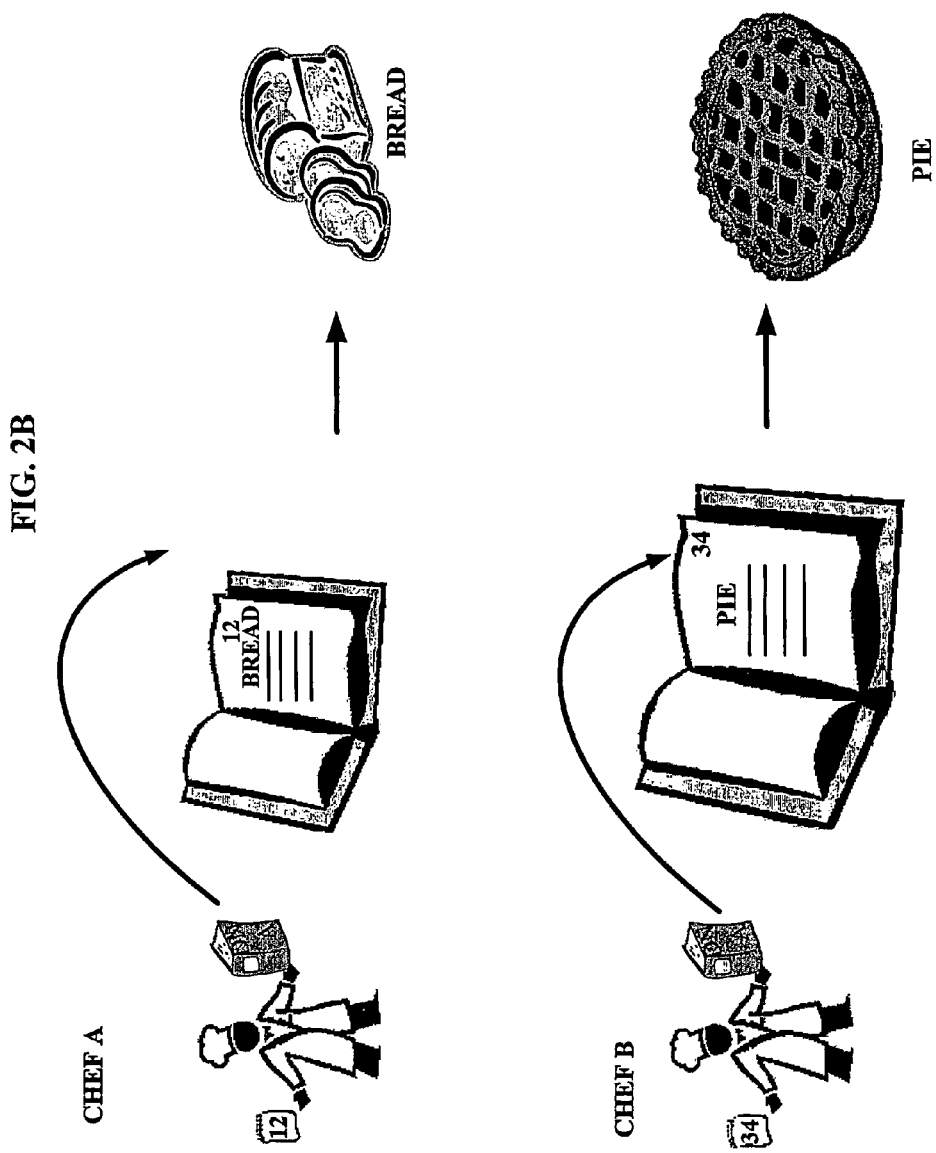

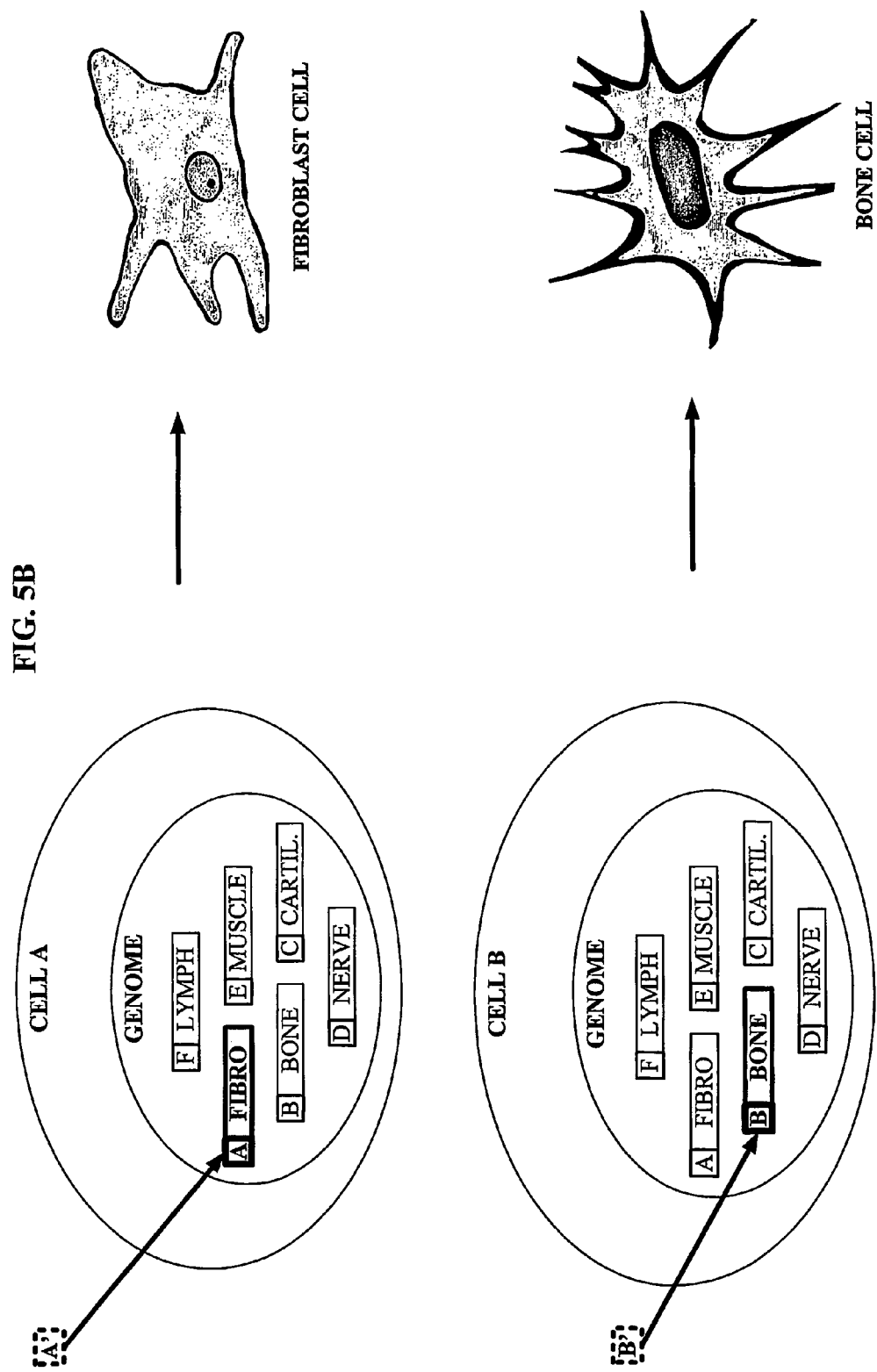

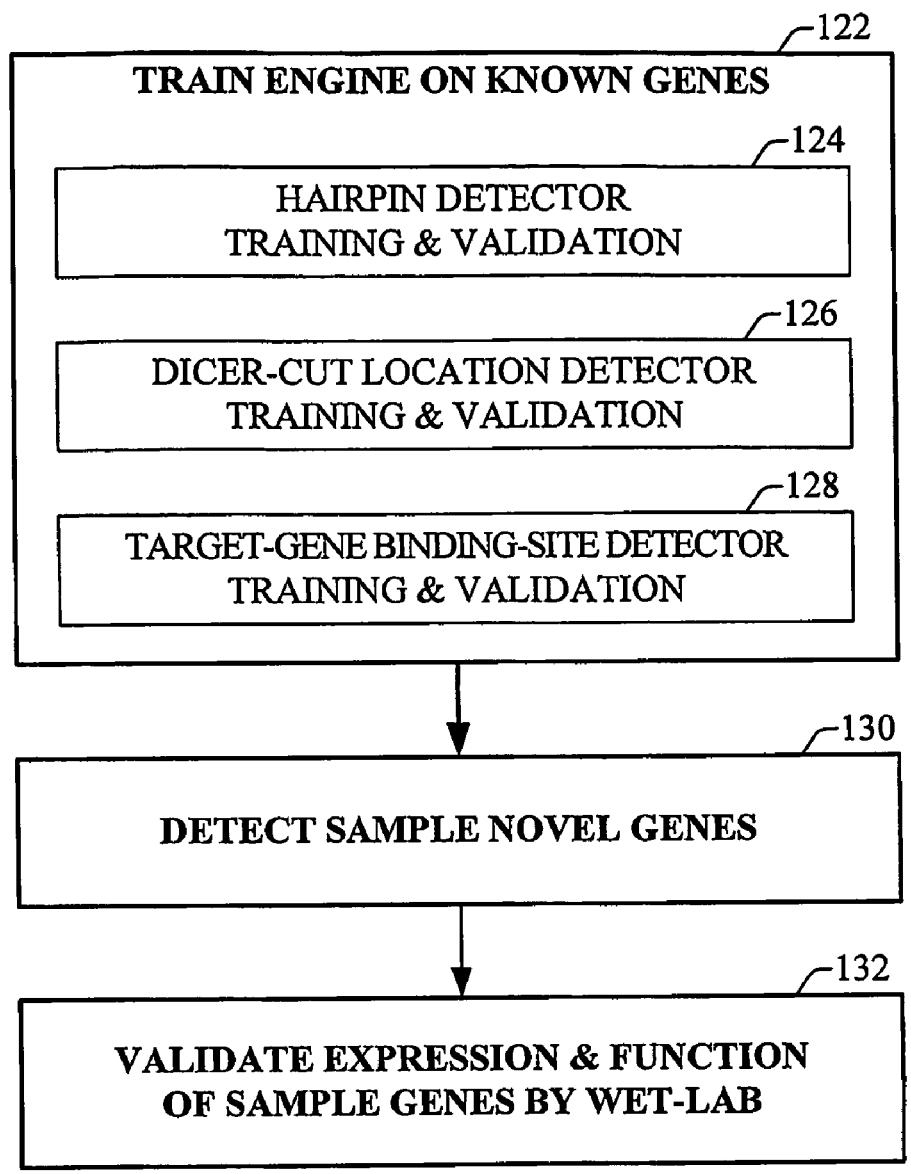

FIG. 21

| Detection Accuracy Group | Number of Published MIRs | Lab Validation | | | Novel GAMs of Present Invention | Hairpins in RNA Database | |
|---|---|---|---|---|---|---|---|
| | | Sent | Positive | % success | | Number | Expected |
| A | 82 | 10 | 5 | 50% | 562 | 564 | 282 |
| B | 146 | 91 | 32 | 35% | 526 | 813 | 285 |
| C | 38 | 30 | 9 | 30% | 625 | 2080 | 624 |
| D | 78 | 16 | 4 | 25% | 3034 | 11512 | 2878 |
| Overall | 344 | 147 | 50 | 34% | 4747 | 14969 | 4069 |

FIG. 24A

EST72223 (705 nt.)

EST72223 sequence:

CCCTTATTAGAGGATTCTGCTCATGCCAGG**GTGAGGTAGTAAGTTGTATTG
TTGTGGGGTAGGGATATTAGGCCCCAATTAGAAGATAACTATACAACT** MIR98
TACTACTTTCCCTGGTGTGTGGCATATTCACACTTAGTCTTAGCAGTGTTGCC
TCCATCAGACAAAGTTGTAGATGTTCCTTGGATAATTTGGACTGGAAGAAAAGA
GACATGGAAGGGGACAGATGGTGTTTAGGGTGAGGCAGATGTCATTATAAAGT
GACTTGTCTTTCATTAATTGGAGCATATAATTATTTTACCTTTGGGCATGAACTC
ATTTTGCTATTCTTCAACTGTGTAATGATTGCATTTTATTAGTAATAGAACAGGA
ATGTGTGCAAGGGAATGGAAAGCATACTTTAAGAATTTTGGGCCAGGCGCGGT
GGTTCATGCCTGTAATCCCAGCATTTTTGGGAGGCCGAGGCGGGTGGATCAC
CTGAGGTCAGGAGTTCGAGACCAACCTGGCCAACACGGCGAAACCCCGCCTC
TACTCAAATACAAAAATTAGCCAGGCTTGGTGACACTCGCCTGTGGTCCCAGC
TACTCAGGAGGCTGAGGCAGGAGAATTGCTTGAACCCAGGAAGTGGAG GAM25
**GCTTCAGTGAGCTGAGAACACGCCACTGCACTCCAGTCCTGGGCAAC
AGAGCAAGACTCTGTCTC**AGGAAAAAAAAAG

MICRORNA-RELATED NUCLEIC ACIDS AND USES THEREOF

CROSS-REFERENCE TO RELATED APPLICATIONS

This is the national stage of International Application. No. PCT/IL03/00970, filed Nov. 16, 2003, which is a continuation-in-part of U.S. patent application Ser. Nos. 10/604,727, filed Aug. 13, 2003; 10/604,985, filed Aug. 29, 2003; 10/604,926, filed Aug. 27, 2003; 10/605,923, filed Nov. 6, 2003; and 10/605,924, filed Nov. 6, 2003. U.S. patent application Ser. No. 10/604,727 is a continuation of U.S. patent application Ser. No. 10/604,726, filed Aug. 13, 2003, which is a continuation of U.S. patent application Ser. No. 10/293,338, filed Nov. 14, 2002. U.S. patent application Ser. No. 10/604,985 claims the benefit of U.S. Provisional Application Ser. No. 60/468,251, filed May 7, 2003. U.S. patent application Ser. No. 10/604,926 is a continuation of U.S. patent application Ser. No. 10/345,201, filed Jan. 16, 2003. U.S. patent application Ser. No. 10/605,923 is a continuation of U.S. patent application Ser. No. 10/649,653, filed Aug. 28, 2003, which is a continuation of U.S. patent application Ser. No. 10/321,503, filed Dec. 18, 2002. U.S. patent application Ser. No. 10/605,924 is a continuation of U.S. patent application Ser. No. 10/651,227, filed Aug. 29, 2003, which is a continuation of U.S. patent application Ser. No. 10/310,914, filed Dec. 6, 2002 and issued as U.S. Pat. No. 7,250,496 on Jul. 31, 2007. The contents of the aforementioned applications are incorporated herein by reference.

FIELD OF THE INVENTION

The present invention relates to a group of bioinformatically detectable novel genes, here identified as Genomic Address Messenger or GAM genes, which are believed to be related to the micro RNA (miRNA) group of genes.

BACKGROUND OF THE INVENTION

MIR genes are regulatory genes encoding MicroRNA's (miRNA), short ~22 nt non-coding RNA's, found in a wide range of species, believed to function as specific gene translation repressors, sometimes involved in cell-differentiation. Some 110 human MIR genes have been detected by laboratory means. Over the past 6 months, the need for computerized detection of MIR genes has been recognized, and several informatic detection engines have been reported (Lim, 2003; Grad, 2003; Lai, 2003). Collectively these informatic detection engines found 38 more human MIR genes which were later confirmed in zebrafish, 14 human MIRs which were confirmed in human, and 55 postulated human MIRs which could not be confirmed by laboratory (Lim, 2003). Extensive efforts to identify novel MIR genes using conventional biological detection techniques such as massive cloning and sequencing efforts, and several bioinformatic detection attempts, have led leading researchers in the field to the conclusion that the total number of human MIR genes is between 200 to 255 (Lau, 2003; Lim 2003 Science; Lim, 2003 Genes Dev). Recent studies postulate that the number of MIR genes may be higher (Grad, 2003; Krichevsky, 2003).

The ability to detect novel MIR genes is limited by the methodologies used to detect such genes. All MIR genes identified so far either present a visibly discernable whole body phenotype, as do Lin-4 and Let-7 (Wightman, 1993; Reinhart, 2000), or produce sufficient quantities of RNA so as to be detected by the standard molecular biological techniques.

Initial studies reporting MIR genes (Bartel, 2001; Tuschl, 2001) discovered 93 MIR genes in several species, by sequencing a limited number of clones (300 by Bartel and 100 by Tuschl) of small segments (i.e. size fractionated) RNA. MiRNA encoded by MIR genes detected in these studies therefore, represent the more prevalent among the miRNA gene family, and can not be much rarer than 1% of all small ~20 nt-long RNA segments.

Current methodology has therefore been unable to detect micro RNA genes (MIR genes) which either do not present a visually discernable whole body phenotype, or are rare (e.g. rarer than 0.1% of all size fractionated ~20 nt-long RNA segments expressed in the tissues examined), and therefore do not produce significant enough quantities of RNA so as to be detected by standard biological techniques.

BRIEF DESCRIPTION OF SEQUENCE LISTING, LARGE TABLES AND COMPUTER PROGRAM LISTING

Sequence listing, large tables related to sequence listing, and computer program listing are filed under section 801 (a)(i) on an electronic medium in computer readable form, attached to the present invention, and are hereby incorporated by reference. Said sequence listing, large tables related to sequence listing, and computer program listing are submitted on a CD-ROM (Operating system: MS-Windows), entitled SEQUENCE LISTING AND LARGE TABLES, containing files the names and sizes of which are as follows:

A sequence listing comprising 548,185 genomic sequences, is filed herewith on electronic medium in computer readable form, attached to the present invention, and is hereby incorporated by reference. Said sequence listing is contained in the file named "Patent12_Human_PCT_PatentIn_2.txt" (79,123 KB), which was created on Dec. 31, 2008.

Large tables relating to genomic sequences are stored in 7 self extracting files, each comprising a respective one of the following table files: TABLE1.TXT (839 KB); TABLE2.TXT (4348 KB); TABLE3.TXT (715 KB); TABLE4.TXT (545728 KB); TABLE5.TXT (1523981 KB); TABLE6.TXT (373091 KB); and TABLE7.TXT (125 KB).

Computer program listing of a computer program constructed and operative in accordance with a preferred embodiment of the present invention is enclosed on an electronic medium in computer readable form, and is hereby incorporated by reference. The computer program listing is contained in a self extracting compressed file named COMPUTER PROGRAM LISTING.EXE (168 KB). Compressed file contains 5 files, the name and sizes of which are as follows: AUXILARY_FILES.TXT (117K); BINDING_SITE_SCORING.TXT (17K); EDIT_DISTANCE.TXT (144K); FIRST-K.TXT (96K); HAIRPIN_PREDICTIO.TXT (47K); and TWO_PHASED_PREDICTOR.TXT (74K).

SUMMARY OF THE INVENTION

The present invention relates to a novel group of regulatory, non-protein coding genes, which are functional in specifically inhibiting translation of target proteins. Each gene in this novel group of genes, here identified as GAM or Genomic Address Messengers, specifically inhibits translation of one of more other 'target' genes by means of complementary hybridization of a segment of the RNA transcript encoded by GAM, to an inhibitor site located in an untranslated region (UTR) of the mRNA of the one or more 'target' genes.

In various preferred embodiments, the present invention seeks to provide improved method and system for specific modulation of expression of specific known 'target' genes involved in significant human diseases, and improved method and system for detection of expression of novel genes of the present invention, which modulate these target genes.

Accordingly, the invention provides several substantially pure DNAs (e.g., genomic DNA, cDNA or synthetic DNA) each encoding a novel gene of the GAM group of gene, vectors comprising the DNAs, probes comprising the DNAs, a method and system for selectively modulating translation of known 'target' genes utilizing the vectors, and a method and system for detecting expression of known 'target' genes utilizing the probe.

By "substantially pure DNA" is meant DNA that is free of the genes which, in the naturally-occurring genome of the organism from which the DNA of the invention is derived, flank the genes discovered and isolated by the present invention. The term therefore includes, for example, a recombinant DNA which is incorporated into a vector, into an autonomously replicating plasmid or virus, or into the genomic DNA of a prokaryote or eukaryote at a site other than its natural site; or which exists as a separate molecule (e.g., a cDNA or a genomic or cDNA fragment produced by PCR or restriction endonuclease digestion) independent of other sequences. It also includes a recombinant DNA which is part of a hybrid gene encoding additional polypeptide sequence.

"Inhibiting translation" is defined as the ability to prevent synthesis of a specific protein encoded by a respective gene, by means of inhibiting the translation of the mRNA of this gene. "Translation inhibitor site" is defined as the minimal DNA sequence sufficient to inhibit translation.

There is thus provided in accordance with a preferred embodiment of the present invention a bioinformatically detectable novel gene encoding substantially pure DNA wherein RNA encoded by the bioinformatically detectable novel gene is about 18 to about 24 nucleotides in length, and originates from an RNA precursor, which RNA precursor is about 50 to about 120 nucleotides in length, a nucleotide sequence of a first half of the RNA precursor is a partial or accurate inversed reversed sequence of a nucleotide sequence of a second half thereof, a nucleotide sequence of the RNA encoded by the novel gene is a partial or accurate inversed reversed sequence of a nucleotide sequence of a binding site associated with at least one target gene, the novel gene cannot be detected by either of the following: a visually discernable whole body phenotype, and detection of 99.9% of RNA species shorter than 25 nucleotides expressed in a tissue sample, and a function of the novel gene is bioinformatically deducible.

There is still further provided in accordance with another preferred embodiment of the present invention a bioinformatically detectable novel gene encoding substantially pure DNA wherein RNA encoded by the bioinformatically detectable novel gene includes a plurality of RNA sections, each of the RNA sections being about 50 to about 120 nucleotides in length, and including an RNA segment, which RNA segment is about 18 to about 24 nucleotides in length, a nucleotide sequence of a first half of each of the RNA sections encoded by the novel gene is a partial or accurate inversed reversed sequence of nucleotide sequence of a second half thereof, a nucleotide sequence of each of the RNA segments encoded by the novel gene is a partial or accurate inversed reversed sequence of the nucleotide sequence of a binding site associated with at least one target gene, and a function of the novel gene is bioinformatically deducible from the following data elements: the nucleotide sequence of the RNA encoded by the novel gene, a nucleotide sequence of the at least one target gene, and function of the at least one target gene.

There is additionally provided in accordance with another preferred embodiment of the present invention a bioinformatically detectable novel gene encoding substantially pure DNA wherein RNA encoded by the bioinformatically detectable novel gene is about 18 to about 24 nucleotides in length, and originates from an RNA precursor, which RNA precursor is about 50 to about 120 nucleotides in length, a nucleotide sequence of a first half of the RNA precursor is a partial or accurate inversed reversed sequence of a nucleotide sequence of a second half thereof, a nucleotide sequence of the RNA encoded by the novel gene is a partial or accurate inversed reversed sequence of a nucleotide sequence of a binding site associated with at least one target gene, a function of the novel gene is modulation of expression of the at least one target gene, and the at least one target gene does not encode a protein.

There is moreover provided in accordance with another preferred embodiment of the present invention a bioinformatically detectable novel gene encoding substantially pure DNA wherein the bioinformatically detectable novel gene does not encode a protein, RNA encoded by the bioinformatically detectable novel gene is maternally transferred by a cell to at least one daughter cell of the cell, a function of the novel gene includes modulation of a cell type of the daughter cell, and the modulation is bioinformatically deducible.

There is further provided in accordance with another preferred embodiment of the present invention a bioinformatically detectable novel gene encoding substantially pure DNA wherein the bioinformatically detectable novel gene does not encode a protein, a function of the novel gene is promotion of expression of the at lease one target gene, and the at least one target gene is bioinformatically deducible.

Still further in accordance with a preferred embodiment of the present invention the function of the novel gene is bioinformatically deducible from the following data elements: the nucleotide sequence of the RNA encoded by the bioinformatically detectable novel gene, a nucleotide sequence of the at least one target gene, and a function of the at least one target gene.

Additionally in accordance with a preferred embodiment of the present invention the RNA encoded by the novel gene complementarily binds the binding site associated with the at least one target gene, thereby modulating expression of the at least one target gene.

Moreover in accordance with a preferred embodiment of the present invention the binding site associated with at least one target gene is located in an untranslated region of RNA encoded by the at least one target gene.

Further in accordance with a preferred embodiment of the present invention the function of the novel gene is selective inhibition of translation of the at least one target gene, which selective inhibition includes complementary hybridization of the RNA encoded by the novel gene to the binding site.

Still further in accordance with a preferred embodiment of the present invention, the present invention includes a vector including the DNA Additionally in accordance with a preferred embodiment of the present invention, the present invention includes a method of selectively inhibiting translation of at least one gene, including introducing the vector into a cell.

Moreover in accordance with a preferred embodiment of the present invention the introducing includes utilizing RNAi pathway.

Further in accordance with a preferred embodiment of the present invention, the present invention includes a gene expression inhibition system including: the vector and a vector inserter, functional to insert the vector of claim 10 into a cell, thereby selectively inhibiting translation of at least one gene.

Still further in accordance with a preferred embodiment of the present invention, the present invention includes a probe including the DNA Additionally in accordance with a preferred embodiment of the present invention, the present invention includes a method of selectively detecting expression of at least one gene, including using the probe Moreover in accordance with a preferred embodiment of the present invention, the present invention includes a gene expression detection system including: the probe, and a gene expression detector functional to selectively detect expression of at least one gene.

BRIEF DESCRIPTION OF DRAWINGS

FIGS. 2, 3, and 4 are schematic diagrams which when taken together provide an analogy that illustrates a conceptual model of the present invention, addressing the genomic differentiation engine. FIG. 2B depicts an analogy for differential gene expression between cells.

FIGS. 5A and 5B are schematic diagrams, which when taken together illustrate a 'genomic records' concept of the conceptual model of the present invention, addressing the genomic differentiation enigma;

FIG. 10 is a simplified flowchart illustrating operation of a mechanism for training of a computer system to recognize the novel genes of the present invention, which mechanism is constructed and operative in accordance with a preferred embodiment of the present invention;

FIG. 21 is a table summarizing laboratory validation results which validate efficacy of a bioinformatic gene detection system constructed and operative in accordance with a preferred embodiment of the present invention;

FIG. 24A is an annotated sequence of EST72223 (SEQ ID NO: 548181) comprising known miRNA gene MIR98 and novel gene GAM25, both detected by the gene detection system of the present invention. The sequence of EST 72223 includes the four marked sequences: The sequence of the miRNA-98 hairpin in bold (SEQ ID NO: 548182), the sequence of the mature miRNA-98 in bold and underlined (SEQ ID NO: 548183), the sequence of the GAM25 hairpin in bold (SEQ ID NO: 548184) and the sequence of the mature miRNA of GAM25 in bold and underlined (SEQ ID NO: 548185).

DETAILED DESCRIPTION OF DRAWINGS

Figure 1:
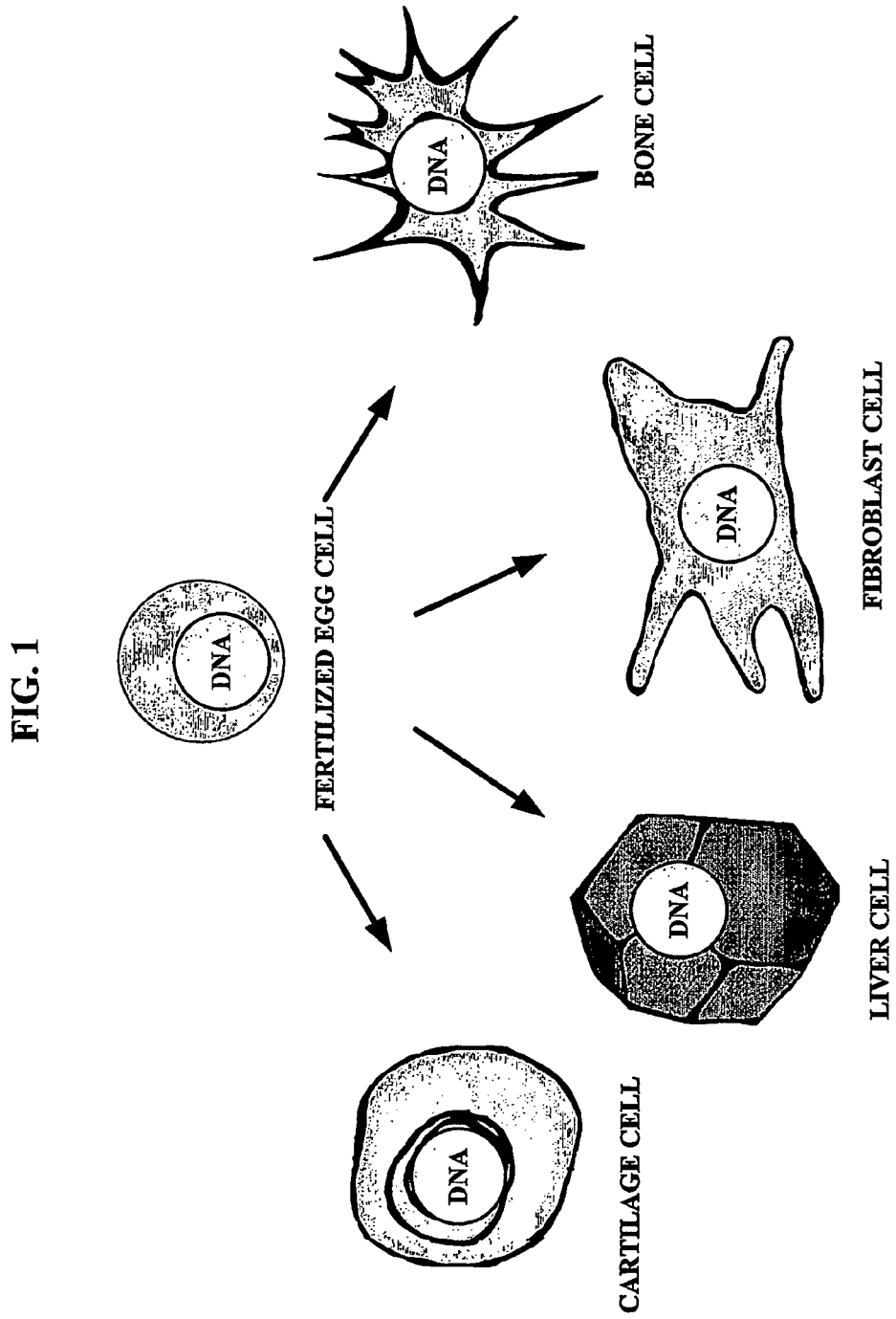
FIG. 1 is a simplified diagram illustrating the genomic differentiation enigma that the present invention addresses.

Reference is now made to FIG. 1 which is a simplified diagram providing a conceptual explanation of a genomic differentiation enigma, which the present invention addresses.

FIG. 1 depicts different cell types in an organism, such as CARTILAGE CELL, LIVER CELL, FIBROBLAST CELL and BONE CELL all containing identical DNA, and deriving from the initial FERTILIZED EGG CELL, and yet each of these cells expressing different proteins, and hence acquiring different shape and function.

The present invention proposes that the inevitable conclusion from this constraint is, however, strikingly simple: the coding system used must be modular. It must comprise multiple modules, or records, one for each cell-type, and a mechanism whereby each cell at its inception is instructed which record to open, and behaves according to instructions in that record.

This modular code concept is somewhat difficult to grasp, since we are strongly habituated to viewing things from an external viewpoint. An architect, for example, looks at a blueprint of a building, which details exactly where each element (block, window, door, electrical switch, etc.) is to be placed relative to all other elements, and then instructs builders to place these elements in their designated places. This is an external viewpoint: the architect is external to the blueprint, which itself is external to the physical building, and its different elements. The architect may therefore act as an 'external organizing agent': seeing the full picture and the relationships between all elements, and being able to instruct from the outside where to place each of them.

Genomics differentiation coding evidently works differently, without any such external organizing agent: It comprises only one smart block (the first cell), which is the architect and the blueprint, and which continuously duplicates itself, somehow knowing when to manifest itself as a block and when as a window, door, or electrical switch.

Figure 2A:
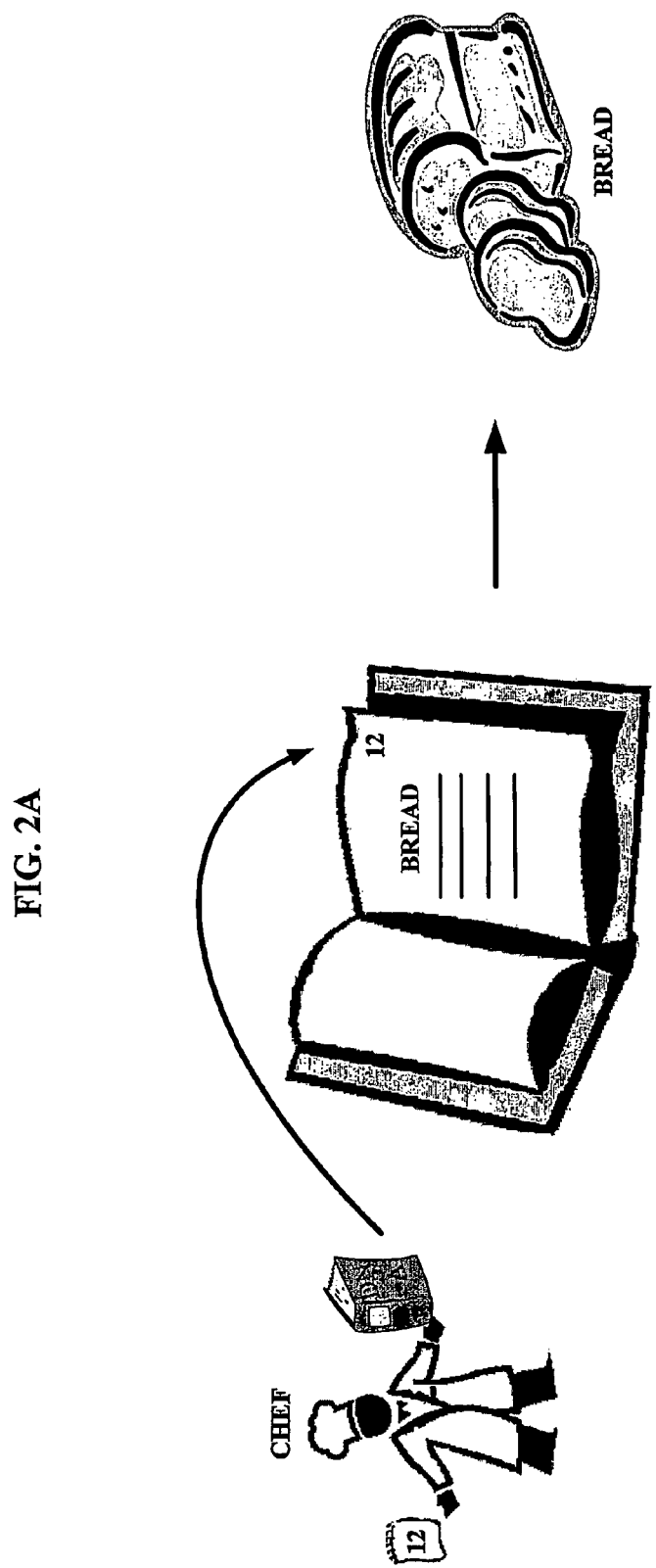
FIG. 2A depicts an analogy for gene expression.
Figure 3:
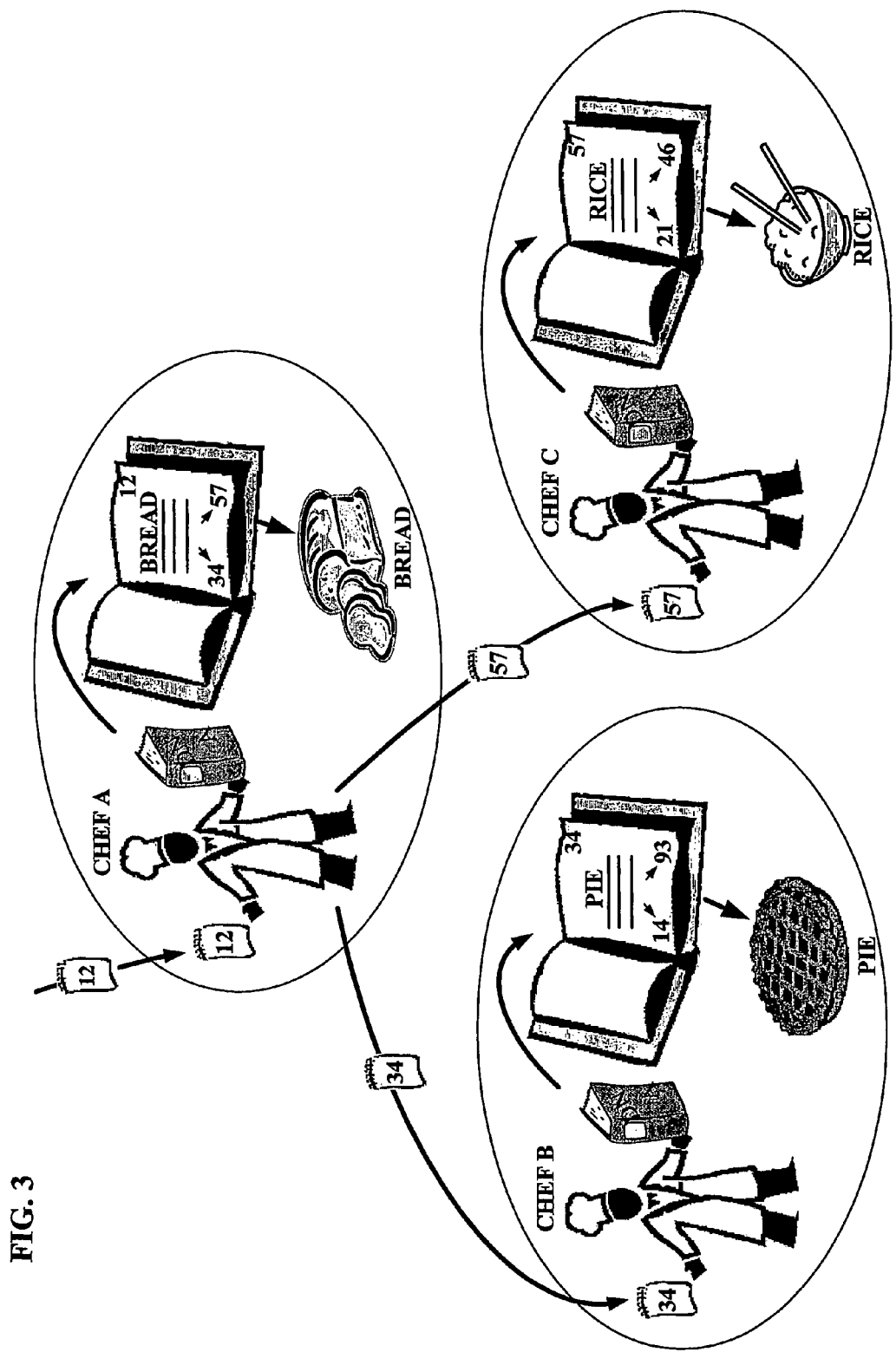
Figure 4:
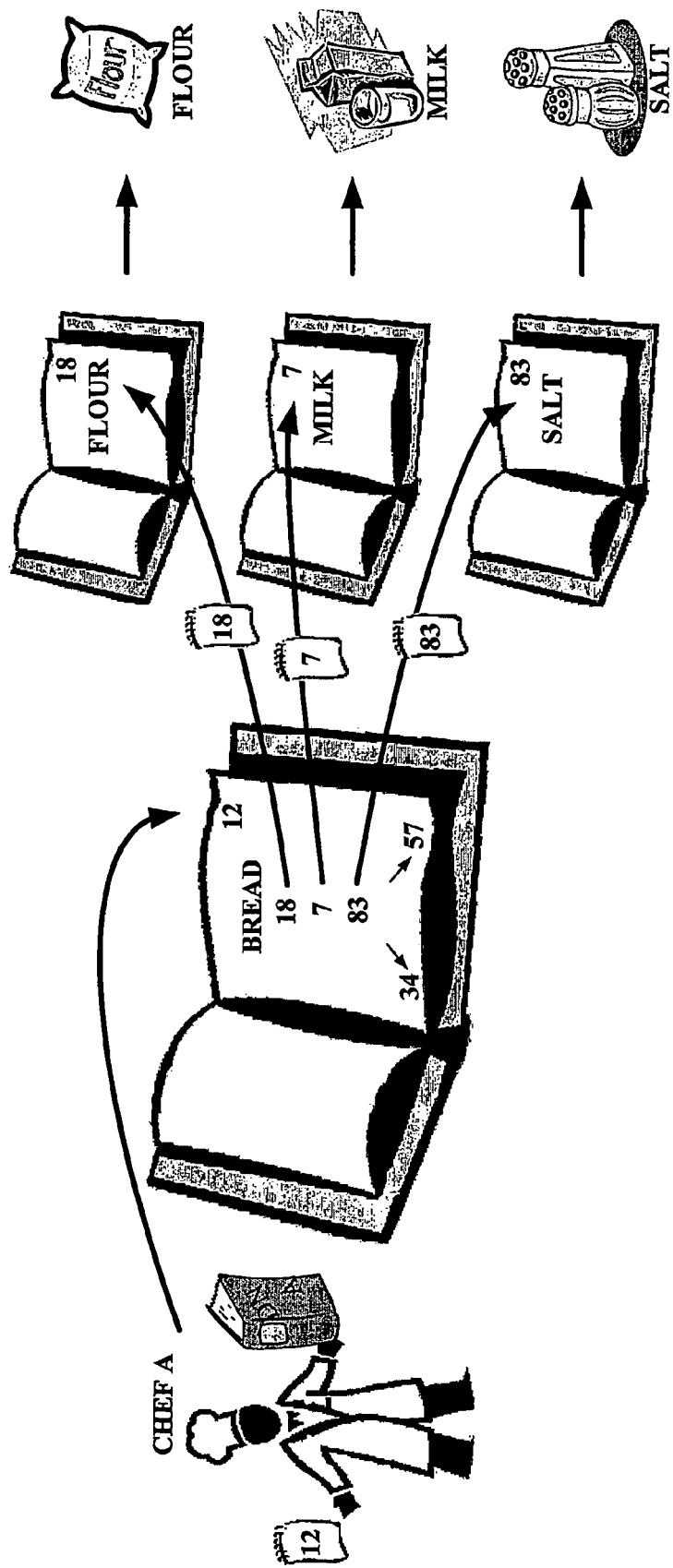

Reference is now made to FIGS. 2 through 4 which are schematic diagrams which when taken together provide an analogy that illustrates a conceptual model of the present invention, addressing the genomic differentiation enigma.

Reference is now made to FIG. 2A. Imagine a very talented chef, capable of preparing any meal provided he is given specific written cooking instructions. This chef is equipped with two items: (a) a thick recipe book, and (b) a small note with a number scribbled on it. The book comprises multiple pages, each page detailing how to prepare a specific meal. The small note indicates the page to be opened, and therefore the meal to be prepared. The chef looks at the page-number written on the note, opens the recipe book at the appropriate page, and prepares the meal according to the written instructions on this page. As an example, FIG. 2A depicts a CHEF holding a note with the number 12 written on it, he opens the book on page 12, and since that page contains the recipe for preparing BREAD, the CHEF prepares a loaf of BREAD.

Reference is now made to FIG. 2B, which depicts two identical chefs, CHEF A and CHEF B, holding an identical recipe book. Despite their identity, and the identity of their recipe book, since CHEF A holds a note numbered 12, and therefore opens the book on page 12 and prepares BREAD, whereas CHEF B holds a note numbered 34 and therefore opens the book on page 34 and prepares a PIE.

Reference is now made to FIG. 3. Imagine the chef of the analogy is also capable of duplicating himself once he has finished preparing the specified meal. The format of the book is such that at the bottom of each page, two numbers are written. When he has finished preparing the meal specified on that page, the chef is trained to do the following: (i) divide himself into two identical duplicate chefs, (ii) duplicate the recipe book and hand a copy to each of his duplicate chefs, and (iii) write down the two numbers found at the bottom of the page of the meal he prepared, on two small notes, handing one note to each of his two duplicate chefs.

Each of the two resulting duplicate chefs are now equipped with the same book, and have the same talent to prepare any meal, but since each of them received a different note, they will now prepare different meals.

FIG. 3 depicts CHEF A holding a recipe book and receiving a note numbered 12. CHEF A therefore opens the book on page 12 and prepares BREAD. When he is finished making bread, CHEF A performs the following actions: (i) divides himself into two duplicate chefs, designated CHEF B and CHEF C, (ii) duplicates his recipe book handing a copy to each of CHEF B and CHEF C, (iii) writes down the numbers found at the bottom of page 12, numbers 34 and 57, on two notes, handing note numbered 34 to CHEF B and note numbered 57 to CHEF C.

Accordingly, CHEF B receives a note numbered 34 and therefore opens the recipe book on page 34 and prepares PIE, whereas CHEF C receives a note numbered 57 and therefore opens the book on page 57 and therefore prepares RICE.

It is appreciated that while CHEF A, CHEF B & CHEF C are identical and hold identical recipe books, they each prepare a different meal. It is also appreciated that the meals prepared by CHEF B and CHEF C are determined CHEF A, and are mediated by the differently numbered notes passed on from CHEF A to CHEF B and CHEF C.

It is further appreciated that the mechanism illustrated by FIG. 3 enables an unlimited lineage of chefs to divide into duplicate, identical chefs and to determine the meals those duplicate chefs would prepare. For example, having been directed to page 34, when CHEF B divides into duplicate chefs (not shown), he will instruct its two duplicate chefs to prepare meals specified on pages 14 and 93 respectively, according to the numbers at the bottom of page 34 to which he was directed. Similarly, CHEF C will instruct its duplicate chefs to prepare meals specified on pages 21 and 46 respectively, etc.

Reference is now made to FIG. 4. Imagine that the cooking instructions on each page of the recipe book are written in shorthand format: The main meal-page to which the chef was directed by the scribbled note, merely contains a list of numbers which direct him to multiple successive pages, each specifying how to prepare an ingredient of that meal.

As an example, FIG. 4 depicts CHEF A of FIGS. 2 and 3, holding a recipe book and a note numbered 12. Accordingly, CHEF A opens the recipe book on page 12, which details the instructions for preparing BREAD. However, the 'instructions' on making BREAD found on page 12 comprise only of 3 numbers, 18, 7 and 83, which 'refer' CHEF A to pages detailing preparation of the ingredients of BREAD—FLOUR, MILK and SALT, respectively.

As illustrated in FIG. 4, turning from the main 'meal page' (e.g. 12) to respective 'ingredients pages' (e.g. pages 18, 7 & 83) is mediated by scribbled notes with the page-numbers written on them. In this analogy, the scribbled notes are required for seeking the target pages to be turned to—both when turning to main 'meal pages' (e.g. page 12), as well as when turning to 'ingredient pages' (e.g. pages 18, 7 & 83).

The chef in the given analogy, schematically depicted in FIGS. 2 through 4, represents a cell; the thick recipe book represents the DNA; preparing a meal in the given analogy represents the cell manifesting itself as a specific cell-type; and ingredients of a meal represent proteins expressed by that cell-type. Like the chef equipped with the thick recipe book in the given analogy, all cells in an organism contain the same DNA and are therefore each potentially capable of manifesting itself as any cell-type, expressing proteins typical of that cell type.

Figure 5A:
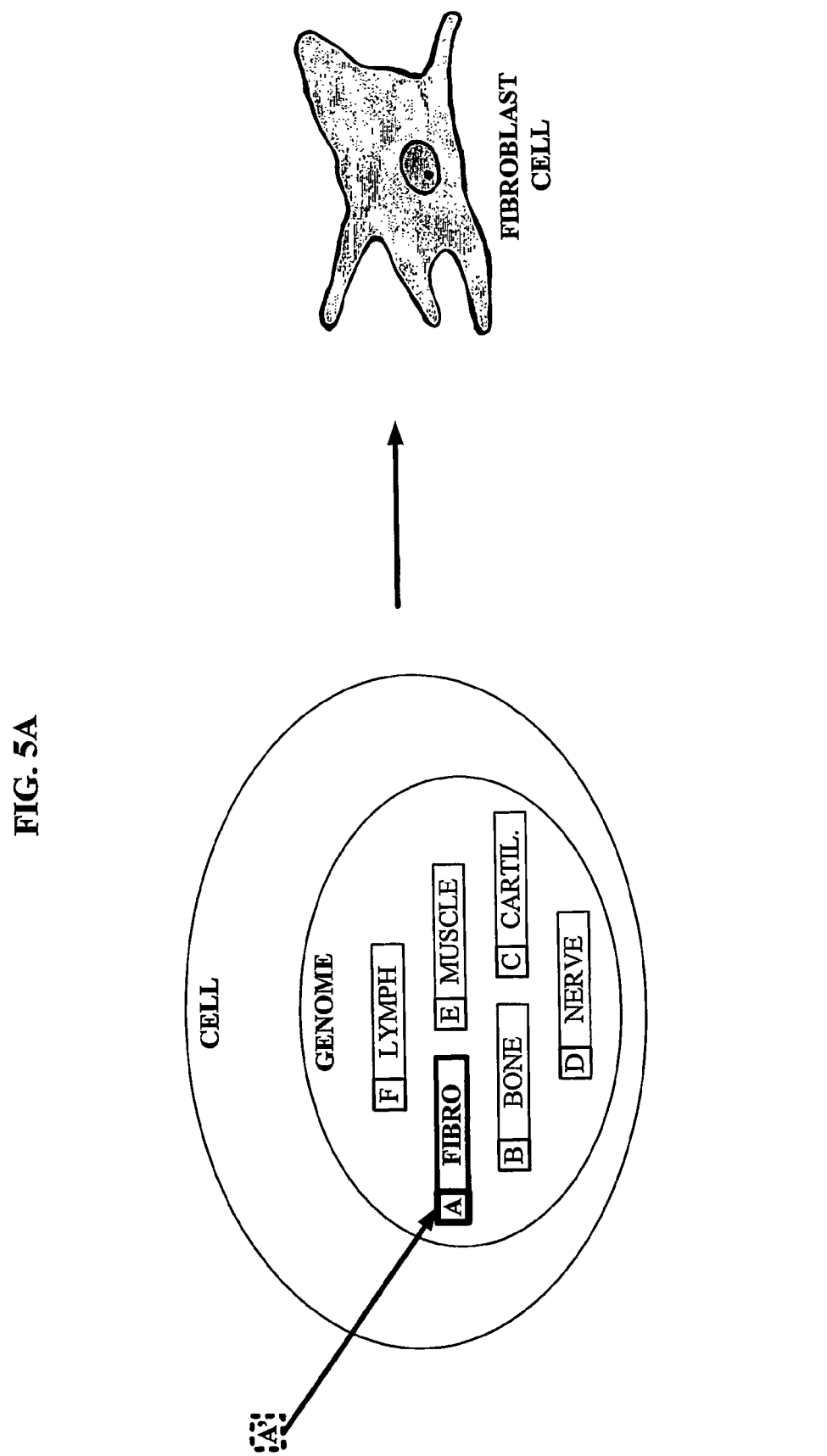

Reference is now made to FIGS. 5A and 5B which are schematic diagrams, which when taken together illustrate a 'genomic records' concept of the conceptual model of the present invention, addressing the genomic differentiation enigma.

The Genomic Records concept asserts that the DNA (the thick recipe book in the illustration) comprises a very large number of Genomic Records (analogous to pages in the recipe book), each containing the instructions for differentiation of a different cell-type, or developmental process. Each Genomic Record is headed by a very short genomic sequence which functions as a 'Genomic Address' of that Genomic Record (analogous to the page number in the recipe book). At its inception, in addition to the DNA, each cell also receives a short RNA segment (the scribbled note in the illustration). This short RNA segment binds complementarily to a 'Genomic Address' sequence of one of the Genomic Records, thereby activating that Genomic Record, and accordingly determining the cell's-fate (analogous to opening the book on the page corresponding to the number on the scribbled note, thereby determining the meal to be prepared).

Reference is now made to FIG. 5A. FIG. 5A illustrates a CELL which comprises a GENOME. The GENOME comprises a plurality of GENOMIC RECORDS, each of which correlates to a specific cell type (for clarity only 6 sample genomic records are shown). Each genomic record comprises genomic instructions on differentiation into a specific cell-type, as further elaborated below with reference to FIG. 7. At cell inception, the CELL receives a maternal short RNA segment, which activates one of the GENOMIC RECORDS, causing the cell to differentiate according to the instructions comprised in that genomic record. As an example, FIG. 5A illustrates reception of a maternal short RNA segment designated A' and outlined by a broken line, which activates the FIBRO genomic record, causing the cell to differentiate into a FIBROBLAST CELL.

Reference is now made to FIG. 5B, which is a simplified schematic diagram, illustrating cellular differentiation mediated by the 'Genomic Records' concept. FIG. 5B depicts 2 cells in an organism, designated CELL A and CELL B, each having a GENOME. It is appreciated that since CELL A and CELL B are cells in the same organism, the GENOME of CELL A is identical to that of CELL B. Despite having an identical GENOME, CELL A differentiates differently from CELL B, due to activation of different genomic records in these two cells. In CELL A the FIBRO GENOMIC RECORD is activated, causing CELL A to differentiate into a FIBROBLAST CELL, whereas in CELL B the BONE GENOMIC RECORD is activated, causing the CELL B to differentiate into a BONE CELL. The cause for activation of different genomic records in these two cells is the different maternal short RNA which they both received: CELL A received a maternal short RNA segment designated A' which activated genomic record FIBRO, whereas CELL B received a maternal short RNA segment designated B' which activated genomic record BONE.

Figure 6:
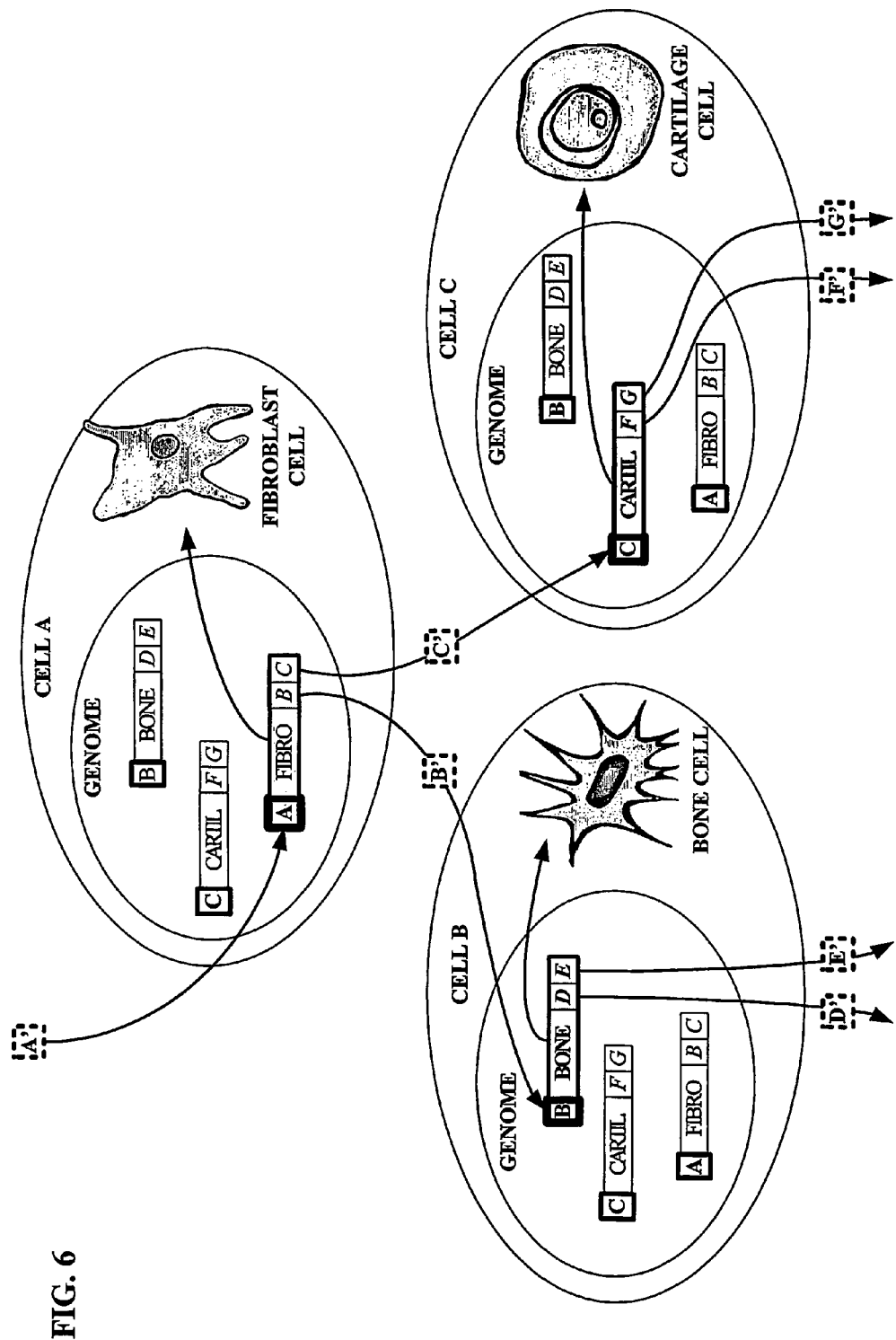
FIG. 6 is a schematic diagram illustrating a 'genomically programmed cell differentiation' concept of the conceptual model of the present invention, addressing the genomic differentiation enigma.

Reference is now made to FIG. 6 which is a schematic diagram illustrating a 'genomically programmed cell differentiation' concept of the conceptual model of the present invention, addressing the genomic differentiation enigma.

A cell designated CELL A divides into 2 cells designated CELL B and CELL C. CELL A, CELL B and CELL C each comprise a GENOME, which GENOME comprises a plurality of GENOMIC RECORDS. It is appreciated that since CELL A, CELL B and CELL C are cells in the same organism, the GENOME of these cells, and the GENOMIC RECORDS comprised therein, are identical.

As described above with reference to FIG. 5B, at its inception, CELL A receives a maternal short RNA segment, designated A' and marked by a broken line, which activates the FIBRO genomic record, thereby causing CELL A to differentiate into a FIBROBLAST CELL. However, FIG. 6 shows further details of the genomic records: each cell genomic record also comprises two short genomic sequences, referred to here as Daughter Cell Genomic Addresses. Blocks designated B and C are Daughter Cell Genomic Addresses of the FIBRO Genomic Record. At cell division, each parent cell transcribes two short RNA segments, corresponding to the two Daughter Cell Genomic Addresses of the Genomic Record of that parent cell, and transfers one to each of its two daughter cells. CELL A of FIG. 6 transcribes and transfers to its two respective daughter cells, two short RNA segments, outlined by a broken line and designated B' and C', corresponding to daughter cell genomic addresses designated B and C comprised in the FIBRO genomic record.

CELL B therefore receives the above mentioned maternal short RNA segment designated B', which binds complementarily to genomic address designated B of genomic record BONE, thereby activating this genomic record, which in turn causes CELL B to differentiate into a BONE CELL. Similarly, CELL C receives the above mentioned maternal short RNA segment designated C', which binds complementarily to genomic address designated C of genomic record CARTIL., thereby activating this genomic record, which in turn causes CELL C to differentiate into a CARTILAGE CELL.

It is appreciated that the mechanism illustrated by FIG. 6 enables an unlimited lineage of cells to divide into daughter cells containing the same DNA, and to determine the cell-fate of these daughter cells. For example, when CELL B and CELL C divide into their respective daughter cells (not shown), they will transfer short RNA segments designated D' & E', and F' & G' respectively, to their respective daughter cells. The cell fate of each of these daughter cells would be determined by the identity of the maternal short RNA segment they receive, which would determine the genomic record activated.

Figure 7:
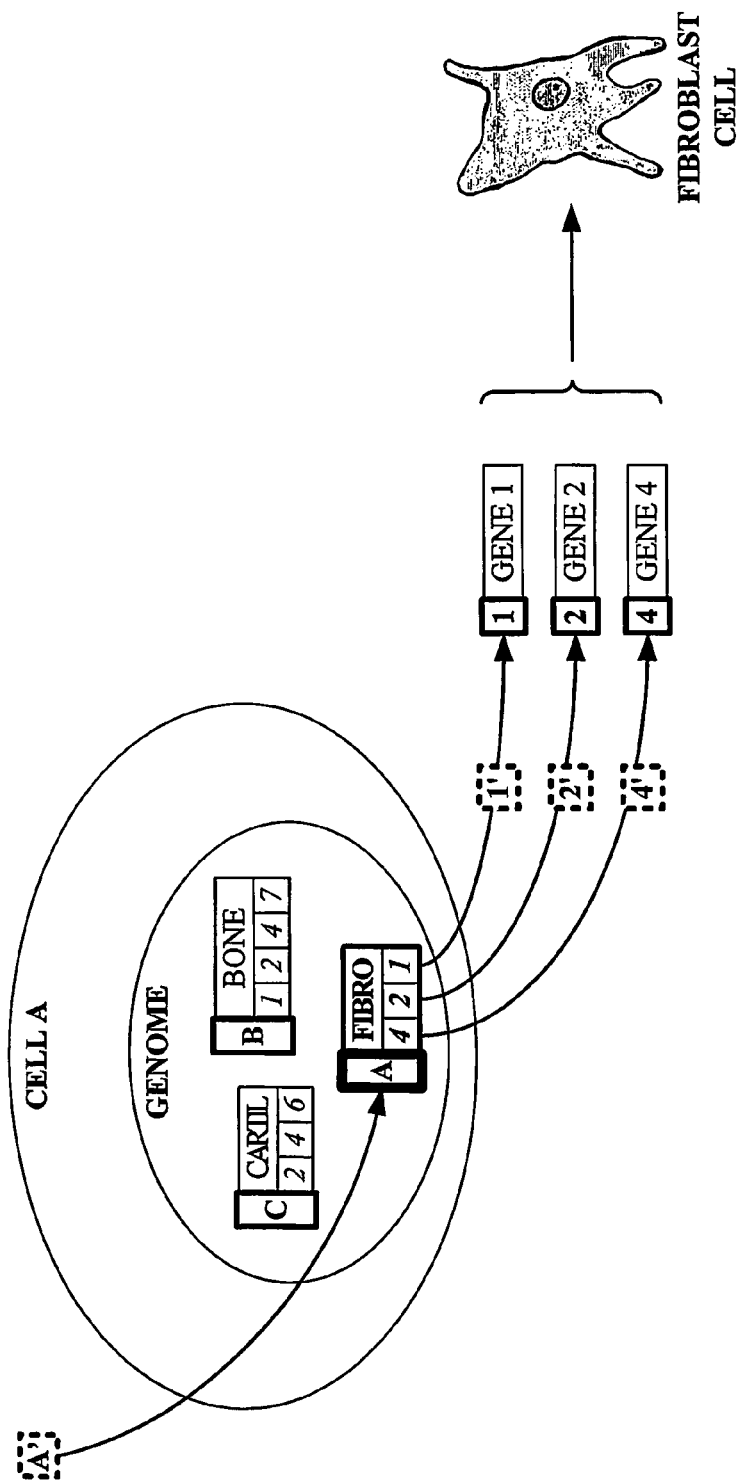
FIG. 7 is a schematic diagram illustrating a 'genomically programmed cell-specific protein expression modulation' concept of the conceptual model of the present invention, addressing the genomic differentiation enigma.

Reference is now made to FIG. 7 which is a schematic diagram illustrating a 'genomically programmed cell-specific protein expression modulation' concept of the conceptual model of the present invention, addressing the genomic differentiation enigma.

Cell A receives a maternal short RNA segment designated A', which activates a genomic record designated FIBRO, by anti-sense binding to a binding site 'header' of this genomic record, designated A. Genomic record FIBRO encodes 3 short RNA segments, designated 1, 2 and 4 respectively, which modulate expression of target genes designated GENE1, GENE2 and GENE4 respectively. Modulation of expression of these genes results in CELL A differentiating into a FIBROBLAST CELL.

Figure 8:
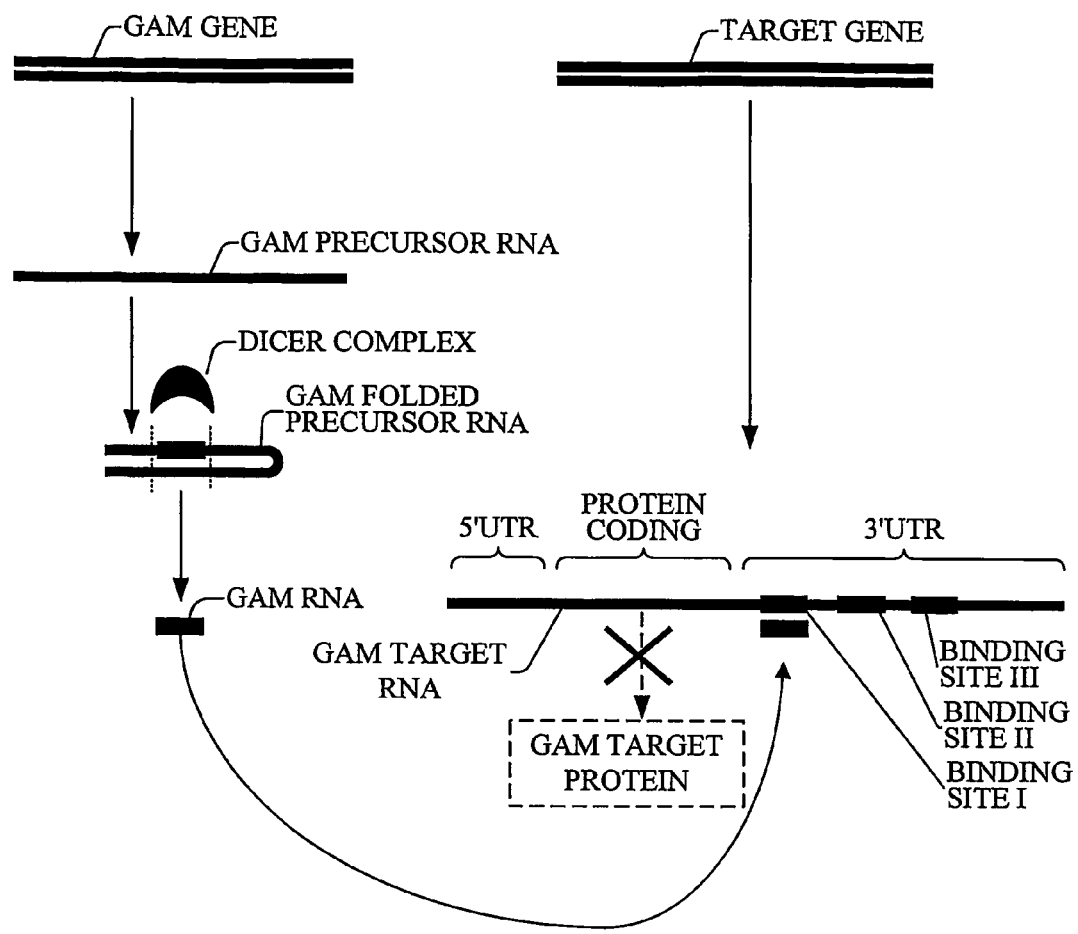
FIG. 8 is a simplified diagram illustrating a mode by which genes of a novel group of genes of the present invention, modulate expression of known target genes.

Reference is now made to FIG. 8, which is a simplified diagram describing each of a plurality of novel bioinformatically detected genes of the present invention, referred to here as Genomic Address Messenger (GAM) genes, which modulates expression of respective target genes thereof, the function and utility of which target genes is known in the art.

GAM is a novel bioinformatically detected regulatory, non protein coding, micro RNA (miRNA) gene. The method by which GAM is detected is described hereinabove with reference to FIGS. 8-15.

GAM GENE and GAM TARGET GENE are human genes contained in the human genome.

GAM GENE encodes a GAM PRECURSOR RNA. Similar to other miRNA genes, and unlike most ordinary genes, GAM PRECURSOR RNA does not encode a protein.

GAM PRECURSOR RNA folds onto itself, forming GAM FOLDED PRECURSOR RNA, which has a two-dimensional 'hairpin structure'. As is well known in the art, this 'hairpin structure', is typical of RNA encoded by miRNA genes, and is due to the fact that the nucleotide sequence of the first half of the RNA encoded by a miRNA gene is an accurately or partially inversed reversed sequence of the nucleotide sequence of the second half thereof. By inversed reversed is meant a sequence which is reversed and wherein each nucleotide is replaced by a complementary nucleotide, as is well known in the art (e.g. ATGGC is the complementary sequence of GCCAT).

An enzyme complex designated DICER COMPLEX 'dices' the GAM FOLDED PRECURSOR RNA into GAM RNA, a single stranded ~22 nt long RNA segment. As is known in the art, 'dicing' of a hairpin structured RNA precursor product into a short ~22 nt RNA segment is catalyzed by an enzyme complex comprising an enzyme called Dicer together with other necessary proteins.

TARGET GENE encodes a corresponding messenger RNA, GAM TARGET RNA. GAM TARGET RNA comprises three regions, as is typical of mRNA of a protein coding gene: a 5' untranslated region, a protein coding region and a 3' untranslated region, designated 5'UTR, PROTEIN CODING and 3'UTR respectively.

GAM RNA binds complementarily to one or more target binding sites located in untranslated regions of GAM TARGET RNA. This complementary binding is due to the fact that the nucleotide sequence of GAM RNA is a partial or accurate inversed reversed sequence of the nucleotide sequence of each of the target binding sites. As an illustration, FIG. 8 shows three such target binding sites, designated BINDING SITE I, BINDING SITE II and BINDING SITE III respectively. It is appreciated that the number of target binding sites shown in FIG. 8 is meant as an illustration only, and is not meant to be limiting GAM RNA may have a different number of target binding sites in untranslated regions of a GAM TARGET RNA. It is further appreciated that while FIG. 8 depicts target binding sites in the 3'UTR region, this is meant as an example only, these target binding sites may be located in the 3'UTR region, the 5'UTR region, or in both 3'UTR and 5'UTR regions.

The complementary binding of GAM RNA to target binding sites on GAM TARGET RNA, such as BINDING SITE I, BINDING SITE II and BINDING SITE III, inhibits translation of GAM TARGET RNA into GAM TARGET PROTEIN. GAM TARGET PROTEIN is therefore outlined by a broken line.

It is appreciated that GAM TARGET GENE in fact represents a plurality of GAM target genes. The mRNA of each one of this plurality of GAM target genes comprises one or more target binding sites, each having a nucleotide sequence which is at least partly complementary to GAM RNA, and which when bound by GAM RNA causes inhibition of translation of respective one or more GAM target proteins.

It is further appreciated by one skilled in the art that the mode of translational inhibition illustrated by FIG. 8 with specific reference to translational inhibition exerted by GAM GENE on one or more TARGET GENE, is in fact common to other known miRNA genes, as is well known in the art.

Nucleotide sequences of each of a plurality of GAM GENEs described by FIG. 8 and their respective genomic source and chromosomal location are further described hereinbelow with reference to Table 1, hereby incorporated by reference.

Nucleotide sequences of GAM PRECURSOR RNA, and a schematic representation of a predicted secondary folding of GAM FOLDED PRECURSOR RNA, of each of a plurality of GAM GENEs described by FIG. 8 are further described hereinbelow with reference to Table 2, hereby incorporated by reference.

Nucleotide sequences of a 'diced' GAM RNA of each of a plurality of GAM GENEs described by FIG. 8 are further described hereinbelow with reference to Table 3, hereby incorporated by reference.

Nucleotide sequences of target binding sites, such as BINDING SITE-I, BINDING SITE-II and BINDING SITE-III of FIG. 8, found on GAM TARGET RNA, of each of a plurality of GAM GENEs described by FIG. 8, and schematic representation of the complementarity of each of these target binding sites to each of a plurality of GAM RNA described by FIG. 8 are described hereinbelow with reference to Table 4, hereby incorporated by reference.

It is appreciated that specific functions and accordingly utilities of each of a plurality of GAM GENEs described by FIG. 8 correlate with, and may be deduced from, the identity of the TARGET GENEs that each of said plurality of GAM GENEs binds and inhibits, and the function of each of said TARGET GENEs, as elaborated hereinbelow with reference to Table 5, hereby incorporated by reference.

Studies establishing known functions of each of a plurality of TARGET GENEs of GAM GENEs of FIG. 8, and correlation of said each of a plurality of TARGET GENEs to known diseases are listed in Table 6, and are hereby incorporated by reference.

The present invention discloses a novel group of genes, the GAM genes, belonging to the miRNA genes group, and for which a specific complementary binding has been determined.

Figure 9:
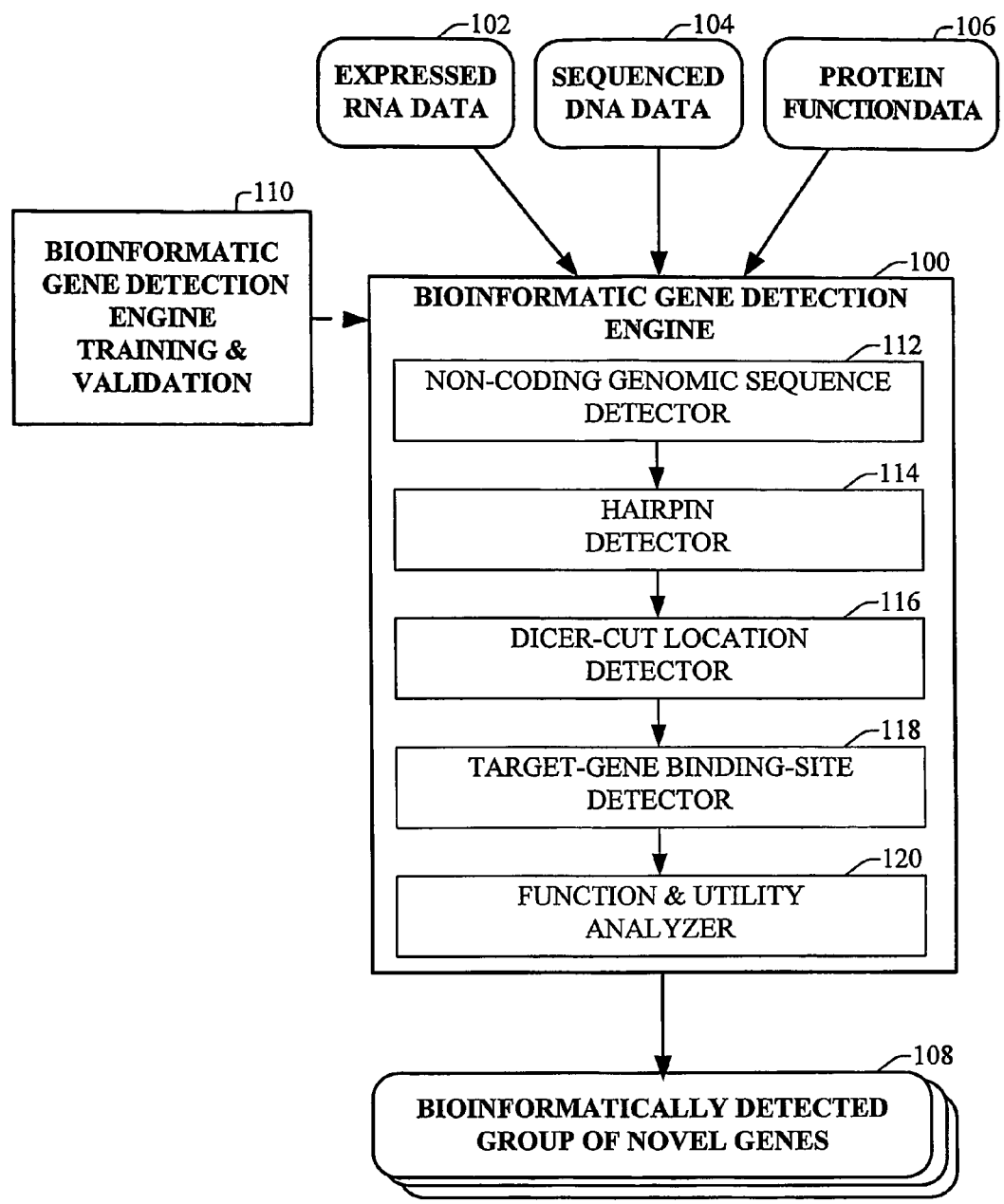
FIG. 9 is a simplified block diagram illustrating a bioinformatic gene detection system capable of detecting genes of the novel group of genes of the present invention, which system is constructed and operative in accordance with a preferred embodiment of the present invention.

Reference is now made to FIG. 9 which is a simplified block diagram illustrating a bioinformatic gene detection system capable of detecting genes of the novel group of genes of the present invention, which system is constructed and operative in accordance with a preferred embodiment of the present invention.

A centerpiece of the present invention is a bioinformatic gene detection engine 100, which is a preferred implementation of a mechanism capable of bioinformatically detecting genes of the novel group of genes of the present invention.

The function of the bioinformatic gene detection engine 100 is as follows: it receives three types of input, expressed RNA data 102, sequenced DNA data 104, and protein function data 106, performs a complex process of analysis of this data as elaborated below, and based on this analysis produces output of a bioinformatically detected group of novel genes designated 108.

Expressed RNA data 102 comprises published expressed sequence tags (EST) data, published mRNA data, as well as other sources of published RNA data. Sequenced DNA data 104 comprises alphanumeric data describing sequenced genomic data, which preferably includes annotation data such as location of known protein coding regions relative to the sequenced data. Protein function data 106 comprises scientific publications reporting studies which elucidated physiological function known proteins, and their connection, involvement and possible utility in treatment and diagnosis of various diseases. Expressed RNA data 102 and sequenced DNA data 104 may preferably be obtained from data published by the National Center for Bioinformatics (NCBI) at the National Institute of Health (NIH) (Jenuth, 2000), as well as from various other published data sources. Protein function data 106 may preferably be obtained from any one of numerous relevant published data sources, such as the Online Mendelian Inherited Disease In M an (OMIM™) database developed by John Hopkins University, and also published by NCBI (2000).

Prior to actual detection of bioinformatically detected novel genes 108 by the bioinformatic gene detection engine 100, a process of bioinformatic gene detection engine training & validation designated 110 takes place. This process uses the known miRNA genes as a training set (some 200 such genes have been found to date using biological laboratory means), to train the bioinformatic gene detection engine 100 to bioinformatically recognize miRNA-like genes, and their respective potential target binding sites. Bioinformatic gene detection engine training & validation 110 is further described hereinbelow with reference to FIG. 10.

The bioinformatic gene detection engine 100 comprises several modules which are preferably activated sequentially, and are described as follows:

A non-coding genomic sequence detector 112 operative to bioinformatically detect non-protein coding genomic sequences. The non-coding genomic sequence detector 112 is further described herein below with reference to FIGS. 11A and 11B.

A hairpin detector 114 operative to bioinformatically detect genomic 'hairpin-shaped' sequences, similar to GAM FOLDED PRECURSOR of FIG. 8. The hairpin detector 114 is further described herein below with reference to FIGS. 12A and 12B.

A dicer-cut location detector 116 operative to bioinformatically detect the location on a hairpin shaped sequence which is enzymatically cut by DICER COMPLEX of FIG. 8. The dicer-cut location detector 116 is further described herein below with reference to FIG. 13A.

A target-gene binding-site detector 118 operative to bioinformatically detect target genes having binding sites, the nucleotide sequence of which is partially complementary to that of a given genomic sequence, such as a sequence cut by DICER COMPLEX of FIG. 8. The target-gene binding-site detector 118 is further described hereinbelow with reference to FIGS. 14A and 14B.

A function & utility analyzer 120 operative to analyze function and utility of target genes, in order to identify target genes which have a significant clinical function and utility. The function & utility analyzer 120 is further described hereinbelow with reference to FIG. 15.

Hardware implementation of the bioinformatic gene detection engine 100 is important, since significant computing power is preferably required in order to perform the computation of bioinformatic gene detection engine 100 in reasonable time and cost. For example, it is estimated that a using a powerful 8-processor server (e.g. DELL POWEREDGE™ 8450, 8 XEON™ 550 MHz processors, 8 GB RAM), over 6 years (!) of computing time are required to detect all MIR genes in the human EST data, together with their respective binding sites. Various computer hardware and software configurations may be utilized in order to address this computation challenge, as is known in the art. A preferred embodiment of the present invention may preferably comprise a hardware configuration, comprising a cluster of one hundred PCs (PENTIUM™ IV, 1.7 GHz, with 40 GB storage each), connected by Ethernet to 12 servers (2-CPU, XEON™ 1.2-2.2 GHz, with ~200 GB storage each), combined with an 8-processor server (8-CPU, Xeon 550 Mhz w/8 GB RAM) connected via 2 HBA fiber-channels to an EMC CLARIION™ 100-disks, 3.6 Terabyte storage device. A preferred embodiment of the present invention may also preferably comprise a software configuration which utilizes a commercial database software program, such as MICROSOFT™ SQL Server 2000. Using such preferred hardware and software configuration, may reduce computing time required to detect all MIR genes in the human EST data, and their respective binding sites, from 6 years to 45 days. It is appreciated that the above mentioned hardware configuration is not meant to be limiting, and is given as an illustration only. The present invention may be implemented in a wide variety of hardware and software configurations.

The present invention discloses 8607 novel genes of the GAM group of genes, which have been detected bioinformatically, as described hereinbelow with reference to Table 1 through Table 6, and 1096 novel genes of the GR group of genes, which have been detected bioinformatically, as described hereinbelow with reference to Table 7. Laboratory confirmation of 50 bioinformatically predicted genes of the GAM group of genes, and several bioinformatically predicted genes of the GR group of genes, is described hereinbelow with reference to FIGS. 21 through 24C.

Reference is now made to FIG. 10 which is a simplified flowchart illustrating operation of a mechanism for training a computer system to recognize the novel genes of the present invention. This mechanism is a preferred implementation of the bioinformatic gene detection engine training & validation 110 described hereinabove with reference to FIG. 9.

BIOINFORMATIC GENE DETECTION ENGINE TRAINING & VALIDATION 110 of FIG. 9 begins by training the bioinformatic gene detection engine to recognize known miRNA genes, as designated by numeral 122. This training step comprises HAIRPIN DETECTOR TRAINING & VALIDATION 124, further described hereinbelow with reference to FIG. 12A, DICER-CUT LOCATION DETECTOR TRAINING & VALIDATION 126, further described hereinbelow with reference to FIGS. 13A and 13B, and TARGET-GENE BINDING-SITE DETECTOR TRAINING & VALIDATION 128, further described hereinbelow with reference to FIG. 14A.

Next, the BIOINFORMATIC GENE DETECTION ENGINE 100 is used to bioinformatically detect sample novel genes, as designated by numeral 130. Examples of sample novel genes thus detected are described hereinbelow with reference to FIGS. 21 through 24C.

Finally, wet lab experiments are preferably conducted in order to validate expression and preferably function of the sample novel genes detected by the BIOINFORMATIC GENE DETECTION ENGINE 100 in the previous step, as designated by reference numeral 132. An example of wet-lab validation of the above mentioned sample novel gene bioinformatically detected by the system is described hereinbelow with reference to FIGS. 22A and 22B.

Figure 11A:
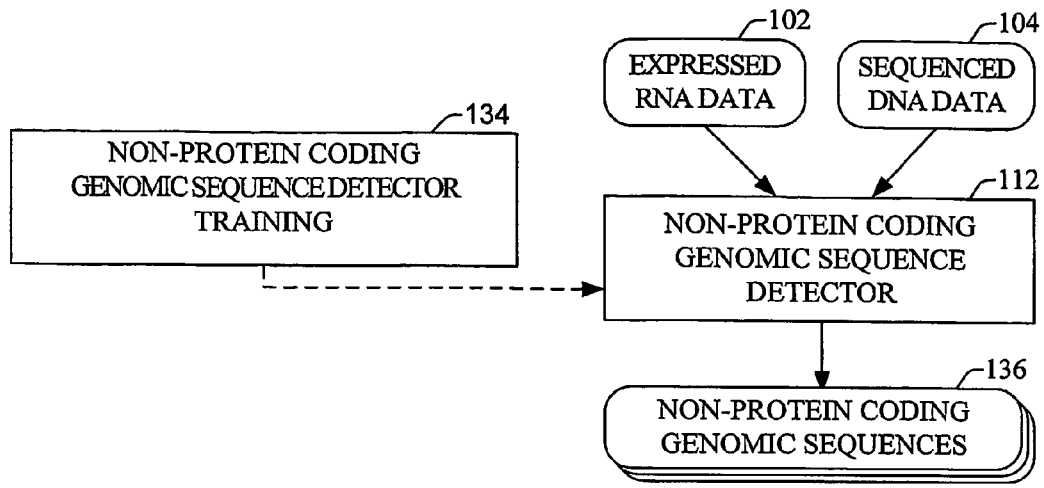
FIG. 11A is a simplified block diagram of a non-coding genomic sequence detector constructed and operative in accordance with a preferred embodiment of the present invention.

Reference is now made to FIG. 11A which is a simplified block diagram of a preferred implementation of the NON-CODING GENOMIC SEQUENCE DETECTOR 112 described hereinabove with reference to FIG. 9. The NON-PROTEIN CODING GENOMIC SEQUENCE DETECTOR 112 of FIG. 9 preferably receives as input at least two types of published genomic data: EXPRESSED RNA DATA 102 and SEQUENCED DNA DATA 104. The EXPRESSED RNA DATA can include, among others, EST data, EST clusters data, EST genome alignment data and mRNA data. Sources for EXPRESSED RNA DATA 102 include NCBI dbEST, NCBI UniGene clusters and mapping data, and TIGR gene indices. SEQUENCED DNA DATA 104 includes both sequence data (FASTA format files), and features annotation (GenBank file format) mainly from NCBI database. After its initial training, indicated by numeral 134, and based on the above mentioned input data, the NON-PROTEIN CODING GENOMIC SEQUENCE DETECTOR 112 produces as output a plurality of NON-PROTEIN CODING GENOMIC SEQUENCES 136. Preferred operation of the NON-PROTEIN CODING GENOMIC SEQUENCE DETECTOR 112 is described hereinbelow with reference to FIG. 11B.

Figure 11B:
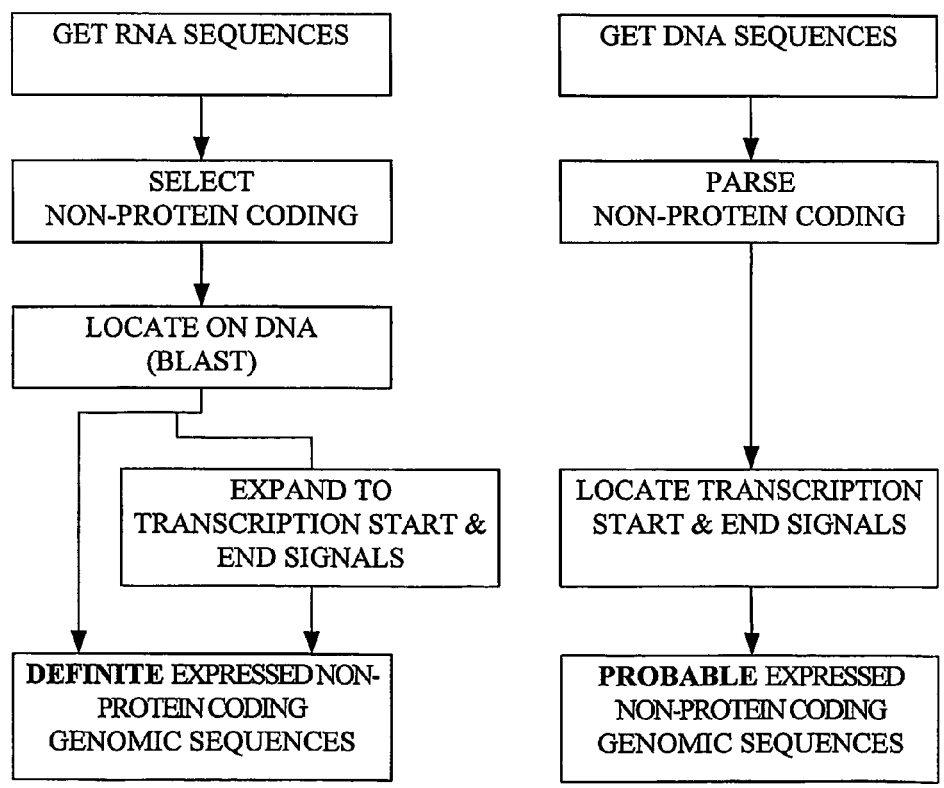
FIG. 11B is a simplified flowchart illustrating operation of a non-coding genomic sequence detector constructed and operative in accordance with a preferred embodiment of the present invention.

Reference is now made to FIG. 11B which is a simplified flowchart illustrating a preferred operation of the NON-CODING GENOMIC SEQUENCE DETECTOR 112 of FIG. 9. Detection of NON-PROTEIN CODING GENOMIC SEQUENCES 136, generally preferably progresses in one of the following two paths:

A first path for detecting NON-PROTEIN CODING GENOMIC SEQUENCES 136 begins by receiving a plurality of known RNA sequences, such as EST data. Each RNA sequence is first compared to all known protein-coding sequences, in order to select only those RNA sequences which are non-protein coding, i.e. intergenic or intronic. This can preferably be performed by sequence comparison of the RNA sequence to known protein coding sequences, using one of many alignment algorithms known in the art, such as BLAST. This sequence comparison to the DNA preferably also provides the localization of the RNA sequence on the DNA.

Alternatively, selection of non-protein coding RNA sequences and their localization to the DNA can be performed by using publicly available EST clusters data and genomic mapping databases, such as UNIGENE database published by NCBI or TIGR database, in order map expressed RNA sequences to DNA sequences encoding them, to find the right orientation of EST sequences, and to exclude ESTs which map to protein coding DNA regions, as is well known in the art. Public databases, such as TIGR, may also be used to map an EST to a cluster of ESTs, assumed to be expressed as one piece, and is known in the art as Tentative Human Consensus. Publicly available genome annotation databases, such as NCBI's GENBANK, may also be used to deduce expressed intronic sequences.

Optionally, an attempt may be made to 'expand' the non-protein RNA sequences thus found, by searching for transcription start and end signals, upstream and downstream of location of the RNA on the DNA respectively, as is well known in the art.

A second path for detecting non-protein coding genomic sequences starts by receiving DNA sequences. The DNA sequences are parsed into non protein coding sequences, based on published DNA annotation data, by extracting those DNA sequences which are between known protein coding sequences. Next, transcription start and end signals are sought. If such signals are found, and depending on their 'strength', probable expressed non-protein coding genomic sequences are yielded. Such approach is especially useful for identifying novel GAM genes which are found in proximity to other known miRNA genes, or other wet-lab validated GAM genes. Since, as described hereinbelow with reference to FIG. 16, GAM genes are frequently found in clusters, therefore sequences near a known miRNA are more likely to contain novel GAM genes. Optionally, sequence orthology, i.e. sequences conservation in an evolutionary related species, may be used to select genomic sequences having higher probability of containing expressed novel GAM genes.

Figure 12A:
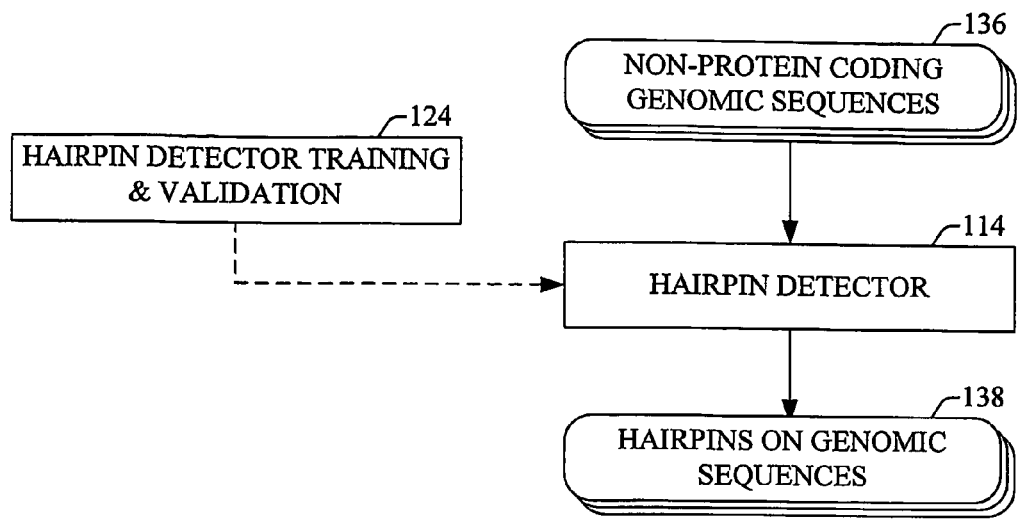
FIG. 12A is a simplified block diagram of a hairpin detector constructed and operative in accordance with a preferred embodiment of the present invention.

Reference is now made to FIG. 12A which is a simplified block diagram of a preferred implementation of the HAIRPIN DETECTOR 114 described hereinabove with reference to FIG. 9.

The goal of the HAIPIN DETECTOR 114 is to detect 'hairpin' shaped genomic sequences, similar to those of known miRNA genes. As mentioned hereinabove with reference to FIG. 8, a 'hairpin' genomic sequence refers to a genomic sequence which 'folds onto itself' forming a hairpin like shape, due to the fact that nucleotide sequence of the first half of the nucleotide sequence is an accurate or partial complementary sequence of the nucleotide sequence of its second half.

The HAIRPIN DETECTOR 114 of FIG. 9 receives as input a plurality of NON-PROTEIN CODING GENOMIC SEQUENCES 136 of FIG. 11A. After a phase of HAIRPIN DETECTOR TRAINING & VALIDATION 124 of FIG. 10, the HAIRPIN DETECTOR 114 is operative to detect and output 'hairpin shaped' sequences, which are found in the input NON-PROTEIN CODING GENOMIC SEQUENCES 138. The hairpin shaped sequences detected by the HAIRPIN DETECTOR 114 are designated HAIRPINS ON GENOMIC SEQUENCES 138. Preferred operation of the HAIRPIN DETECTOR 114 is described hereinbelow with reference to FIG. 12B.

The phase of HAIRPIN DETECTOR TRAINING & VALIDATION 124 is an iterative process of applying the HAIRPIN DETECTOR 114 to known hairpin shaped miRNA genes, calibrating the HAIRPIN DETECTOR 114 such that it identifies the training set of known hairpins, as well as sequences which are similar thereto. In a preferred embodiment of the present invention, THE HAIRPIN DETECTOR TRAINING & VALIDATION 124 trains and validates each of the steps of operation of the HAIRPIN DETECTOR 114, which steps are described hereinbelow with reference to FIG. 12B.

The hairpin detector training and validation 124 preferably uses two sets of data: a training set of known miRNA genes, such as 440 miRNA genes of *H. sapiens, M. musculus, C. elegans, C. Brigssae* and *D. Melanogaster*, annotated in RFAM database (Griffiths-Jones 2003), and a large 'background set' of hairpins found in expressed non-protein coding genomic sequences, such as a set of 21,985 hairpins found in Tentative Human Concensus (THC) sequences in TIGR database. The 'background set' is expected to comprise some valid, previously undetected miRNA hairpins, and many hairpins which are not miRNA hairpins.

In order to validate the performance of the HAIRPIN DETECTOR 114, a validation method is preferably used, which validation method is a variation on the k-fold cross validation method (Mitchell, 1997). This preferred validation method is devised to better cope with the nature of the training set, which includes large families of similar and even identical miRNAs. The training set is preferably first divided into clusters of miRNAs such that any two miRNAs that belong to different clusters have an Edit Distance score (see Algorithms and Strings; Dan Gusfield, Cambridge University Press, 1997) of at least D=3, i.e. they differ by at least 3 editing operations. Next, the group of clusters is preferably divided into k sets. Then standard k-fold cross validation is preferably performed on this group of clusters, preferably using k=5, such that the members of each cluster are all in the training set or in the test set. It is appreciated that without the prior clustering, standard cross validation methods results in much higher performance of the predictors due to the redundancy of training examples, within the genome of a species and across genomes of different species.

In a preferred embodiment of the present invention, using the above-mentioned validation method, the efficacy of the HAIRPIN DETECTOR 114 is indeed validated: for example, when a similarity threshold is chosen such that 90% of the published miRNA-precursor hairpins are successfully predicted, only 7.6% of the 21,985 background hairpins are predicted to be miRNA-precursors, some of which may indeed be previously unknown miRNA precursors.

Figure 12B:
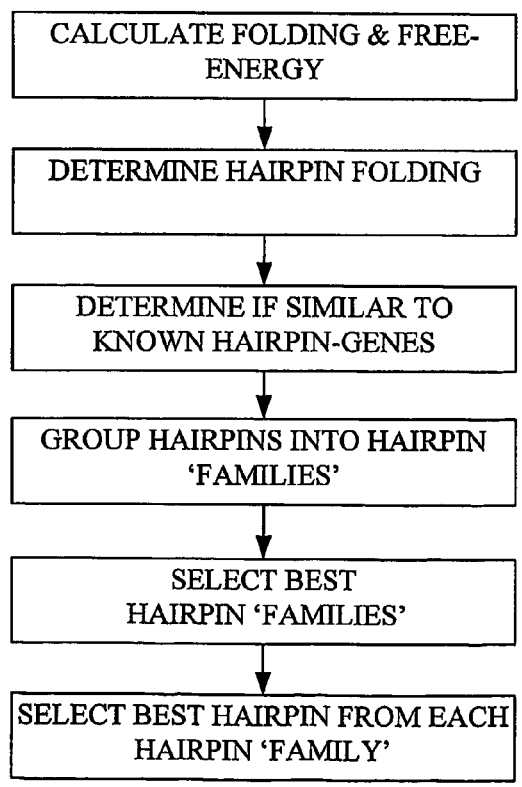
FIG. 12B is a simplified flowchart illustrating operation of a hairpin detector constructed and operative in accordance with a preferred embodiment of the present invention.

Reference is now made to FIG. 12B which is a simplified flowchart illustrating a preferred operation of the HAIRPIN DETECTOR 114 of FIG. 9.

A hairpin structure is a secondary structure, resulting from the nucleotide sequence pattern: the nucleotide sequence of the first half of the hairpin is a partial or accurate inversed reversed sequence of the nucleotide sequence of the second half thereof. Various methodologies are known in the art for prediction of secondary and tertiary hairpin structures, based on given nucleotide sequences.

In a preferred embodiment of the present invention, the HAIRPIN DETECTOR 114 initially calculates possible secondary structure folding patterns of a given one of the non-protein coding genomic sequences 136 and the respective energy of each of these possible secondary folding patterns, preferably using a secondary structure folding algorithm based on free-energy minimization, such as the MFOLD algorithm (Mathews et al., 1999), as is well known in the art.

Next, the HAIRPIN DETECTOR 114 analyzes the results of the secondary structure folding, in order to determine the presence, and location of hairpin folding structures. A secondary structure folding algorithm, such as MFOLD algorithm, typically provides as output a listing of the base-pairing of the folded shape, i.e. a listing of each pair of connected nucleotides in the sequence. The goal of this second step is to asses this base-pairing listing, in order to determine if it describes a hairpin type bonding pattern. Preferably, each of the sequences that is determined to describe a hairpin structure is folded separately in order to determine its exact folding pattern and free-energy.

The HAIRPIN DETECTOR 114 then assess those hairpin structures found by the previous step, comparing them to hairpins of known miRNA genes, using various characteristic hairpin features such as length of the hairpin and of its loop, free-energy and thermodynamic stability, amount and type of mismatched nucleotides, existence of sequence repeat-elements. Only hairpins that bear statistically significant resemblance to the training set of known miRNA hairpins, according to the abovementioned parameters are accepted.

In a preferred embodiment of the present invention, similarity to the training set of known miRNA hairpins is determined using a 'similarity score' which is calculated using a weighted sum of terms, where each term is a function of one of the abovementioned hairpin features, and the parameters of each function are learned from the set of known hairpins, as described hereinabove with reference to hairpin detector training & validation 124. The weight of each term in the similarity score is optimized so as to achieve maximal separation between the distribution of similarity scores of hairpins which have been validated as miRNA-precursor hairpins, and the distribution of similarity scores of hairpins detected in the 'background set' mentioned hereinabove with reference to FIG. 12B, many of which are expected not to be miRNA-precursor hairpins.

In another preferred embodiment of the present invention, the above-mentioned DETERMINE IF SIMILAR TO KNOWN HAIRPIN-GENES step may may preferably be split into two stages. The first stage is a permissive filter that implements a simplified scoring method, based on a subset of the hairpin features described hereinabove, such as minimal length and maximal free energy. The second stage is more stringent, and a full calculation of the weighted sum of terms described hereinabove is performed. This second stage may preferably be performed only on the subset of hairpins that survived prior filtering stages of the hairpin-detector 114.

Lastly, the HAIRPIN DETECTOR 114 attempts to select those hairpin structures which are as thermodynamically stable as the hairpins of known miRNA genes. This may preferably be achieved in various manners. A preferred embodiment of the present invention utilizes the following methodology preferably comprising three logical steps:

First, the HAIRPIN DETECTOR 114 attempts to group potential hairpins into 'families' of closely related hairpins. As is known in the art, a free-energy calculation algorithm, typically provides multiple 'versions' each describing a different possible secondary structure folding pattern for the given genomic sequence, and the free energy of such possible folding. The HAIRPIN DETECTOR 114 therefore preferably assesses all hairpins found in each of the 'versions', grouping hairpins which appear in different versions, but which share near identical locations into a common 'family' of hairpins. For example, all hairpins in different versions, the center of which hairpins is within 7 nucleotides of each other may preferably be grouped to a single 'family'. Hairpins may also be grouped to a single 'family' if the sequences of one or more hairpins are identical to, or are subsequences of, the sequence of another hairpin.

Next, hairpin 'families' are assessed, in order to select only those families which represent hairpins that are as stable as those of known miRNA hairpins. Preferably only families which are represented in a majority of the secondary structure folding versions, such as at least in 65% or 80% or 100% of the secondary structure folding versions, are considered stable.

Finally, an attempt is made to select the most suitable hairpin from each selected family. For example, a hairpin which appears in more versions than other hairpins, and in versions the free-energy of which is lower, may be preferred.

In another preferred embodiment of the present invention, hairpins with homology to other species, and clusters of thermodynamically stable hairpin are further favored.

Figure 13A:
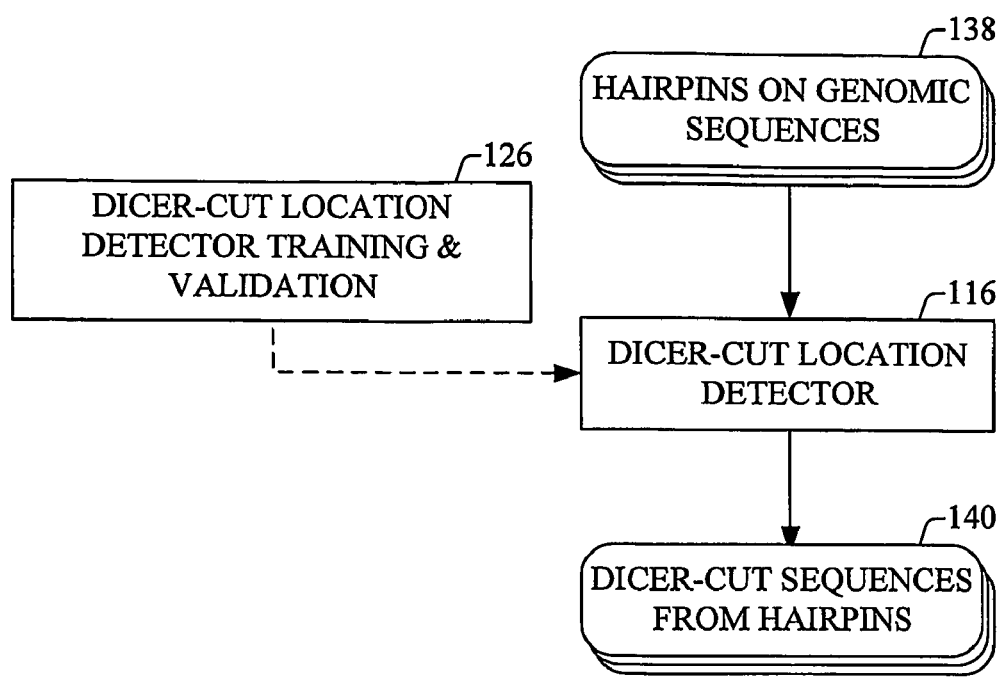
FIG. 13A is a simplified block diagram of a dicer-cut location detector constructed and operative in accordance with a preferred embodiment of the present invention.

Reference is now made to FIG. 13A which is a simplified block diagram of a preferred implementation of the DICER-CUT LOCATION DETECTOR 116 described hereinabove with reference to FIG. 9.

The goal of the DICER-CUT LOCATION DETECTOR 116 is to detect the location in which DICER COMPLEX of FIG. 8, comprising the enzyme Dicer, would 'dice' the given hairpin sequence, similar to GAM FOLDED PRECURSOR RNA, yielding GAM RNA both of FIG. 8.

The DICER-CUT LOCATION DETECTOR 116 of FIG. 9 therefore receives as input a plurality of HAIRPINS ON GENOMIC SEQUENCES 138 of FIG. 12A, which were calculated by the previous step, and after a phase of DICER-CUT LOCATION DETECTOR TRAINING & VALIDATION 126, is operative to detect a respective plurality of DICER-CUT SEQUENCES FROM HAIRPINS 140, one for each hairpin.

In a preferred embodiment of the present invention, the DICER-CUT LOCATION DETECTOR 116 preferably uses standard machine learning techniques such as K nearest-neighbors, Bayesian networks and Support Vector Machines (SVM), trained on known dicer-cut locations of known miRNA genes in order to predict dicer-cut locations of novel GAM genes. The DICER-CUT LOCATION DETECTOR TRAINING & VALIDATION 126 is further described hereinbelow with reference to FIG. 13B.

Figure 13B:
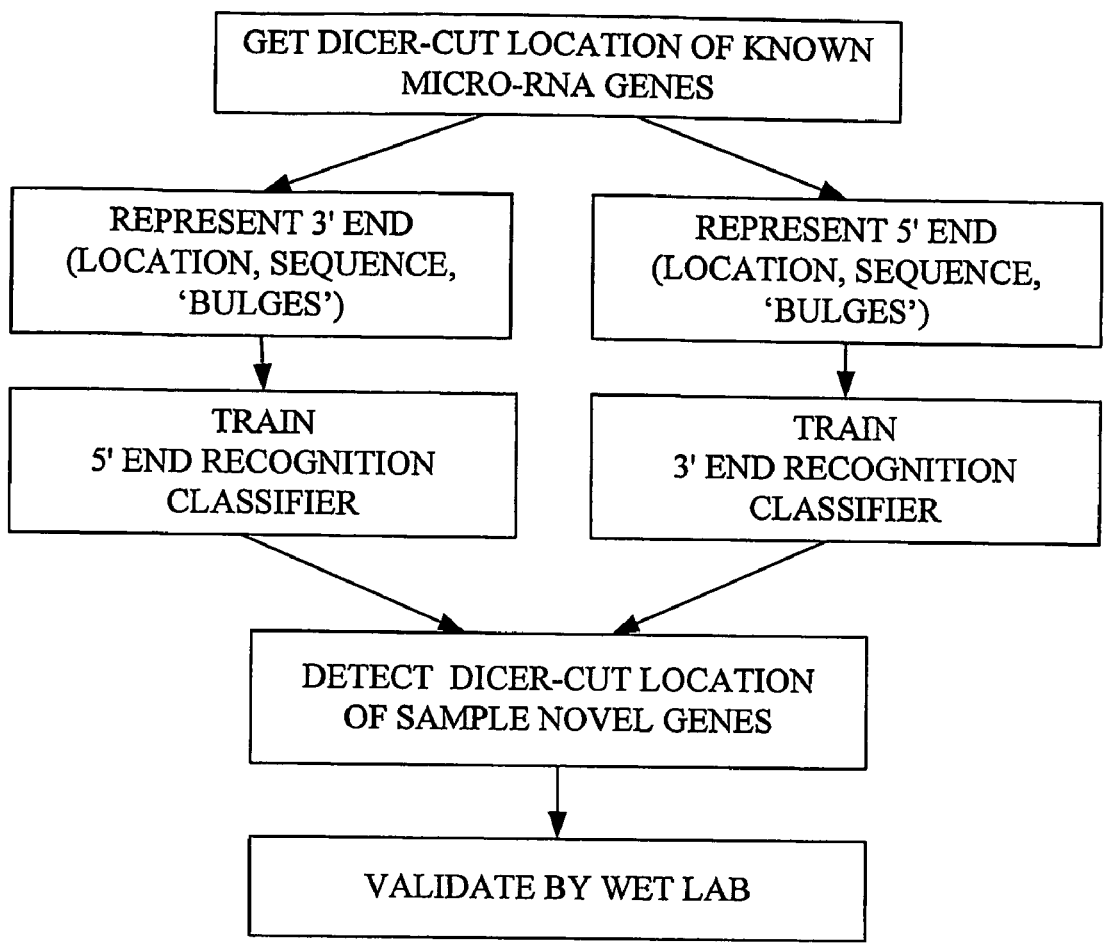
FIG. 13B is a simplified flowchart illustrating training of a dicer-cut location detector constructed and operative in accordance with a preferred embodiment of the present invention.

Reference is now made to FIG. 13B which is a simplified flowchart illustrating a preferred implementation of DICER-CUT LOCATION DETECTOR TRAINING & VALIDATION 126 of FIG. 10.

The general goal of the DICER-CUT LOCATION DETECTOR TRAINING & VALIDATION 126 is to analyze known hairpin shaped miRNA-precursors and their respective dicer-cut miRNA, in order to determine a common pattern to the dicer-cut location of known miRNA genes. Once such a common pattern is deduced, it may preferably be used by the DICER-CUT LOCATION DETECTOR 116, in detecting the predicted DICER-CUT SEQUENCES FROM HAIRPINS 140, from the respective HAIRPINS ON GENOMIC SEQUENCES 138, all of FIG. 13A.

First, the dicer-cut location of all known miRNA genes is obtained and studied, so as to train the DICER-CUT LOCATION DETECTOR 116: for each of the known miRNA, the location of the miRNA relative to its hairpin-shaped miRNA-precursor is noted.

The 5' and 3' ends of the dicer-cut location of each of the known miRNA genes is represented relative to the respective miRNA precursor hairpin, as well as to the nucleotides in each location along the hairpin. Frequency and identity of nucleotides and of nucleotide-pairing, and position of nucleotides and nucleotide pairing relative to the dicer-cut location in the known miRNA precursor hairpins is analyzed and modeled. In a preferred embodiment of the present invention, features learned from published miRNAs include: distance from hairpin's loop, nucleotide content, positional distribution of nucleotides and mismatched-nucleotides, and symmetry of mismatched-nucleotides.

Different techniques are well known in the art of machine learning for analysis of existing pattern from a given 'training set' of examples, which techniques are then capable, to a certain degree, to detect similar patterns in other, previously unseen examples. Such machine learning techniques include, but are not limited to neural networks, Bayesian networks, Support Vector Machines (SVM), Genetic Algorithms, Markovian modeling, Maximum Liklyhood modeling, Nearest Neighbor algorithms, Decision trees and other techniques, as is well known in the art.

The DICER-CUT LOCATION DETECTOR 116 preferably uses such standard machine learning techniques to predict either the 5' end or both the 5' and 3' ends of the miRNA excised, or 'diced' by the Dicer enzyme from the miRNA hairpin shaped precursor, based on known pairs of miRNA-precursors and their respective resulting miRNAs. The nucleotide sequences of 440 published miRNA and their corresponding hairpin precursors are preferably used for training and evaluation of the dicer-cut location detector module.

Using the abovementioned training set, machine learning predictors, such as a Support Vector Machine (SVM) predictor, are implemented, which predictors test every possible nucleotide on a hairpin as a candidate for being the 5' end or the 3' end of a miRNA. Other machine learning predictors include predictors based on Nearest Neighbor, Bayesian modeling, and K-nearest-neighbor algorithms. The training set of the published miRNA precursor sequences is preferably used for training multiple separate classifiers or predictors, each of which produces a model for the 5' or 3' end of a miRNA relative to its hairpin precursor. The models take into account various miRNA properties such as the distance of the respective (3' or 5') end of the miRNA from the hairpin's loop, the nucleotides at its vicinity and the local 'bulge' (i.e. base-pair mismatch) structure.

Performance of the resulting predictors, evaluated on the above-mentioned validation set of 440 published miRNAs using k-fold cross validation (Mitchell, 1997) with k=3, is found to be as follows: in 70% of known miRNAs 5'-end location is correctly determined by an SVM predictor within up to 2 nucleotides; a Nearest Neighbor (EDIT DISTANCE) predictor achieves 53% accuracy (233/440); a Two-Phased predictor that uses Baysian modeling (TWO PHASED) achieves 79% accuracy (348/440), when only the first phase is used, and 63% (277/440) when both phases are used; a K-nearest-neighbor predictor (FIRST-K) achieves 61% accuracy (268/440). The accuracies of all predictors are considerably higher on top scoring subsets of published miRNA.

Finally, in order to validate the efficacy and accuracy of the dicer-cut location detector 116, a sample of novel genes detected thereby is preferably selected, and validated by wet lab. Laboratory results validating the efficacy of the dicer-cut location detector 116 are described hereinbelow with reference to FIGS. 21 through 24C.

Figure 13C:
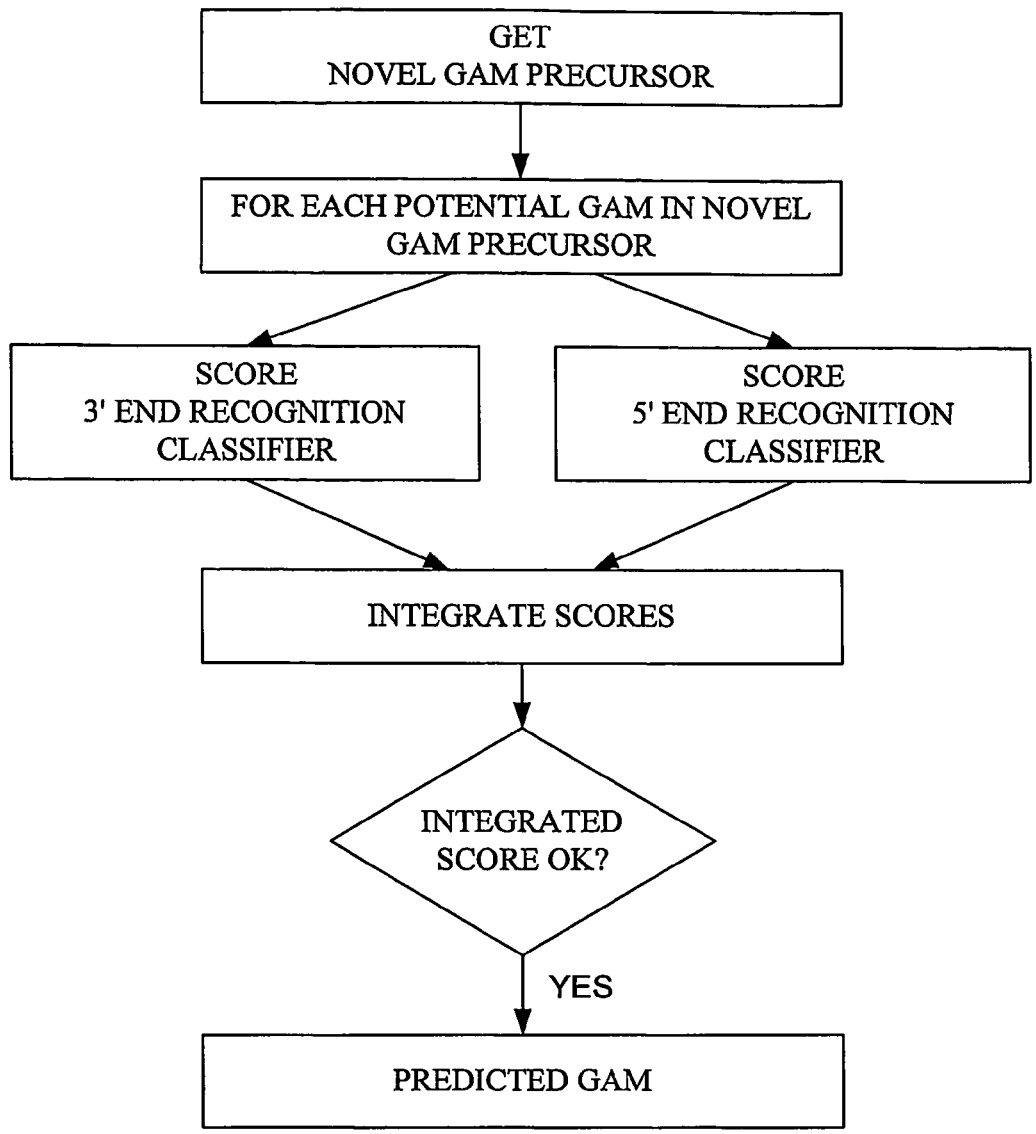
FIG. 13C is a simplified flowchart illustrating operation of a dicer-cut location detector constructed and operative in accordance with a preferred embodiment of the present invention.

Reference is now made to FIG. 13C which is a simplified flowchart illustrating operation of DICER-CUT LOCATION DETECTOR 116 of FIG. 9, constructed and operative in accordance with a preferred embodiment of the present invention.

The DICER CUT LOCATION DETECTOR 116 is a machine learning computer program module, which is trained on recognizing dicer-cut location of known miRNA genes, and based on this training, is operable to detect dicer cut location of novel GAM FOLDED PRECURSOR RNA. In a preferred embodiment of the present invention, the dicer-cut location module preferably utilizes machine learning algorithms, such as Support Vector Machine (SVM), Bayesian modeling, Nearest Neighbors, and K-nearest-neighbor, as is well known in the art.

When assessing a novel GAM precursor, all 19-24 nucleotide long segments comprised in the GAM precursor are initially considered as 'potential GAMs', since the dicer-cut location is initially unknown.

For each such potential GAM, its 5' end, or its 5' and 3' ends are scored by two or more recognition classifiers or predictors.

In a preferred embodiment of the present invention, the DICER-CUT LOCATION DETECTOR 116 preferably uses a Support Vector Machine predictor trained on features such as distance from hairpin's loop, nucleotide content, positional distribution of nucleotides and mismatched-nucleotides, and symmetry of mismatched-nucleotides.

In another preferred embodiment of the present invention, the DICER-CUT LOCATION DETECTOR 116 preferably uses an 'EDIT DISTANCE' predictor, which seeks sequences that are similar to those of published miRNAs, utilizing the Nearest Neighbor algorithm, where the similarity metric between two sequences is a variant of the edit distance algorithm (Algorithms and Strings, Dan Gusfield, Cambridge University Press, 1997). This predictor is based on the observation that miRNAs tend to form clusters (Dostie, 2003), the members of which show marked sequence similarity to each other.

In yet another preferred embodiment of the present invention, the DICER-CUT LOCATION DETECTOR 116 preferably uses a 'TWO PHASED' predictor, which predicts the dicer-cut location in two distinct phases: (a) selecting the double-stranded segment of the hairpin comprising the miRNA by naïve Bayesian modeling (Mitchell, 1997), and (b) detecting which strand contains the miRNA by either naïve or by K-nearest-neighbor modeling. The latter is a variant oft he 'FIRST-K' predictor described herein below, with parameters optimized for this specific task. The 'TWO PHASED' predictor may be operated in two modes: either utilizing only the first phase and thereby producing two alternative dicer-cut location predictions, or utilizing both phases and thereby producing only one final dicer-cut location.

In still another preferred embodiment of the present invention, the DICER-CUT LOCATION DETECTOR 116 preferably uses a 'FIRST-K' predictor, which utilizes the K-nearest-neighbor algorithm. The similarity metric between any two sequences is 1-E/L, where L is a parameter, preferably 8-10 and E is the edit distance between the two sequences, taking into account only the first L nucleotides of each sequence. If the K-nearest-neighbor scores of two or more locations on the hairpin are not significantly different, these locations are further ranked by a Bayesian model, similar to the one described hereinabove.

Scores of two or more of the abovementioned classifiers or predictors are integrated, yielding an integrated score for each 'potential GAM'. As an example, FIG. 13C illustrates integration of scores from two classifiers, a 3' end recognition classifier and a 5' end recognition classifier, the scores of which are integrated to yield an integrated score. In a preferred embodiment of the present invention, INTEGRATED SCORE of 13C preferably implements a 'best-of-breed' approach, accepting only 'potential GAMs' that score highly on one of the above mentioned EDIT DISTANCE', or 'TWO-PHASED' predictors. In this context, 'high scores' means scores which have been demonstrated to have low false positive value when scoring known miRNAs.

The INTEGRATED SCORE is then evaluated as follows: (a) the 'potential GAM' having the highest score is taken to be the most probable GAM, and (b) if the integrated score of this 'potential GAM' is higher than a pre-defined threshold, then the potential GAM is accepted as the PREDICTED GAM.

Figure 14A:
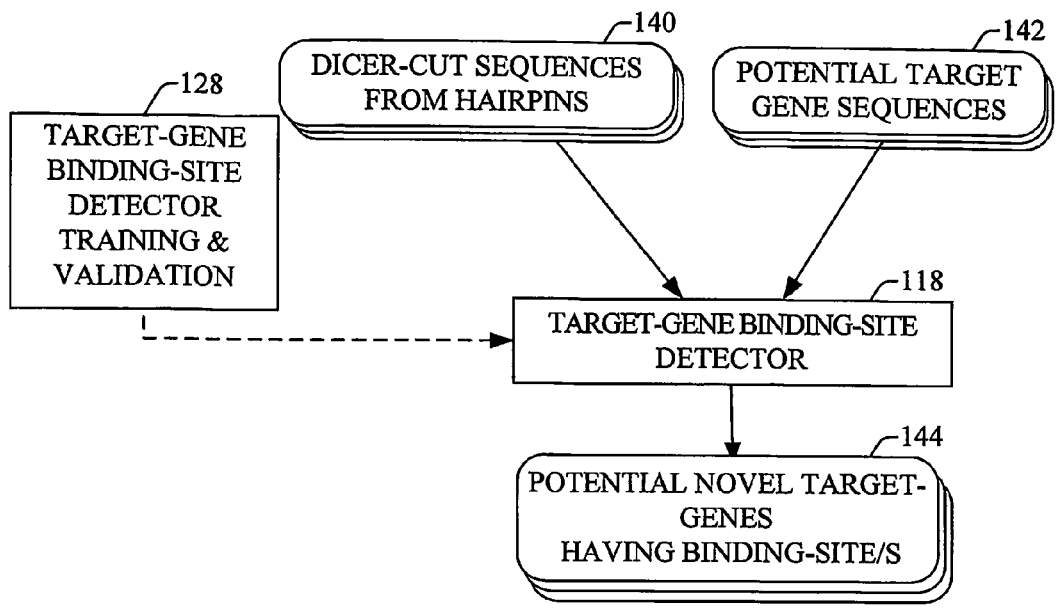
FIG. 14A is a simplified block diagram of a target-gene binding-site detector constructed and operative in accordance with a preferred embodiment of the present invention.

Reference is now made to FIG. 14A which is a simplified block diagram of a preferred implementation of the TARGET-GENE BINDING-SITE DETECTOR 118 described hereinabove with reference to FIG. 9. The goal of the TARGET-GENE BINDING-SITE DETECTOR 118 is to detect a BINDING SITE of FIG. 8, including binding sites located in untranslated regions of the RNA of a known gene, the nucleotide sequence of which BINDING SITE is a partial or accurate inversed reversed sequence to that of a GAM RNA of FIG. 8, thereby determining that the above mentioned known gene is a target gene of GAM of FIG. 8.

The TARGET-GENE BINDING-SITE DETECTOR 118 of FIG. 9 therefore receives as input a plurality of DICER-CUT SEQUENCES FROM HAIRPINS 140 of FIG. 13A which were calculated by the previous step, and a plurality of POTENTIAL TARGET GENE SEQUENCES 142 which derive from SEQUENCED DNA DATA 104 of FIG. 9, and after a phase of TARGET-GENE BINDING-SITE DETECTOR TRAINING & VALIDATION 128 is operative to detect a plurality of POTENTIAL NOVEL TARGET-GENES HAVING BINDING SITE/S 144 the nucleotide sequence of which is a partial or accurate inversed reversed sequence to that of each of the plurality of DICER-CUT SEQUENCES FROM HAIRPINS 140. Preferred operation of the TARGET-GENE BINDING-SITE DETECTOR 118 is further described hereinbelow with reference to FIG. 14B.

Figure 14B:
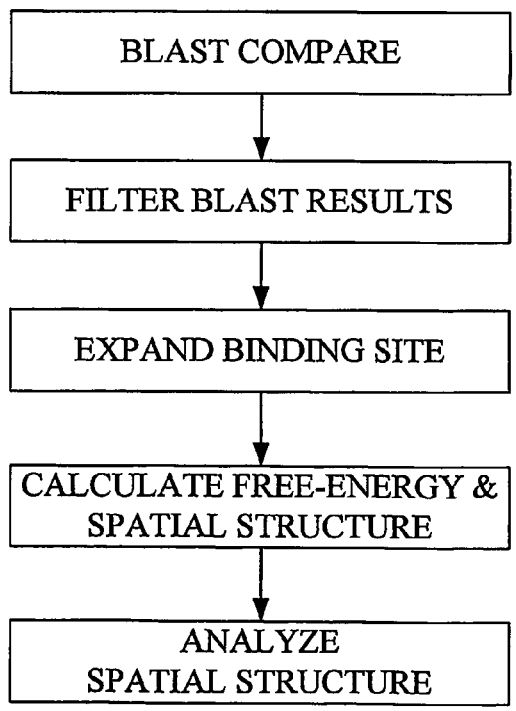
FIG. 14B is a simplified flowchart illustrating operation of a target-gene binding-site detector constructed and operative in accordance with a preferred embodiment of the present invention.

Reference is now made to FIG. 14B which is a simplified flowchart illustrating a preferred operation of the target-gene binding-site detector 118 of FIG. 9.

In a preferred embodiment of the present invention, the target-gene binding-site detector 118 first uses a sequence comparison algorithm such as BLAST in order to compare the nucleotide sequence of each of the plurality of dicer-cut sequences from hairpins 140, to the potential target gene sequences 142, such a untranslated regions of known mRNAs, in order to find crude potential matches. Alternatively, the sequence comparison may preferably be performed using a sequence match search tool that is essentially a variant of the EDIT DISTANCE algorithm described hereinabove with reference to FIG. 13C, and the Nearest Neighbor algorithm (Mitchell, 1997).

Results of the sequence comparison, performed by BLAST or other algorithms such as EDIT DISTANCE, are then filtered, preferably utilizing BLAST or EDIT DISTANCE score, to results which are similar to those of known binding sites (e.g. binding sites of miRNA genes Lin-4 and Let-7 to target genes Lin-14, Lin-41, Lin 28 etc.). Next the binding site is expanded, checking if nucleotide sequenced immediately adjacent to the binding site found by the sequence comparison algorithm (e.g. BLAST or EDIT DISTANCE), may improve the match. Suitable binding sites, then are computed for free-energy and spatial structure. The results are analyzed, accepting only those binding sites, which have free-energy and spatial structure similar to that of known binding sites. Since known binding sites of known miRNA genes frequently have multiple adjacent binding sites on the same target RNA, accordingly binding sites which are clustered are strongly preferred. Binding sites found in evolutionarily conserved sequences may preferably also be preferred.

For each candidate binding site a score, Binding Site Prediction Accuracy, is calculated which estimates their similarity of its binding to that of known binding sites. This score is based on GAM-binding site folding features including, but not limited to the free-energy, the total number and distribution of base pairs, the total number and distribution of unpaired nucleotides.

In another preferred embodiment of the present invention binding sites are searched by a reversed process: sequences of K (preferably 22) nucleotides of the untranslated regions of the target gene are assessed as potential binding sites. A sequence comparison algorithm, such as BLAST or EDIT DISTANCE, is then used to search for partially or accurately complementary sequences elsewhere in the genome, which complementary sequences are found in known miRNA genes or computationally predicted GAM genes. Only complementary sequences, the complementarity of which withstands the spatial structure and free energy analysis requirements described above are accepted. Clustered binding sites are strongly favored, as are potential binding sites and potential GAM genes which occur in evolutionarily conserved genomic sequences.

Target binding sites, identified by the TARGET-GENE BINDING-SITE DETECTOR 118, are divided into 3 groups: a) comprises binding sites that are exactly complementary to the predicted GAM. b) and c) comprise binding sites that are not exactly complementary to the predicted GAM: b) has binding sites with 0.9<Binding Site Prediction Accuracy<=1 and c) has binding sites with 0.8<Binding Site Prediction Accuracy<=0.9. The average number of mismatching nucleotides in the alignment of predicted GAM and target binding site is smallest in category A and largest in category C.

In a preferred embodiment of the current invention a ranking of GAM to target gene binding is performed by calculating a score, Mir Target Accuracy. This score is the dominant group identifier of all binding sites of a specific GAM to a specific target gene UTR, where 'a' dominates 'b' and 'b' dominates 'c'.

In yet another preferred embodiment of the current invention a ranking of GAM to target gene binding is performed directly from the set of Binding Site Prediction Accuracies corresponding to all the binding sites of a specific GAM to a specific target gene UTR. This set of scores is sorted in descending order. The final score is a weighted sum of these scores where the weights are exponentially decreasing as a function of the rank.

Figure 15:
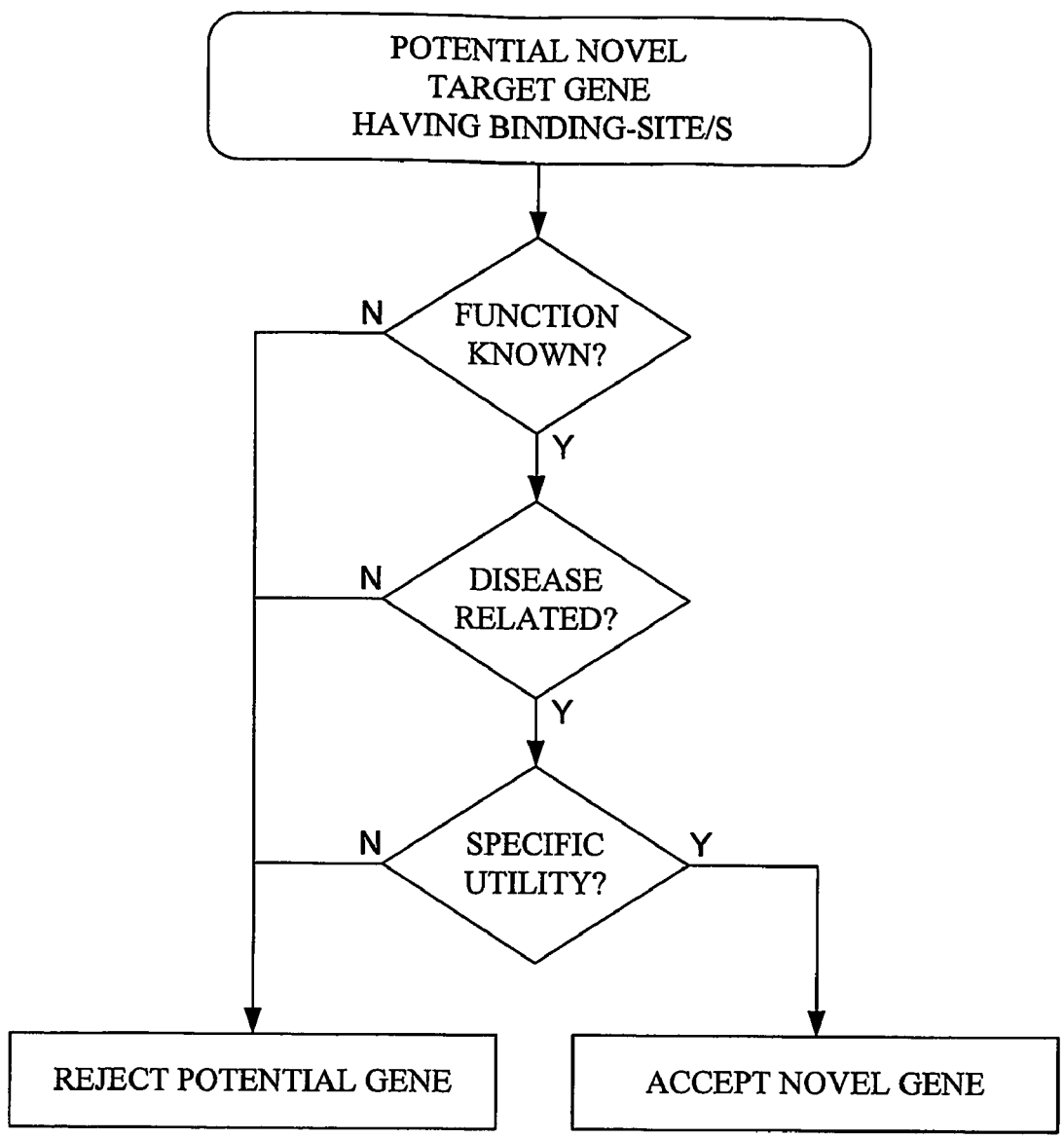
FIG. 15 is a simplified flowchart illustrating operation of a function & utility analyzer constructed and operative in accordance with a preferred embodiment of the present invention.

Reference is now made to FIG. 15 which is a simplified flowchart illustrating a preferred operation of the function & utility analyzer 120 described hereinabove with reference to FIG. 9. The goal of the function & utility analyzer 120 is to determine if a potential target gene is in fact a valid clinically useful target gene. Since a potential novel GAM gene binding a binding site in the UTR of a target gene is understood to inhibit expression of that target gene, and if that target gene is shown to have a valid clinical utility, then in such a case it follows that the potential novel gene itself also has a valid useful function—which is the opposite of that of the target gene.

The function & utility analyzer 120 preferably receives as input a plurality of potential novel target genes having binding-site/s 144, generated by the target-gene binding-site detector 118, both of FIG. 14A. Each potential gene, is evaluated as follows:

First, the system checks to see if the function of the potential target gene is scientifically well established. Preferably, this can be achieved bioinformatically by searching various published data sources presenting information on known function of proteins. Many such data sources exist and are published as is well known in the art.

Next, for those target genes the function of which is scientifically known and is well documented, the system then checks if scientific research data exists which links them to known diseases. For example, a preferred embodiment of the present invention utilizes the OMIM™ database published by NCBI, which summarizes research publications relating to genes which have been shown to be associated with diseases.

Finally, the specific possible utility of the target gene is evaluated. While this process too may be facilitated by bioinformatic means, it might require manual evaluation of published scientific research regarding the target gene, in order to determine the utility of the target gene to the diagnosis and or treatment of specific disease. Only potential novel genes, the target-genes of which have passed all three examinations, are accepted as novel genes.

Figure 16:
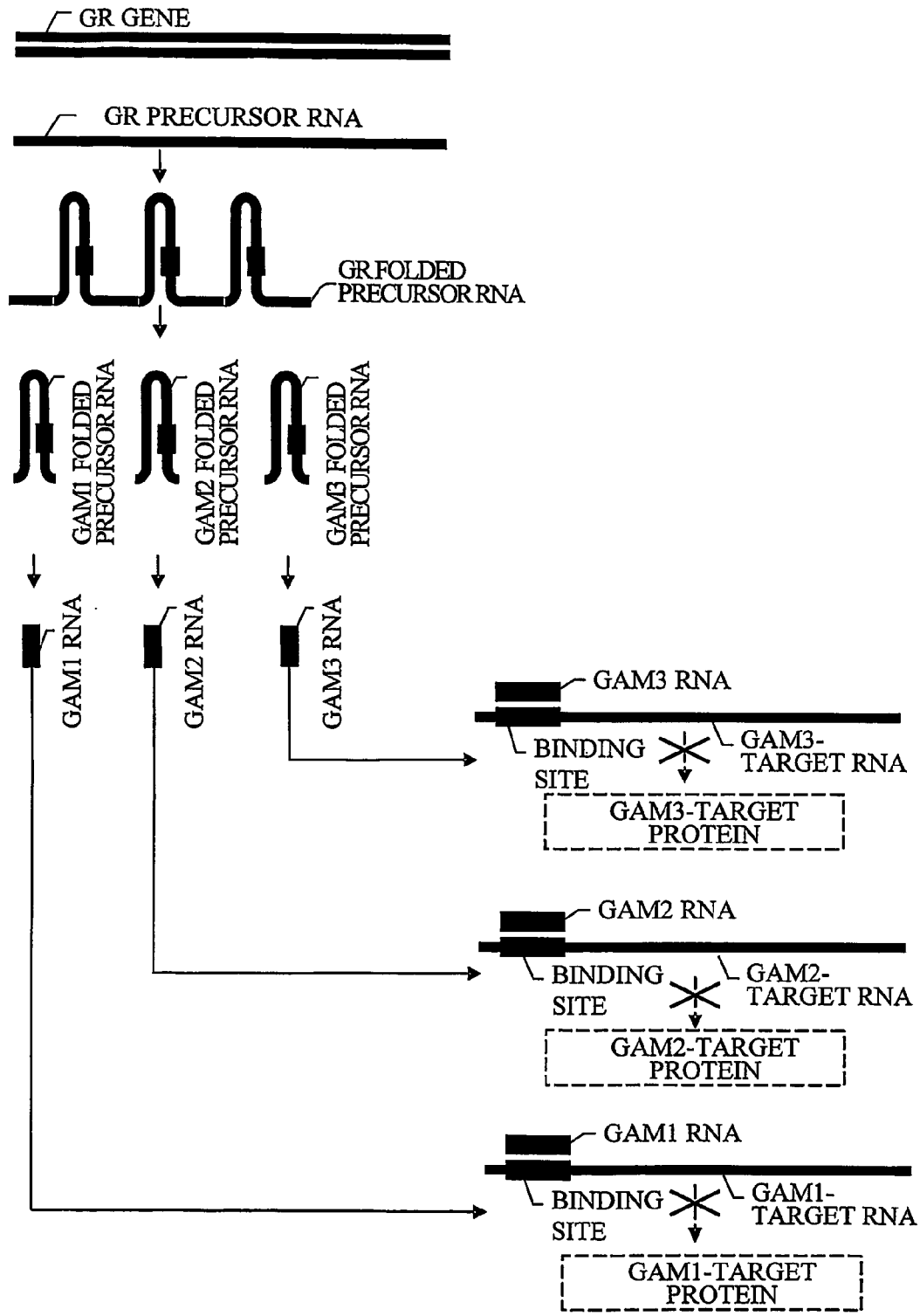
FIG. 16 is a simplified diagram describing a novel bioinformatically detected group of regulatory genes, referred to here as Genomic Record (GR) genes, each of which encodes an 'operon-like' cluster of novel miRNA-like genes, which in turn modulate expression of one or more target genes.

Reference is now made to FIG. 16, which is a simplified diagram describing each of a plurality of novel bioinformatically detected regulatory genes, referred to here as Genomic Record (GR) genes, which encodes an 'operon-like' cluster of novel micro RNA-like genes, each of which in turn modulates expression of at least one target gene, the function and utility of which at least one target gene is known in the art.

GR GENE is a novel bioinformatically detected regulatory, non protein coding, RNA gene. The method by which GR GENE was detected is described hereinabove with reference to FIGS. 9-18.

GR GENE encodes GR PRECURSOR RNA, an RNA molecule, typically several hundred nucleotides long.

GR PRECURSOR RNA folds spatially, forming GR FOLDED PRECURSOR RNA. It is appreciated that GR FOLDED PRECURSOR RNA comprises a plurality of what is known in the art as 'hairpin' structures. These 'hairpin' structures are due to the fact that the nucleotide sequence of GR PRECURSOR RNA comprises a plurality of segments, the first half of each such segment having a nucleotide sequence which is at least a partial or accurate inversed reversed sequence of the second half thereof, as is well known in the art.

GR FOLDED PRECURSOR RNA is naturally processed by cellular enzymatic activity into separate GAM precursor RNAs, herein schematically represented by GAM1 FOLDED PRECURSOR RNA through GAM3 FOLDED PRECURSOR RNA, each of which GAM precursor RNAs being a hairpin shaped RNA segment, corresponding to GAM FOLDED PRECURSOR RNA of FIG. 8.

The above mentioned GAM precursor RNAs are diced by DICER COMPLEX of FIG. 8, yielding respective short RNA segments of about 22 nucleotides in length, schematically represented by GAM1 RNA through GAM3 RNA, each of which GAM RNAs corresponding to GAM RNA of FIG. 8.

GAM1 RNA, GAM2 RNA and GAM3 RNA, each bind complementarily to binding sites located in untranslated regions of respective target genes, designated GAM1-TARGET RNA, GAM2-TARGET RNA and GAM3-TARGET RNA, respectively, which target binding site corresponds to a target binding site such as BINDING SITE I, BINDING SITE II or BINDING SITE III of FIG. 8. This binding inhibits translation of the respective target proteins designated GAM1-TARGET PROTEIN, GAM2-TARGET PROTEIN and GAM3-TARGET PROTEIN respectively.

It is appreciated that specific functions, and accordingly utilities, of each GR GENE of the present invention, correlates with, and may be deduced from, the identity of the target genes, which are inhibited by GAM RNAs comprised in the 'operon-like' cluster of said GR GENE, schematically represented by GAM1 TARGET PROTEIN through GAM3 TARGET PROTEIN.

A listing of GAM GENEs comprised in each of a plurality of GR GENEs of FIG. 16 is provided in Table 7, hereby incorporated by reference. Nucleotide sequences of each said GAM GENEs and their respective genomic source and chromosomal location are further described hereinbelow with reference to Table 1, hereby incorporated by reference. TARGET GENEs of each of said GAM GENEs are elaborated hereinbelow with reference to Table 4, hereby incorporated by reference. The functions of each of said TARGET GENEs and their association with various diseases, and accordingly the utilities of said each of GAM GENEs, and hence the functions and utilities of each of said GR GENEs of FIG. 16 is elaborated hereinbelow with reference to Table 5, hereby incorporated by reference. Studies establishing known functions of each of said TARGET GENEs, and correlation of each of said TARGET GENEs to known diseases are listed in table 6, and are hereby incorporated by reference.

The present invention discloses 1096 novel genes of the GR group of genes, which have been detected bioinformatically, as elaborated hereinbelow with reference to Table 7. Laboratory confirmation of 2 genes of the GR group of genes is described hereinbelow with reference to FIGS. 23A through 24C.

In summary, the current invention discloses a very large number of novel GR genes, each of which encodes a plurality of GAM genes, which in turn may modulate expression of a plurality of target proteins. It is appreciated therefore that the function of GR genes is in fact similar to that of the Genomic Records concept of the present invention addressing the differentiation enigma, described hereinabove with reference to FIG. 7.

Figure 17:
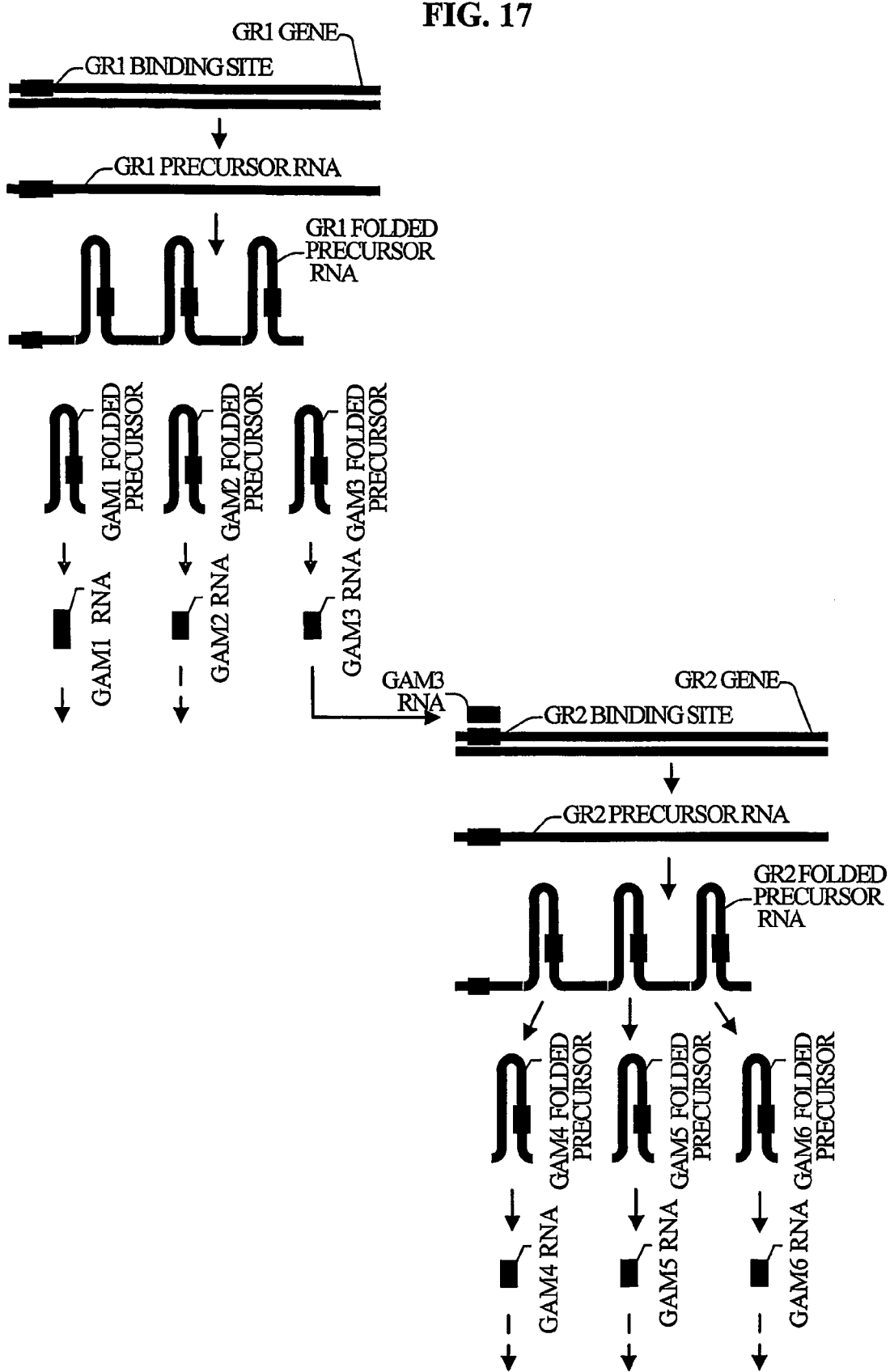
FIG. 17 is a simplified diagram illustrating a mode by which genes of a novel group of operon-like genes of the present invention, modulate expression of other such genes, in a cascading manner.

Reference is now made to FIG. 17 which is a simplified diagram illustrating a mode by which genes of a novel group of operon-like genes, described hereinabove with reference to FIG. 16 of the present invention, modulate expression of other such genes, in a cascading manner.

GR1 GENE and GR2 GENE are two genes of the novel group of operon-like genes designated GR of FIG. 16. As is typical of genes of the GR group of genes, GR1 and GR2 each encode a long RNA precursor, which in turn folds into a folded RNA precursor comprising multiple hairpin shapes, and is cut into respective separate hairpin shaped RNA segments, each of which RNA segments being diced to yield a gene of a group of genes designated GAM of FIG. 8. In this manner GR1 yields GAM1 RNA, GAM2 RNA and GAM3 RNA, and GR2 yields GAM4 RNA, GAM5 RNA and GAM6 RNA.

As FIG. 17 shows, GAM3 RNA, which derives from GR1, binds a binding site located adjacent to GR2 GENE, thus modulating expression of GR2, thereby invoking expression of GAM4 RNA, GAM5 RNA and GAM6 RNA which derive from GR2.

It is appreciated that the mode of modulation of expression presented by FIG. 17 enables an unlimited 'cascading effect' in which a GR gene comprises multiple GAM genes, each of which may modulate expression of other GR genes, each such GR gene comprising additional GAM genes, etc., whereby eventually certain GAM genes modulate expression of target proteins. This mechanism is in accord with the conceptual model of the present invention addressing the differentiation enigma, described hereinabove with specific reference to FIGS. 6 and 7.

Figure 18:
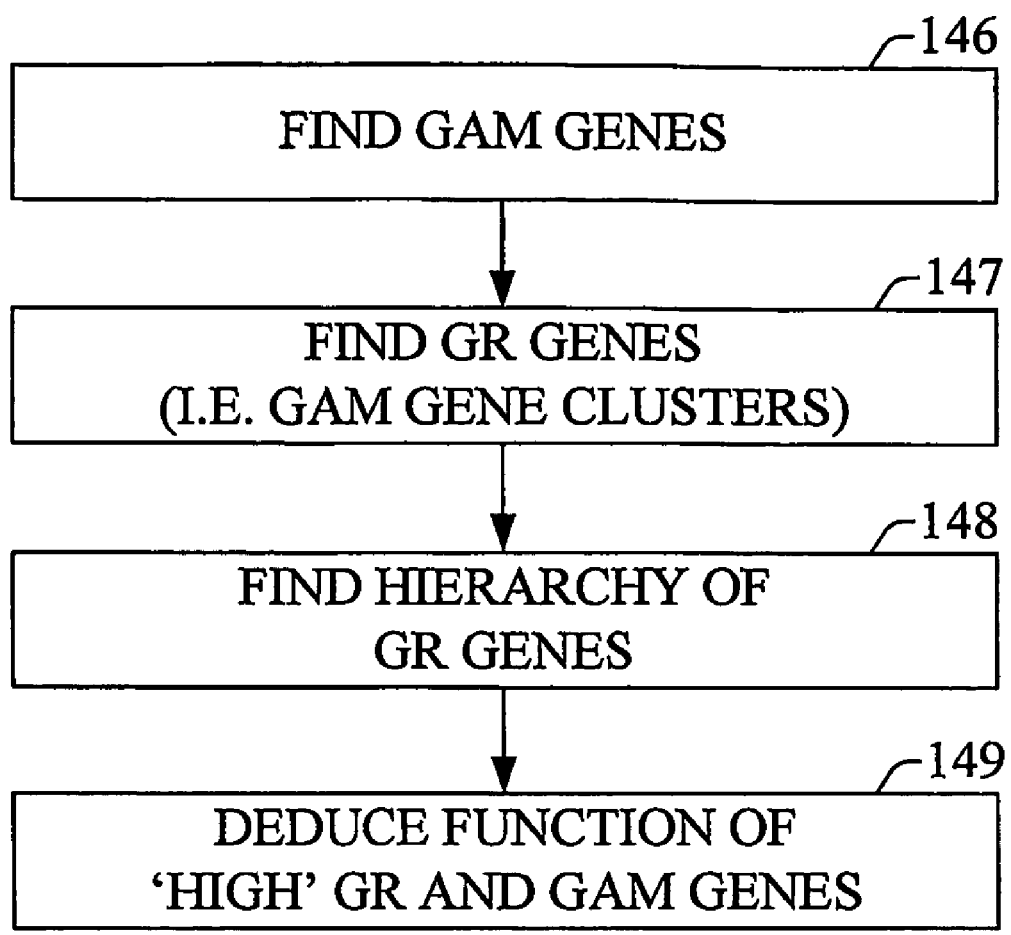
FIG. 18 is a block diagram illustrating an overview of a methodology for finding novel genes and novel operon-like genes of the present invention, and their respective functions.

Reference is now made to FIG. 18 which is a block diagram illustrating an overview of a methodology for finding novel genes and operon-like genes of the present invention, and their respective functions.

According to a preferred embodiment of the present invention, the methodology to finding novel genes of the present invention and their function comprises of the following major steps:

First, genes of the novel group of genes of the present invention, referred to here as GAM genes, as designated by reference numeral 146, are located and their function elicited by detecting target proteins they bind and the function of those target proteins, as described hereinabove with reference to FIGS. 9 through 15.

Next, genes of a novel group of operon-like genes of the present invention, referred to here as GR genes, as designated by reference numeral 147, are located, by locating clusters of proximally located GAM genes, based on the previous step.

Consequently, the hierarchy of GR and GAM genes is elicited, as designated by reference numeral 148: binding sites for non-protein-binding GAM genes comprised in each GR gene found are sought adjacent to other GR genes. When found, such a binding site indicates that the connection between the GAM and the GR the expression of which it modulates, and thus the hierarchy of the GR genes and the GAM genes they comprise.

Lastly, the function of GR genes and GAM genes which are 'high' in the hierarchy, i.e. GAM genes which modulate expression of other GR genes rather than directly modulating expression of target proteins, may be deduced. A preferred approach is as follows: The function of protein-modulating GAM genes is deducible from the protein which they modulate, provided that the function of these target proteins is known. The function of 'higher' GAM genes may be deduced by comparing the function of protein-modulating GAM genes, as designated by reference numeral 149, with the hierarchical relationships by which the 'higher' GAM genes are connected of the protein-modulating GAM genes. For example, given a group of several protein-modulating GAM genes, which collectively cause a protein expression pattern typical of a certain cell-type, then a 'higher' GAM gene is sought which modulates expression of GR genes, which perhaps modulate expression of other genes which eventually modulate expression of the given group of protein-modulating GAM genes. The 'higher' GAM gene found in this manner is taken to be responsible for differentiation of that cell-type, as per the conceptual model of the invention described hereinabove with reference to FIG. 6

Figure 19:
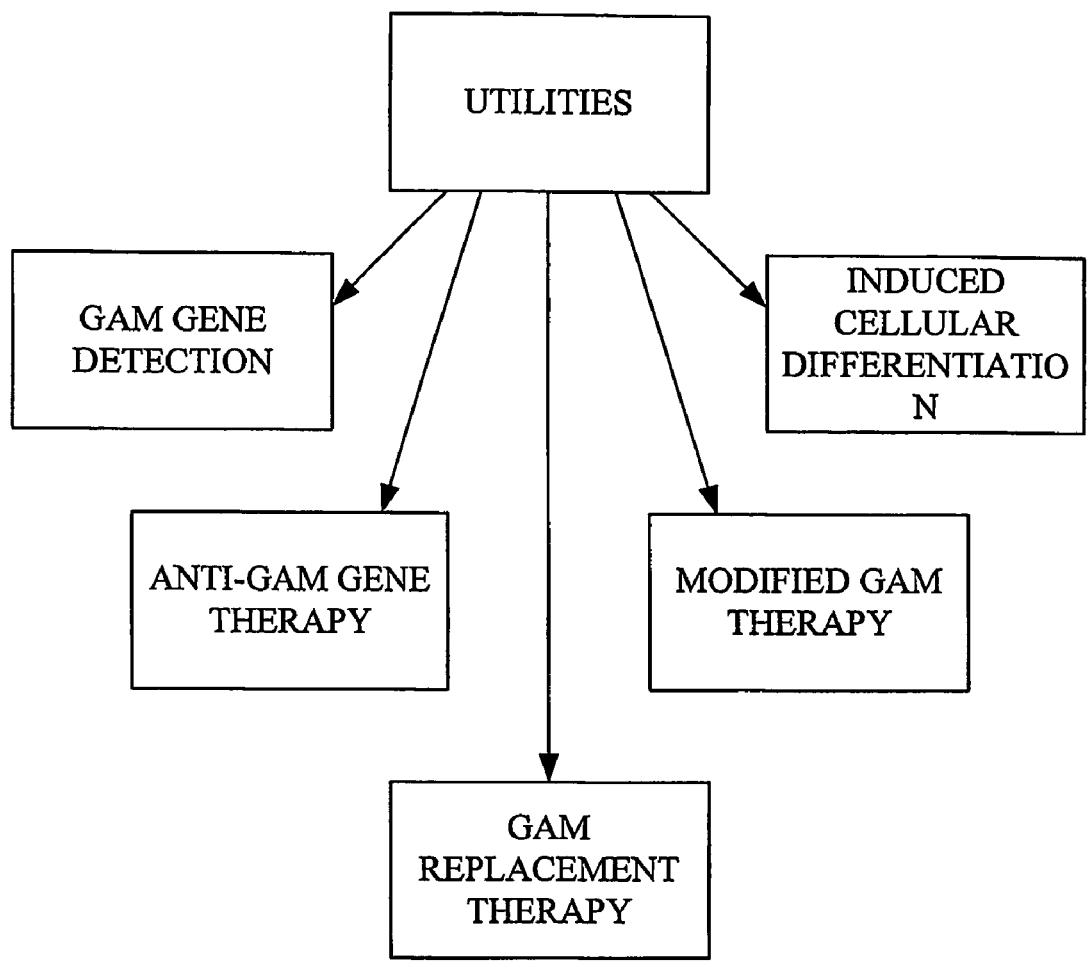
FIG. 19 is a block diagram illustrating different utilities of novel genes and novel operon-like genes, both of the present invention.

Reference is now made to FIG. 19 which is a block diagram illustrating different utilities of genes of the novel group of genes of the present invention referred to here as GAM genes and GR genes.

The present invention discloses a first plurality of novel genes referred to here as GAM genes, and a second plurality of operon-like genes referred to here as GR genes, each of the GR genes encoding a plurality of GAM genes. The present invention further discloses a very large number of known target-genes, which are bound by, and the expression of which is modulated by each of the novel genes of the present invention. Published scientific data referenced by the present invention provides specific, substantial, and credible evidence that the above mentioned target genes modulated by novel genes of the present invention, are associated with various diseases. Specific novel genes of the present invention, target genes thereof and diseases associated therewith, are described hereinbelow with reference to Tables 1 through 7. It is therefore appreciated that a function of GAM genes and GR genes of the present invention is modulation of expression of target genes related to known diseases, and that therefore utilities of novel genes of the present invention include diagnosis and treatment of the above mentioned diseases. FIG. 19 describes various types of diagnostic and therapeutic utilities of novel genes of the present invention.

A utility of novel genes of the present invention is detection of GAM genes and of GR genes. It is appreciated that since GAM genes and GR genes modulate expression of disease related target genes, that detection of expression of GAM genes in clinical scenarios associated with said diseases is a specific, substantial and credible utility. Diagnosis of novel genes of the present invention may preferably be implemented by RNA expression detection techniques, including but not limited to biochips, as is well known in the art. Diagnosis of expression of genes of the present invention may be useful for research purposes, in order to further understand the connection between the novel genes of the present invention and the above mentioned related diseases, for disease diagnosis and prevention purposes, and for monitoring disease progress.

Another utility of novel genes of the present invention is anti-GAM gene therapy, a mode of therapy which allows up regulation of a disease related target-gene of a novel GAM gene of the present invention, by lowering levels of the novel GAM gene which naturally inhibits expression of that target gene. This mode of therapy is particularly useful with respect to target genes which have been shown to be under-expressed in association with a specific disease. Anti-GAM gene therapy is further discussed hereinbelow with reference to FIGS. 20A and 20B.

A further utility of novel genes of the present invention is GAM replacement therapy, a mode of therapy which achieves down regulation of a disease related target-gene of a novel GAM gene of the present invention, by raising levels of the GAM gene which naturally inhibits expression of that target gene. This mode of therapy is particularly useful with respect to target genes which have been shown to be over-expressed in association with a specific disease. GAM replacement therapy involves introduction of supplementary GAM gene products into a cell, or stimulation of a cell to produce excess GAM gene products. GAM replacement therapy may preferably be achieved by transfecting cells with an artificial DNA molecule encoding a GAM gene, which causes the cells to produce the GAM gene product, as is well known in the art. Yet a further utility of novel genes of the present invention is modified GAM therapy. Disease conditions are likely to exist, in which a mutation in a binding site of a GAM gene prevents natural GAM gene to effectively bind inhibit a disease related target-gene, causing up regulation of that target gene, and thereby contributing to the disease pathology. In such conditions, a modified GAM gene is designed which effectively binds the mutated GAM binding site, i.e. is an effective anti-sense of the mutated GAM binding site, and is introduced in disease effected cells. Modified GAM therapy is preferably achieved by transfecting cells with an artificial DNA molecule encoding the modified GAM gene, which causes the cells to produce the modified GAM gene product, as is well known in the art.

An additional utility of novel genes of the present invention is induced cellular differentiation therapy. As aspect of the present invention is finding genes which determine cellular differentiation, as described hereinabove with reference to FIG. 18. Induced cellular differentiation therapy comprises transfection of cell with such GAM genes thereby determining their differentiation as desired. It is appreciated that this approach may be widely applicable, inter alia as a means for auto transplantation harvesting cells of one cell-type from a patient, modifying their differentiation as desired, and then transplanting them back into the patient. It is further appreciated that this approach may also be utilized to modify cell differentiation in vivo, by transfecting cells in a genetically diseased tissue with a cell-differentiation determining GAM gene, thus stimulating these cells to differentiate appropriately.

Figure 20A:
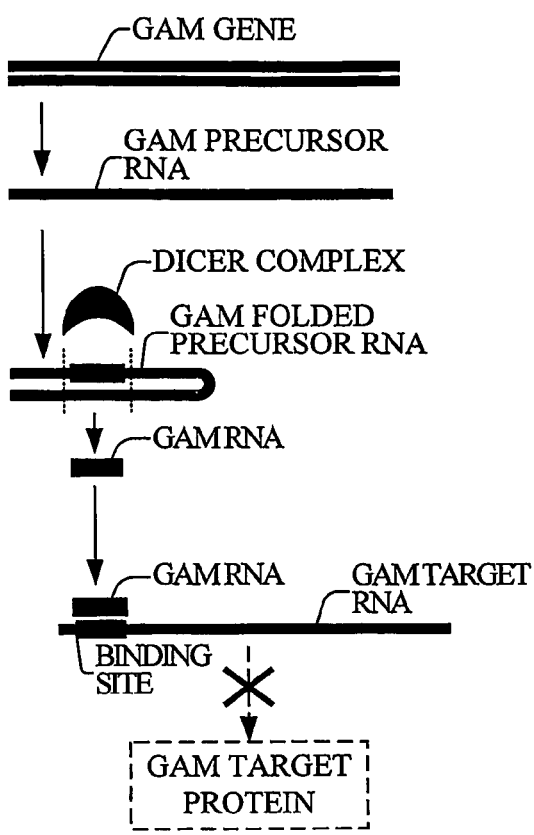
FIGS. 20A and 20B are simplified diagrams, which when taken together illustrate a mode of gene therapy applicable to novel genes of the present invention.
Figure 20B:
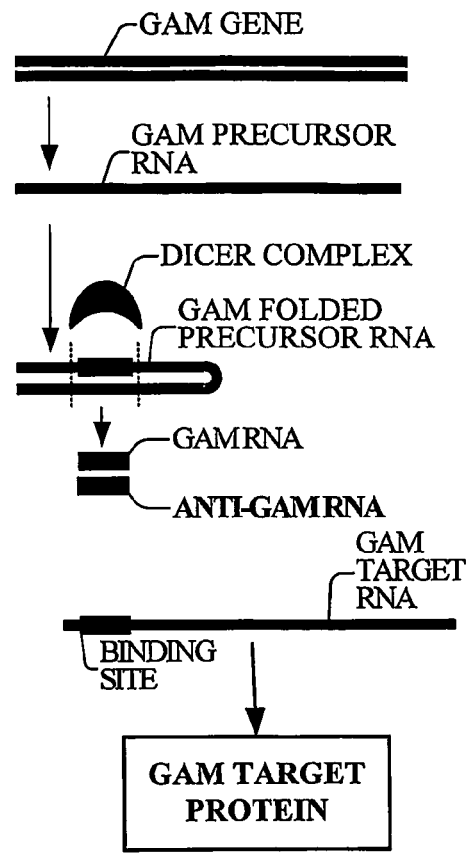

Reference is now made to FIGS. 20A and 20B, simplified diagrams which when taken together illustrate anti-GAM gene therapy mentioned hereinabove with reference to FIG. 19. A utility of novel genes of the present invention is anti-GAM gene therapy, a mode of therapy which allows up regulation of a disease related target-gene of a novel GAM gene of the present invention, by lowering levels of the novel GAM gene which naturally inhibits expression of that target gene. FIG. 20A shows a normal GAM gene, inhibiting translation of a target gene of GAM gene, by binding to a BINDING SITE found in an untranslated region of GAM TARGET RNA, as described hereinabove with reference to FIG. 8.

FIG. 20B shows an example of anti-GAM gene therapy. ANTI-GAM RNA is short artificial RNA molecule the sequence of which is an anti-sense of GAM RNA. Anti-GAM treatment comprises transfecting diseased cells with ANTI-GAM RNA, or with a DNA encoding thereof. The ANTI-GAM RNA binds the natural GAM RNA, thereby preventing binding of natural GAM RNA to its BINDING SITE. This prevents natural translation inhibition of GAM TARGET RNA by GAM RNA, thereby up regulating expression of GAM TARGET PROTEIN.

It is appreciated that anti-GAM gene therapy is particularly useful with respect to target genes which have been shown to be under-expressed in association with a specific disease.

Furthermore, anti-GAM therapy is particularly useful, since it may be used in situations in which technologies known in the art as RNAi and siRNA can not be utilized. As in known in the art, RNAi and siRNA are technologies which offer means for artificially inhibiting expression of a target protein, by artificially designed short RNA segments which bind complementarily to mRNA of said target protein. However, RNAi and siRNA can not be used to directly upregulate translation of target proteins.

Reference is now made to FIG. 21, which is a table summarizing laboratory validation results that validate efficacy of the bioinformatic gene detection engine 100 of FIG. 9. In order to assess efficacy of the bioinformatic gene detection engine 100, novel genes predicted thereby are preferably divided into 4 DETECTION ACCURACY GROUPS (first column), designated A through D, ranking GAMS from the most probable GAMs to the least probable GAMs, using the scores of HAIRPIN DETECTOR 114 and DICER-CUT LOCATION DETECTOR 116 as follows:

Group A: The score of the HAIRPIN-DETECTOR is above 0.7, the overall score of the two-phased predictor is above 0.55, and the score of the second phase of the two-phased predictor is above 0.75. Group B: The score of the EDIT-DISTANCE predictor is equal or above 17. In both groups A and B one miRNA is predicted for each hairpin. Group C: The score of the HAIRPIN-DETECTOR is between 0.6 and 0.7, and the overall score of the two-phased predictor is above 0.55. Group D: The score of the HAIRPIN-DETECTOR is between 0.3 and 0.6, and the overall score of the two-phased predictor is above 0.55. In both groups C and D, for each hairpin both sides of the double stranded window are given as output, and are examined in the lab. The groups are mutually exclusive, i.e. in groups A, C and D all hairpins score less than 17 in the EDIT-DISTANCE predictor. It is appreciated that the division into groups is not exhaustive: 344 of the 440 published hairpins, and 4747 of the 8607 novel GAMs of the present invention, belong to one of the groups.

Sample novel bioinformatically predicted genes, of each of these groups are sent to the laboratory for validation (third column), and the number (fourth column) and percent (fifth column) of successful validation of predicted genes is noted for each of the groups, as well as overall (bottom line). The number of novel genes explicitly specified by present invention belonging to each of the four groups is noted (sixth column), as is the number of novel genes found in intergenic and intronic RNA (seventh and eighth columns). Expected positives (eighth column) is deduced by multiplying the % success in the lab validation by the number of novel GAMs detected in intronic and intergenic RNA databases.

It is appreciated that the present invention comprises 4747 novel GAM genes, which fall into one of these four detection accuracy groups, and that the bioinformatic prediction is substantiated by a group of 50 novel GAM genes validated by laboratory means, out of 147 genes which were tested in the lab, resulting in validation of an overall 34% accuracy. The top group demonstrated 50% accuracy. Pictures of test-results of specific genes in the abovementioned four groups, as well as the methodology used for validating the expression of predicted genes is elaborated hereinbelow with reference to FIG. 22.

It is further appreciated that failure to detect a gene in the lab does not necessarily indicate a mistaken bioinformatic prediction. Rather, it may be due to technical sensitivity limitation of the lab test, or because the gene is not expressed in the tissue examined, or at the development phase tested.

It is still further appreciated that in general these findings are in agreement with the expected bioinformatic accuracy, as describe hereinabove with reference to FIG. 13B: assuming 80% accuracy of the hairpin detector 114 and 80% accuracy of the dicer-cut location detector 116 and 80% accuracy of the lab validation, this would result in 50% overall accuracy of the genes validated in the lab.

Figure 22:
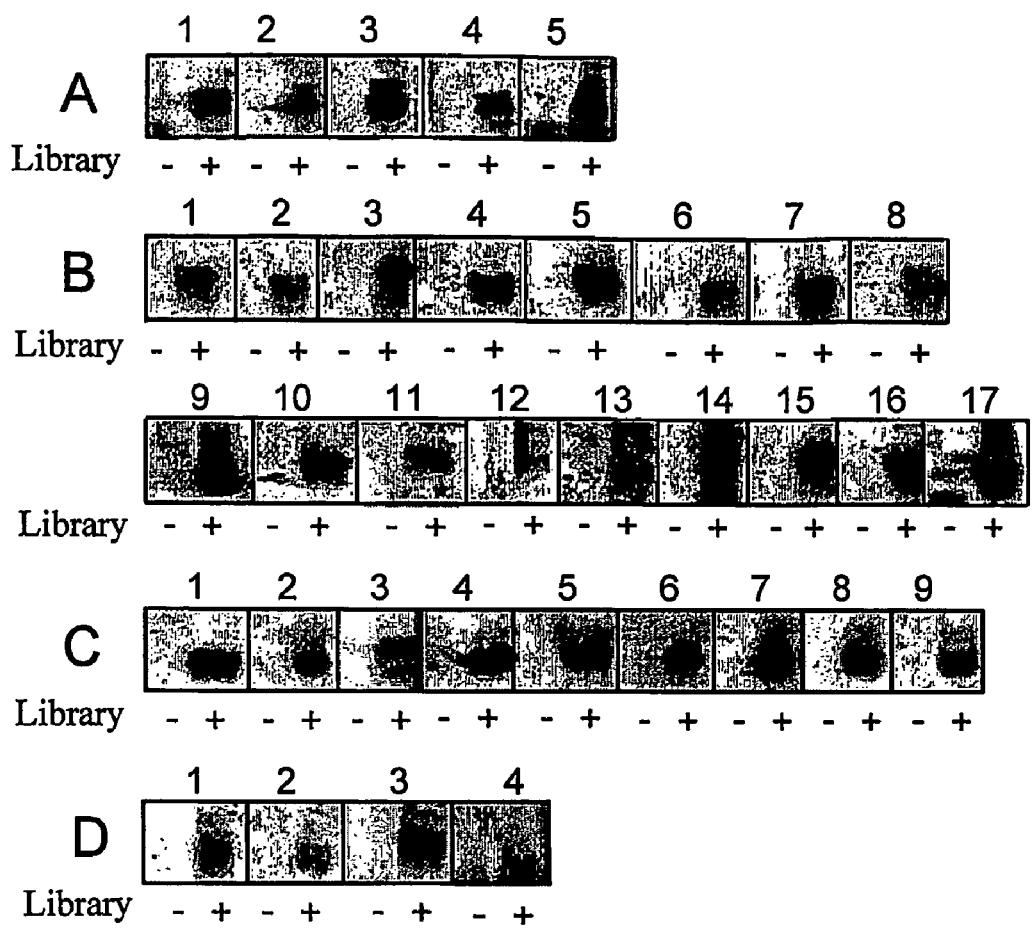
FIG. 22 is a picture of laboratory results validating the expression of 25 novel genes detected by a bioinformatic gene detection engine constructed and operative in accordance with a preferred embodiment of the present invention, thereby validating the efficacy of the gene detection engine of the present invention.

Reference is now made to FIG. 22 which is a picture of laboratory results validating the expression of 25 novel genes detected by the bioinformatic gene detection engine 100, in the four detection accuracy groups A through D described hereinabove with reference to FIG. 21.

Each row in FIG. 22, designated A through D, correlates to a corresponding one of the four detection accuracy groups A-D, described hereinabove with reference to FIG. 21. In each row, pictures of several genes validated by hybridization of PCR-product southern-blots, are provided, each corresponding to a specific GAM gene, as elaborated hereinbelow. These PCR-product hybridization pictures are designated 1 through 5 in the A group, 1 through 12 in the B group, 1 through 9 in the C group, and 1 through 4 in the D group. In each PCR hybridization picture, 2 lanes are seen: the test lane, designated '+' and the control lane, designated '−'. For convenience of viewing the results, all PCR-product hybridization pictures of FIG. 22 have been shrunk ×4 vertically. It is appreciated that for each of the tested genes, a clear hybridization band appears in the test ('+') lane, but not in the control ('−') lane.

Specifically, FIG. 22 shows pictures of PCR-product hybridization validation by southern-blot, the methodology of which is described hereinbelow, to the following novel GAM genes:

DETECTION ACCURACY GROUP A: (1) GAM8297.1; (2) GAM5346.1; (3) GAM281.1; (4) GAM8554.1; and (5) GAM2071.1.

DETECTION ACCURACY GROUP B: (1) GAM7553.1; (2) GAM5385.1; (3) GAM5227.1; (4) GAM7809.1; (5) GAM1032.1; (6) GAM3431.1; (7) GAM7933.1; (8) GAM3298.1; (9) GAM116.1; (10) GAM3418.1 (later published by other researchers as MIR23); (11) GAM3499.1; (12) GAM3027.1; (13) GAM7080.1; (14) GAM895.1; and (15) GAM2608.1, (16) GAM20, and (17) GAM21.

DETECTION ACCURACY GROUP C: (1) GAM3770.1; (2) GAM1338.1; (3) GAM7957.1; (4) GAM391.1; (5) GAM 8678.1; (6) GAM2033.1; (7) GAM7776.1; (8) GAM8145.1; and (9) GAM 633.1.

DETECTION ACCURACY GROUP D: (1) GAM19; (2) GAM8358.1; (3) GAM3229.1; and (4) GAM7052.1.

In addition to the PCR detection, the following GAMs were cloned and sequenced: GAM1338.1, GAM7809.1, GAM116.1, GAM3418.1 (later published by other researchers as MIR23), GAM3499.1, GAM3027.1, GAM7080.1, and GAM21.

The PCR-product hybridization validation methodology used is briefly described as follows. In order to validate the expression of predicted novel GAM genes, and assuming that these novel genes are probably expressed at low concentrations, a PCR product cloning approach was set up through the following strategy: two types of cDNA libraries designated "One tailed" and "Ligation" were prepared from frozen HeLa S100 extract (4c Biotech, Belgium) size fractionated RNA. Essentially, Total S100 RNA was prepared through an SDS-Proteinase K incubation followed by an acid Phenol-Chloroform purification and Isopropanol precipitation. Alternatively, total HeLa RNA was also used as starting material for these libraries.

Fractionation was done by loading up to 500 µg per YM100 Amicon Microcon column (Millipore) followed by a 500 g centrifugation for 40 minutes at 4° C. Flowthrough "YM100" RNA consisting of about ¼ of the total RNA was used for library preparation or fractionated further by loading onto a YM30 Amicon Microcon column (Millipore) followed by a 13,500 g centrifugation for 25 minutes at 4° C. Flowthrough "YM30" was used for library preparation as is and consists of less than 0.5% of total RNA. For the both the "ligation" and the "One-tailed" libraries RNA was dephosphorilated and ligated to an RNA (lowercase)-DNA (UPPERCASE) hybrid 5'-phosphorilated, 3' idT blocked 3'-adapter (5'-P-uuuAAC-CGCATTCTC-idT-3' Dharmacon # P-002045-01-05) (SEQ ID NO: 548157) (as elaborated in Elbashir et al 2001) resulting in ligation only of RNase III type cleavage products. 3'-Ligated RNA was excised and purified from a half 6%, half 13% polyacrylamide gel to remove excess adapter with a Nanosep 0.2 µM centrifugal device (Pall) according to instructions, and precipitated with glycogen and 3 volumes of Ethanol. Pellet was resuspended in a minimal volume of water. For the "ligation" library a DNA (UPPERCASE)-RNA (lowercase) hybrid 5'-adapter (5'-TACTAATACGACTCAC-Taaa-3' Dharmacon # P-002046-01-05) (SEQ ID NO: 548158) was ligated to the 3'-adapted RNA, reverse transcribed with "EcoRI-RT": (5'-GACTAGCTGGAAT-TCAAGGATGCGGTTAAA-3') (SEQ ID NO: 548159), PCR amplified with two external primers essentially as in Elbashir et al 2001 except that primers were "EcoRI-RT" and "PstI Fwd" (5'-CAGCCAACGCTGCAGATACGACTCAC-TAAA-3') (SEQ ID NO: 548160). This PCR product was used as a template for a second round of PCR with one hemispecific and one external primer or with two hemispecific primers.

For the "One tailed" library the 3'-Adapted RNA was annealed to 20 pmol primer "EcRI RT" by heating to 70° C. and cooling 0.1° C./sec to 30° C. and then reverse transcribed with Superscript II RT (According to instructions, Invitrogen) in a 20 µl volume for 10 alternating 5 minute cycles of 37° C. and 45° C. Subsequently, RNA was digested with 1 µl 2M NaOH, 2 mM EDTA at 65° C. for 10 minutes. cDNA was loaded on a polyacrylamide gel, excised and gel-purified from excess primer as above (invisible, judged by primer run alongside) and resuspended in 13 µl of water. Purified cDNA was then oligo-dC tailed with 400 U of recombinant terminal transferase (Roche molecular biochemicals), 1 µl 100 µM dCTP, 1 µl 15 mM $CoCl_2$, and 4 µl reaction buffer, to a final volume of 20 µl for 15 minutes at 37° C. Reaction was stopped with 2 µl 0.2M EDTA and 15 µl 3M NaOAc pH 5.2. Volume was adjusted to 150 µl with water, Phenol:Bromochloropropane 10:1 extracted and subsequently precipitated with glycogen and 3 volumes of Ethanol. C-tailed cDNA was used as a template for PCR with the external primers "T3-PstBsg(G/I)$_{18}$" (5'-AATTAACCCTCACTAAAGGCTGCAGGTGC AGGIGGGIIGGGIIGGGIIGN-3' [SEQ ID NO: 548161] where I stands for Inosine and N for any of the 4 possible deoxynucleotides), and with "EcoRI Nested" (5'-GGAAT-TCAAGGATGCGGTTA-3') (SEQ ID NO: 548162). This PCR product was used as a template for a second round of PCR with one hemispecific and one external primer or with two hemispecific primers.

Hemispecific primers were constructed for each predicted GAM by an in-house program designed to choose about half of the 5' or 3' sequence of the GAM corresponding to a TM° of about 30°-34° C. constrained by an optimized 3' clamp, appended to the cloning adapter sequence (for "One-tailed" libraries 5'-GGNNGGGNNG (SEQ ID NO: 548163), on the 5' end of the GAM, or TTTAACCGCATC-3' (SEQ ID NO: 548164), on the 3' end of the GAM. For "Ligation" libraries the same 3' adapter and 5'-CGACTCACTAAA (SEQ ID NO: 548165) on the 5' end). Consequently, a fully complementary primer of a TM° higher than 60° C. was created covering only one half of the GAM sequence permitting the unbiased elucidation by sequencing of the other half.

Confirmation of GAM Sequence Authenticity of PCR Products:

SOUTHERN BLOT: PCR-product sequences were confirmed by southern blot (Southern EM. Biotechnology. 1992; 24:122-39. (1975)) and hybridization with DNA oligonucleotide probes synthesized against predicted GAMs. Gels were transferred onto a Biodyne PLUS 0.45 µm, (Pall) positively charged nylon membrane and UV cross-linked. Hybridization was performed overnight with DIG-labeled probes at 42° C. in DIG Easy-Hyb buffer (Roche). Membranes were washed twice with 2×SSC and 0.1% SDS for 10 min. at 42° C. and then washed twice with 0.5×SSC and 0.1% SDS for 5 min at 42° C. The membrane was then developed by using a DIG luminescent detection kit (Roche) using anti-DIG and CSPD reaction, according to the manufacturer's protocol. All probes were prepared according to the manufacturers (Roche Molecular Biochemicals) protocols: Digoxigenin (DIG) labeled antisense transcripts was prepared from purified PCR products using a DIG RNA labeling kit with T3 RNA polymerase. DIG labeled PCR was prepared by using a DIG PCR labeling kit. 3'-DIG-tailed oligo ssDNA antisense probes, containing DIG-dUTP and dATP at an average tail length of 50 nucleotides were prepared from 100 pmole oligonucleotides with the DIG Oligonucleotide Labeling Kit.

CLONING: PCR products were inserted into pGEM-T (Promega) or pTZ57 (MBI Fermentas), transformed into competent JM109 *E. coli* (Promega) and sown on LB-Amp plates with IPTG/Xgal. White and light-blue colonies were transferred to duplicate gridded plates, one of which was blotted onto a membrane (Biodyne Plus, Pall) for hybridization with DIG tailed oligo probes (according to instructions, Roche) corresponding to the expected GAM. Plasmid DNA from positive colonies was sequenced.

Figures 23A, 23B, 23C:
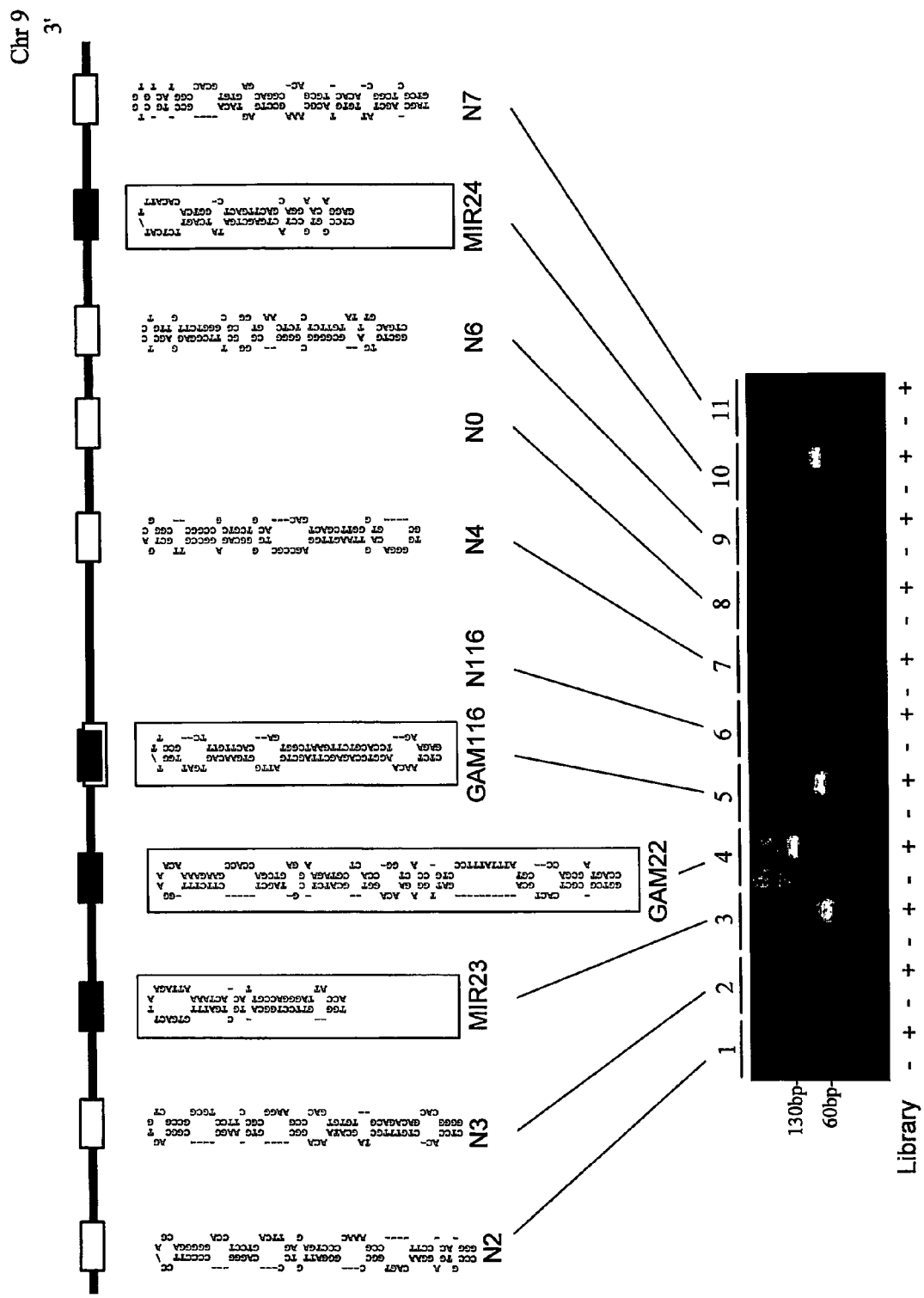
FIG. 23A is a schematic representation of an 'operon like' cluster of novel gene hairpin sequences detected bioinformatically by a bioinformatic gene detection engine constructed and operative in accordance with a preferred embodiment of the present invention, and non-GAM hairpin useful as negative controls thereto.
FIG. 23B is a schematic representation of secondary folding of hairpins of the operon-like cluster of FIG. 23A. The hairpins are associated with the following SEQ ID NOs: N2 (SEQ ID NO: 548172): N3 (SEQ ID NO: 548173): MIR23 (SEQ ID NO: 548174): GAM22 (SEQ ID NO: 548175): GAM116 (SEQ ID NO: 548176): N4 (SEQ ID NO: 548177): N6 (SEQ ID NO: 548178): MIR24 (SEQ ID NO: 548179): N7 (SEQ ID NO: 548180)
FIG. 23C is a picture of laboratory results demonstrating expression of novel genes of FIGS. 23A and 23B, and lack of expression of the negative controls, thereby validating efficacy of bioinformatic detection of GAM genes and GR genes of the present invention, by a bioinformatic gene detection engine constructed and operative in accordance with a preferred embodiment of the present invention.

Reference is now made to FIG. 23A, which is a schematic representation of a novel human GR gene, herein designated GR12731, located on chromosome 9, comprising 2 known MIR genes—MIR24 and MIR23, and 2 novel GAM genes, herein designated GAM22 and GAM116, all marked by solid black boxes. FIG. 23A also schematically illustrates 6 non-GAM hairpin sequences, and one non-hairpin sequence, all marked by white boxes, and serving as negative controls. By 'non-GAM hairpin sequences' is meant sequences of a similar length to known MIR PRECURSOR sequences, which form hairpin secondary folding pattern similar to MIR PRE-CURSOR hairpins, and yet which are assessed by the bioinformatic gene detection engine 100 not to be valid GAM PRECURSOR hairpins. It is appreciated that FIG. 23A is a simplified schematic representation, reflecting only the order in which the segments of interest appear relative to one another, and not a proportional distance between the segments.

Reference is now made to FIG. 23B, which is a schematic representation of secondary folding of each of the MIRs and GAMs of GR GR12731—MIR24, M23, GAM22 and GAM116, and of the negative control non-GAM hairpins, herein designated N2, N3, N116, N4, N6 and N7. N0 is a non-hairpin control, of a similar length to that of known MIR PRECURSOR hairpins. It is appreciated that the negative controls are situated adjacent to and in between real MIR and GAM genes, and demonstrates similar secondary folding patterns to that of known MIRs and GAMs.

Reference is now made to FIG. 23C, which is a picture of laboratory results of a PCR test upon a YM100 "ligation"-library, utilizing specific primer sets directly inside the boundaries of the hairpins. Due to the nature of the library the only PCR amplifiable products can result from RNaseRIII type enzyme cleaved RNA, as expected for legitimate hairpin precursors presumed to be produced by DROSHA (Lee et al, Nature 425 415-419, 2003). FIG. 23C demonstrates expression of hairpin precursors of known MIR genes—MIR23 and MIR4, and of novel bioinformatically detected GAM22 and GAM116 genes predicted bioinformatically by a system constructed and operative in accordance with a preferred embodiment of the present invention. FIG. 23C also shows that none of the 7 controls (6 hairpins designated N2, N3, N23, N4, N6 and N7 and 1 non-hairpin sequence designated N0) were expressed. N116 is a negative control sequence partially overlapping GAM116.

In the picture, test lanes including template are designated '+' and the control lane is designated '−'. It is appreciated that for each of the tested hairpins, a clear PCR band appears in the test ('+') lane, but not in the control ('−') lane.

FIGS. 23A through 23C, when taken together validate the efficacy of the bioinformatic gene detection engine in: (a) detecting known MIR genes; (b) detecting novel GAM genes which are found adjacent to these MIR genes, and which despite exhaustive prior biological efforts and bioinformatic detection efforts, went undetected; (c) discerning between GAM (or MIR) PRECURSOR hairpins, and non-GAM hairpins.

It is appreciated that the ability to discern GAM-hairpins from non-GAM-hairpins is very significant in detecting GAM genes, since hairpins in general are highly abundant in the genome. Other MIR prediction programs have not been able to address this challenge successfully.

Reference is now made to FIG. 24A which is an annotated sequence of an EST comprising a novel gene detected by the gene detection system of the present invention. FIG. 24A shows the nucleotide sequence of a known human non-protein coding EST (Expressed Sequence Tag), identified as EST72223. The EST72223 clone obtained from TIGR database (Kirkness and Kerlavage, 1997) was sequenced to yield the above 705 bp transcript with a polyadenyl tail. It is appreciated that the sequence of this EST comprises sequences of one known miRNA gene, identified as MIR98, and of one novel GAM gene, referred to here as GAM25, detected by the bioinformatic gene detection system of the present invention and described hereinabove with reference to FIG. 9.

The sequences of the precursors of the known MIR98 and of the predicted GAM25 are in bold, the sequences of the established miRNA 98 and of the predicted miRNA GAM25 are underlined.

Figures 24B, 24C:
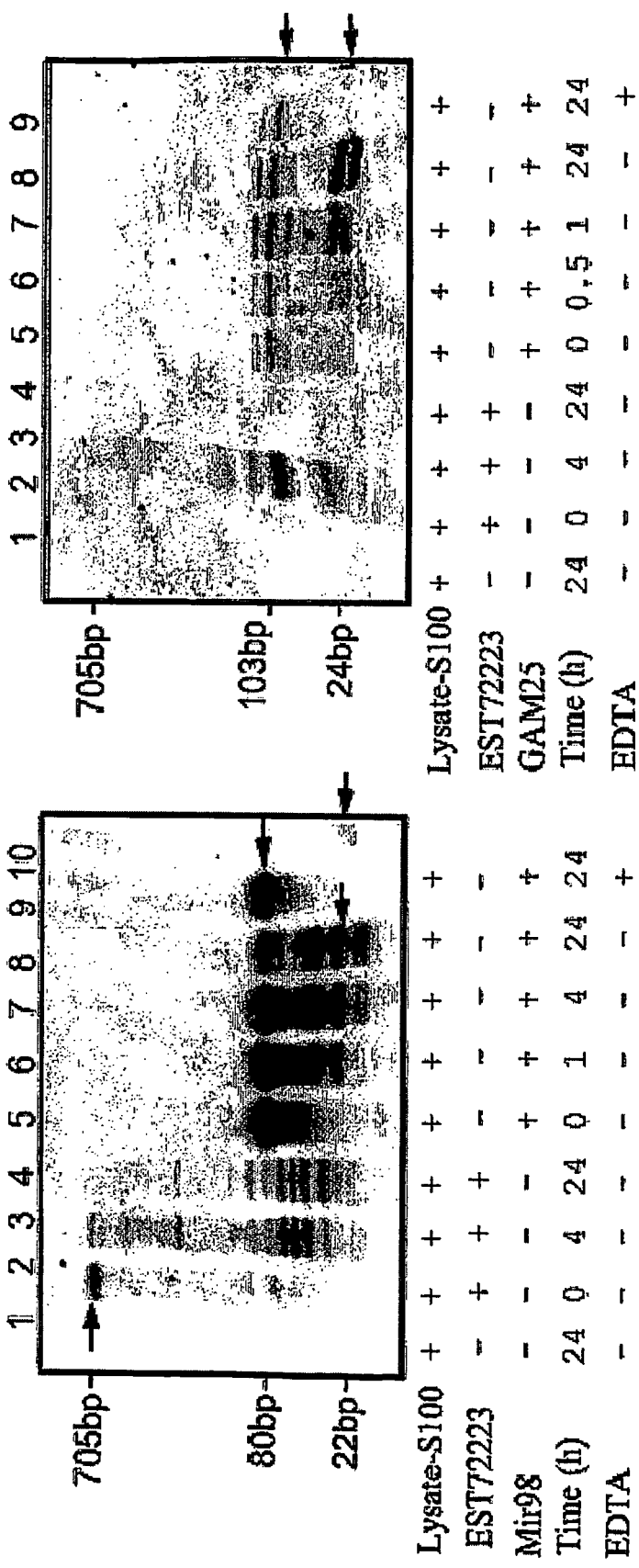
FIGS. 24B and 24C are pictures of laboratory results demonstrating laboratory confirmation of expression of known gene MIR98 and of novel bioinformatically detected gene GAM25 respectively, both of FIG. 24A, thus validating the bioinformatic gene detection system of the present invention.

Reference is now made to FIGS. 24B and 24C that are pictures of laboratory results, which when taken together demonstrate laboratory confirmation of expression of the bioinformatically detected novel gene of FIG. 24A.

In two parallel experiments, an enzymatically synthesized capped, EST72223 RNA transcript, was incubated with Hela S100 lysate for 0 minutes, 4 hours and 24 hours. RNA was subsequently harvested, run on a denaturing polyacrylamide gel, and reacted with a 102 nt and a 145 nt antisense MIR98 and GAM25 transcript probes respectively. The Northern blot results of these experiments demonstrated processing of EST72223 RNA by Hela lysate (lanes 2-4, in 24B and 24C), into ~80 bp and ~22 bp segments, which reacted with the MIR98 probe (24B), and into ~100 bp and ~24 bp segments, which reacted with the GAM25 probe (24C). These results demonstrate the processing of EST72223 by Hela lysate into MIR98 and GAM25. It is also appreciated from FIG. 24C (lane 1) that Hela lysate itself reacted with the GAM25 probe, in a number of bands, including a ~100 bp band, indicating that GAM25-precursor is endogenously expressed in Hela cells. The presence of additional bands, higher than 100 bp in lanes 5-9 probably corresponds to the presence of nucleotide sequences in Hela lysate, which contain the GAM25 sequence.

In addition, in order to demonstrate the kinetics and specificity of the processing of MIR98 and GAM25 miRNA precursors into their respective miRNA's, transcripts of MIR98 and of the bioinformatically predicted GAM25, were similarly incubated with Hela S100 lysate, for 0 minutes, 30 minutes, 1 hour and 24 hours, and for 24 hours with the addition of EDTA, added to inhibit Dicer activity, following which RNA was harvested, run on a polyacrylamide gel and reacted with MIR98 and GAM25 probes. Capped transcripts were prepared for in-vitro RNA cleavage assays with T7 RNA polymerase including a $m^7G(5')ppp(5')$ G-capping reaction using the m Message m Machine kit (Ambion). Purified PCR products were used as template for the reaction. These were amplified for each assay with specific primers containing a T7 promoter at the 5' end and a T3 RNA polymerase promoter at the 3'end. Capped RNA transcripts were incubated at 30° C. in supplemented, dialysis concentrated, Hela S100 cytoplasmic extract (4C Biotech, Seneffe, Belgium). The Hela S100 was supplemented by dialysis to a final concentration of 20 mM Hepes, 100 mM KCl, 2.5 mM $MgCl_2$, 0.5 mM DTT, 20% glycerol and protease inhibitor cocktail tablets (Complete mini Roche Molecular Biochemicals). After addition of all components, final concentrations were 100 mM capped target RNA, 2 mM ATP, 0.2 mM GTP, 500 U/ml RNasin, 25 µg/ml creatine kinase, 25 mM creatine phosphate, 2.5 mM DTT and 50% S100 extract. Proteinase K, used to enhance Dicer activity (Zhang H, Kolb F A, Brondani V, Billy E, Filipowicz W. Human Dicer preferentially cleaves dsRNAs at their termini without a requirement for ATP.EMBO J. 2002 Nov. 1; 21(21): 5875-85) was dissolved in 50 mM Tris-HCl pH 8, 5 mM $CaCl_2$, and 50% glycerol, was added to a final concentration of 0.6 mg/ml. Cleavage reactions were stopped by the addition of 8 volumes of proteinase K buffer (200 Mm Tris-Hcl, pH 7.5, 25 m M EDTA, 300 mM NaCl, and 2% SDS) and incubated at 65° C. for 15 min at different time points (0, 0.5, 1, 4, 24 h) and subjected to phenol/chloroform extraction. Pellets were dissolved in water and kept frozen. Samples were analyzed on a segmented half 6%, half 13% polyacrylamide 1×TBE-7M Urea gel.

The Northern blot results of these experiments demonstrated an accumulation of a ~22 bp segment which reacted with the MIR98 probe, and of a ~24 bp segment which reacted with the GAM25 probe, over time (lanes 5-8). Absence of these segments when incubated with EDTA (lane 9), which is known to inhibit Dicer enzyme (Zhang et al., 2002), supports the notion that the processing of MIR98 and GAM25 miRNA's from their precursors is mediated by Dicer enzyme, found in Hela lysate. The molecular sizes of EST72223, MIR-98 and GAM25 are indicated by arrows.

Transcript products were 705 nt (EST72223), 102 nt (MIR98), 125 nt (GAM25) long.EST72223 was PCR amplified with T7-EST 72223 forward primer:

5'-TAATACGACTCACTATAGGCCCTTATTA-GAGGATTCTGCT-3' (SEQ ID NO: 548166)

and T3-EST72223 reverse primer:

5'-AATTAACCCTCACTAAAG-GTTTTTTTTTCCTGAGACAGAGT-3' (SEQ ID NO: 548167).

MIR98 was PCR amplified using EST72223 as a template with T7MIR98 forward primer:

5-'TAATACGACTCACTATAGGGTGAGGTAG-TAAGTTGTATTGTT-3' (SEQ ID NO: 548168)

and T3MIR98 reverse primer:

5'-AATTAACCCTCACTAAAGGGAAAGTAG-TAAGTTGTATAGTT-3' (SEQ ID NO: 548169).

GAM25 was PCR amplified using EST72223 as a template with GAM25 forward primer: 5'-GAGGCAGGAGAAT-TGCTTGA-3' (SEQ ID NO: 548170) and T3-EST72223 reverse primer:

5'-AATTAACCCTCACTAAAGGCCTGAGACA-GAGTCTTGCTC-3' (SEQ ID NO: 548171).

To validate the identity of the band shown by the lower arrow in FIG. 24C, a RNA band parallel to a marker of 24 base was excised from the gel and cloned as in Elbashir et al (2001) and sequenced. 90 clones corresponded to the sequence of GAM25, three corresponded to GAM25* (the opposite arm of the hairpin with a 1-3 nucleotide 3' overhang) and two to the hairpin-loop.

GAM25 was also validated endogenously by sequencing from both sides from a HeLa YM100 total-RNA "ligation" libraries, utilizing hemispecific primers as detailed in FIG. 22.

Taken together, these results validate the presence and processing of a novel MIR gene product, GAM25, which was predicted bioinformatically. The processing of this novel gene product, by Hela lysate from EST72223, through its precursor, to its final form was similar to that observed for known gene, MIR98.

It is appreciated that the data presented in FIGS. 24A, 24B and 24C when taken together validate the function of the bioinformatic gene detection engine 100 of FIG. 9. FIG. 24A shows a novel GAM gene bioinformatically detected by the bioinformatic gene detection engine 100, and FIGS. 24B and 24C show laboratory confirmation of the expression of this novel gene. This is in accord with the engine training and validation methodology described hereinabove with reference to FIG. 10.

It is appreciated by persons skilled in the art that the present invention is not limited by what has been particularly shown and described hereinabove. Rather the scope of the present invention includes both combinations and subcombinations of the various features described hereinabove as well as variations and modifications which would occur to persons skilled in the art upon reading the specifications and which are not in the prior art.

DETAILED DESCRIPTION OF LARGE TABLES

Table 1 comprises data relating to the source and location of novel GAM genes of the present invention, and contains the following fields:

| | |
|---|---|
| GENE NAME | Rosetta Genomics Ltd. gene nomenclature (see below) |
| GAM SEQ-ID | GAM Seq-ID, as in the Sequence Listing |
| PRECUR SEQ-ID | GAM precursor Seq-ID, as in the Sequence Listing |
| ORGANISM | Abbreviated (hsa = *Homo sapiens*) |
| CHR | Chromosome encoding the GAM gene |
| CHROMOSOME OFFSET | Offset of GAM precursor sequence on chromosome |
| SOURCE_REF-ID | Accession number of source sequence |
| SOURCE_OFFSET | Offset of GAM precursor sequence on source sequence |
| SRC | Source-type of GAM precursor sequence (see below) |
| GAM ACC | GAM Prediction Accuracy Group (see below); |

Table 2 comprises data relating to GAM precursors of novel GAM genes of the present invention, and contains the following fields:

| | |
|---|---|
| GENE NAME | Rosetta Genomics Ltd. gene nomenclature (see below) |
| PRECUR SEQ-ID | GAM precursor Seq-ID, as in the Sequence Listing |
| PRECURSOR SEQUENCE | GAM precursor nucleotide sequence (5' to 3') |
| FOLDED-PRECURSOR | Schematic representation of the GAM folded precursor, beginning 5' end (beginning of upper row) to 3' end (beginning of lower row), where the hairpin loop is positioned at the right part of the draw. |
| SRC | Source-type of GAM precursor sequence (see below) |
| GAM ACC | GAM Prediction Accuracy Group (see below); |

Table 3 comprises data relating to GAM genes of the present invention, and contains the following fields:

TABLE 3

| Genes | |
|---|---|
| GENE NAME | Rosetta Genomics Ltd. gene nomenclature (see below) |
| GAM SEQ-ID; GENE_SEQUENCE | GAM Seq-ID, as in the Sequence Listing Sequence (5' to 3') of the mature, 'diced' GAM gene |
| PRECUR SEQ-ID | GAM precursor Seq-ID, as in the Sequence Listing |
| SOURCE_REF-ID | Accession number of the source sequence |
| SRC | Source-type of GAM precursor sequence (see below) |
| GAM ACC | GAM Prediction Accuracy Group (see below); |

Table 4 comprises data relating to target-genens and binding sites of GAM genes of the present invention, and contains the following fields:

| | |
|---|---|
| GENE NAME | Rosetta Genomics Ltd. gene nomenclature (see below) |
| GAM SEQ-ID; | GAM Seq-ID, as in the Sequence Listing |
| TARGET | GAM target protein name |
| #BS | Number of binding sites of GAM onto Target |
| TARGET SEQ-ID | Target binding site Seq-ID, as in the Sequence Listing |
| TARGET REF-ID | Target accession number (GenBank) |
| UTR | Untranslated region of binding site/s (3' or 5') |
| UTR OFFSET | Offset of GAM binding site relative to UTR |
| TAR-BINDING-SITE-SEQ | Nucleotide sequence (5' to 3') of the target binding site |
| BINDING-SITE-DRAW | Schematic representation of the binding site, upper row present 5' to 3' sequence of the GAM, lower row present 3' to 5' sequence of the target. |
| SRC | Source-type of GAM precursor sequence (see below) |
| GAM ACC | GAM Prediction Accuracy Group (see below); |
| BS ACC | Binding-Site Accuracy Group (see below) |
| TAR ACC | Target Accuracy Group (see below); |

Table 5 comprises data relating to functions and utilities of novel GAM genes of the present invention, and containing the following fields:

| | |
|---|---|
| GENE NAME | Rosetta Genomics Ltd. gene nomenclature (see below) |
| TARGET | GAM target protein name |
| GENE_SEQUENCE | Sequence (5' to 3') of the mature, 'diced' GAM gene |
| GENE-FUNCTION | Description of the GAM functions and utilities |
| SRC | Source-type of GAM precursor sequence (see below) |
| GAM ACC | GAM Prediction Accuracy Group (see below) |
| TAR ACC | Target Accuracy Group (see below) |
| TAR DIS | Target Accuracy Group (see below); |

Table 6 comprises a bibliography of references supporting the functions and utilities of novel GAM genes of the present invention, and contains the following fields:

TABLE 6

| Gene Function References - Bibliography. | |
|---|---|
| GENE NAME | Rosetta Genomics Ltd. gene nomenclature (see below) |
| TARGET | GAM target protein name |
| REFERENCES | list of references relating to the target gene, |
| SRC | Source-type of GAM precursor sequence (see below) |
| GAM ACC | GAM Prediction Accuracy Group (see below) |
| TAR ACC | Target Accuracy Group (see below); and |

Table 7 comprises data relating to novel GR genes of the present inventions, and contains the following fields:

| | |
|---|---|
| GENE NAME | Rosetta Genomics Ltd. GR gene nomenclature |
| SOURCE START_OFFSET | Start-offset of GR gene relative to source sequence |
| SOURCE END_OFFSET | End-offset of GR gene relative to source sequence |
| SOURCE_REF-ID | Accession number of the source sequence |
| GAMS_ID'S_IN_GR | List of the GAM genes in the GR cluster |
| SRC | Source-type of GAM precursor sequence (see below) |
| GR ACC | GR Prediction Accuracy Group (see below). |

The following conventions and abbreviations are used in the tables:

GENE NAME is a RosettaGenomics Ltd. gene nomenclature. All GAMs are designated by GAMx.1 or GAMx.2 where x is the unique SEQ-ID. If the GAM precursor has a single prediction for GAM, it is designated by GAMx.1. Otherwise, the higher accuracy GAM prediction is designated by GAMx.1 and the second is designated by GAMx.2.

SRC is a field indicating the type of source in which novel genes were detected, as one of the following options: (1) TIGR Intergenic, (3) EST or Unigene Intron Intergenic, (4) TIGR Intron, (6) DNA Intergenic, (7) DNA Intron, (8) DNA Exon. Sequences are based on NCBI Build33 of the human genome. TIGR source is based on "Tentative Human Consensus" (THC) The Institute for Genomic Research which are not found in mRNA Intron/Exon according to NCBI GenBank genome annotation.

GAM ACC (GAM Prediction Accuracy Group) of gene prediction system: A—very high accuracy, B—high accuracy, C— moderate accuracy, D—low accuracy, as described hereinbelow with reference to FIG. 21.

BS ACC (Binding-Site Accuracy Group) indicates accuracy of total GAM-target binding prediction, considering the number of binding sites a GAM has on the target's UTR; A—very high accuracy, B—high accuracy, C—moderate accuracy, as described hereinbelow with reference to FIG. 14B.

TAR ACC (Target Accuracy Group) indicates accuracy of target binding site prediction, A—very high accuracy, B—high accuracy, C—moderate accuracy, as described hereinbelow with reference to FIG. 14B.

TAR DIS (Target Disease Relation Group) 'A' indicates if the target gene is known to have a specific causative relation to a specific known disease, based on the OMIM database. It is appreciated that this is a partial classification emphasizing genes which are associated with 'single gene' diseases etc. All genes of the present invention ARE associated with various diseases, although not all are in 'A' status.

GR ACC (GR Prediction Accuracy Group) indicates the maximum gene prediction accuracy among GAM genes of the cluster, A—very high accuracy, B—high accuracy, C—moderate accuracy, as described hereinbelow with reference to FIG. 14B.

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US07618814B2). An electronic copy of the "Sequence Listing" will also be available from the USPTO upon request and payment of the fee set forth in 37 CFR 1.19(b)(3).

The invention claimed is:

1. An isolated nucleic acid, wherein the sequence of the nucleic acid is selected from the group consisting of:
   (a) SEQ ID NO: 15215;
   (b) a DNA encoding the nucleic acid of (a), wherein the DNA is identical in length to (a); and
   (c) the complement of (a) or (b), wherein the complement is identical in length to (a).

2. A vector comprising the nucleic acid of claim 1.

3. A probe comprising the nucleic acid of claim 1.

4. An isolated nucleic acid, wherein the sequence of the nucleic acid is selected from the group consisting of:
   (a) SEQ ID NO: 1600;
   (b) a DNA encoding the nucleic acid of (a), wherein the DNA is identical in length to (a); and
   (c) the complement of (a) or (b), where in the complement is identical in length to (a).

5. A vector comprising the nucleic acid of claim 4.

6. A probe comprising the nucleic acid of claim 4.

* * * * *